(12) United States Patent
Ertan-Ahmed et al.

(10) Patent No.: US 11,813,310 B2
(45) Date of Patent: Nov. 14, 2023

(54) LONG-ACTING G-CSF FOR PREVENTING NEUTROPENIA OR REDUCING DURATION OF NEUTROPENIA

(71) Applicant: ILKOGEN ILAÇ SANAYI VE TICARET A.S., Istanbul (TR)

(72) Inventors: Senem Ertan-Ahmed, Pendik-Istanbul (TR); Adem Sahin, Pendik-Istanbul (TR); Hatice Oncel, Sancaktepe-Istanbul (TR); Onur Pinarbasli, Cankaya-Ankara (TR); Nagehan Sarracoglu, Cankaya-Ankara (AR)

(73) Assignee: ILKOGEN ILAÇ SANAYI VE TICARET A.S., Istanbul (TR)

( * ) Notice: Subject to any disclaimer, the term of this patent is extended or adjusted under 35 U.S.C. 154(b) by 608 days.

(21) Appl. No.: 16/748,057

(22) Filed: Jan. 21, 2020

(65) Prior Publication Data
US 2020/0255842 A1    Aug. 13, 2020

Related U.S. Application Data

(60) Provisional application No. 62/804,988, filed on Feb. 13, 2019.

(51) Int. Cl.
| | |
|---|---|
| *A61K 38/19* | (2006.01) |
| *A61K 47/68* | (2017.01) |
| *A61P 7/00* | (2006.01) |
| *C07K 1/14* | (2006.01) |
| *C07K 19/00* | (2006.01) |
| *A61P 35/00* | (2006.01) |
| *A61K 38/00* | (2006.01) |
| *C07K 14/47* | (2006.01) |
| *C12N 15/62* | (2006.01) |
| *C07K 14/53* | (2006.01) |

(52) U.S. Cl.
CPC ............ *A61K 38/193* (2013.01); *A61K 47/68* (2017.08); *A61P 7/00* (2018.01); *A61K 38/00* (2013.01); *C07K 14/47* (2013.01); *C07K 14/53* (2013.01); *C07K 19/00* (2013.01); *C07K 2317/524* (2013.01); *C07K 2317/53* (2013.01); *C07K 2317/60* (2013.01); *C07K 2319/30* (2013.01); *C12N 15/62* (2013.01)

(58) Field of Classification Search
CPC ...... A61K 38/193; A61K 47/68; C07K 14/53; C07K 19/00; C07K 2319/30; A61P 7/00; A61P 35/00
See application file for complete search history.

(56) References Cited

U.S. PATENT DOCUMENTS

| 8,586,038 B2 | 11/2013 | Yang et al. |
| 8,586,048 B2 | 11/2013 | Yang et al. |
| 2003/0082679 A1 | 5/2003 | Sun et al. |
| 2012/0276097 A1 | 11/2012 | Yang et al. |
| 2012/0294829 A1 | 11/2012 | Lee et al. |
| 2016/0362473 A1 | 12/2016 | Wang et al. |

FOREIGN PATENT DOCUMENTS

| EP | 2 162 472 B1 | 2/2013 |
| EP | 3 028 713 A1 | 6/2016 |
| WO | 2019/212429 A2 | 11/2019 |

OTHER PUBLICATIONS

Trial Protocol for EudraCT No. 2015-002693-20 (hereafter "Trial Protocol for EudraCT '20"), EU Clinical Trials Register Database, dated Nov. 3, 2015; available on-line at https://www.clinicaltrialsregister.eu/ctr-search/trial/2015-002693-20/BG; 8 pages as printed.*
"EudraCT & EU-CTR Question and Answer table" (V1.0, Oct. 2017, 19 pages, no author indicated).*
Burris et al, 2010. J Oncol Pract. 6(3): 133-140.*
Ilkogen Ilac San. Ve Tic. A.S., "Clinical trial results: A randomized, parallel group, multi-centre phase-2 study of GX-G3 compared with pegfilgrastim as an adjunct to chemotherapy in patients with Non-Hodgkin's Lymphoma", EU Clinical Trials Register, Mar. 27, 2019, pp. 1-10 ( 10 pages).
Senem Ertan-Ahmed et al., "GX-G3, a long-acting G-CSF, compared with pegfilgrastim in reducing duration of severe neutropenia after chemotherapy for non-Hodgkin's lymphoma", Journal of Clinical Oncology, May 26, 2019, No. 15, (5 pages).
Yun Jung Kim et al., "Preclinical evaluation of a biobetter candidate: Pharmacokinetics and pharmacodynamics of GX-G3 in healthy and neutropenia-induced rats", Drug Development Research, Sep. 26, 2019, vol. 80, No. 6, pp. 807-813 (7 pages).
U.S. National Library of Medicine, "Phase I Study GX-G3 in Healthy Subjects (GX-G3)", Sep. 26, 2013, Retrieved from: https://clinicaltrials.gov/ct2/show/NCT01951027, (6 pages).
International Search Report dated Mar. 27, 2020 in International Application No. PCT/IB2020/050447.
Yun Jung Kim et al., Abstract of "Preclinical evaluation of a biobetter candidate: Pharmacokinetics and pharmacodynamics of GX-G3 in healthy and neutropenia-induced rats", Drug Development Research, vol. 80, Issue 6, Jul. 11, 2019, 2 pages.

* cited by examiner

Primary Examiner — Zachary C Howard
(74) Attorney, Agent, or Firm — Sughrue Mion, PLLC

(57) ABSTRACT

A method for preventing neutropenia or reducing the duration of neutropenia in a patient by administering therapeutically effective amount of a human hybrid (hy) Fc fused granulocyte colony stimulating factor (G-CSF) developed as next-generation G-CSF.

16 Claims, 25 Drawing Sheets

Specification includes a Sequence Listing.

| | Object | Animal | Dose | Injection | NOAEL* |
|---|---|---|---|---|---|
| Safety Pharmacology | Example 5: (hERG assay) | - | 6, 30, 60 µg/mL | perfusion | > 60 µg/mL |
| | Example 6: (Irwin test & Body temperature) | Rat | 0, 1, 3, 10 mg/kg | SC, single | No effects |
| | Example 7: (Respiratory test) | Rat | 0, 1, 3, 10 mg/kg | SC, single | No effects |
| | Example 8: (Cardiovascular test) | Monkey | 0, 1, 3 mg/kg | SC, single | No effects |

*NOAEL: No Observed Adverse Effect Level

FIG. 10

Toxicology and toxicokinetic studies

| Object | Animal | Dose | Injection | NOAEL |
|---|---|---|---|---|
| Example 9 | Rat | 0, 1, 3, 10 mg/kg | SC; single | - |
| Example 10 | Rat | 0, 1, 3, 5 mg/kg | SC; every 2 days | - |
| Example 11 | Monkey | 0, 1, 5, 10 mg/kg | SC; every 2 days | |
| Example 12 | Rat | 0, 1, 3, 10 mg/kg | SC; weekly | 1 mg/kg |
| Example 13 | Monkey | 0, 1, 3, 10 mg/kg | SC; weekly | 3 mg/kg |
| Example 14 | Rat | 0, 1, 3, 5 mg/kg | SC; GD* 6, 9, 12, 15 | 5 mg/kg |
| Example 15 | Rabbit | 0, 0.035, 0.1, 0.3, 1 mg/kg | SC; GD* 6, 9, 12, 15, 18 | 0.035 mg/kg |
| Example 16 | Rat | 0, 1, 3, 5 mg/kg | SC; weekly | 1 mg/kg |
| Example 17 | Monkey | 0, 1, 3, 5 mg/kg | SC; weekly first, second dosing then every other week** | 3 mg/kg |

*GD: Gestation Day
**Days for dosing: 1, 8, 22, 36, 50, 64, 78, 92, 106, 120, 134, 148, 162, 176

FIG. 11

Treatment A, B, C, D: Study medication 24 h after R-CHOP

Treatment E: Study medication 72 h after R-CHOP

LONG-ACTING G-CSF FOR PREVENTING NEUTROPENIA OR REDUCING DURATION OF NEUTROPENIA

CROSS-REFERENCE TO RELATED APPLICATION

The present application claims the benefit of U.S. Provisional Application No. 62/804,988 filed on Feb. 13, 2019.

FIELD OF THE INVENTION

The present disclosure relates to a method for preventing neutropenia or reducing the duration of neutropenia in a patient by administering a long-acting hybrid Fc gusion G-CSF.

BACKGROUND OF THE INVENTION

Leukopenia, which is a reduced level of white blood cells (WBC), and neutropenia, which is a reduced level of neutrophils are critical disorders that result in an increased sensibility to various types of infections. Neutropenia can be chronic, e.g. in patients infected with HIV, or acute, e.g. in cancer patients undergoing chemotherapy or radiation therapy. Various factors such as anti-cancer chemotherapy drugs, anti-cancer radiation therapy, infectious diseases, congenital defects or vitamin B12/B9 deficiency can trigger neutropenia. A significant decrease in neutrophils which makes the patient more susceptible to bacterial infections is a common and serious complication in patients who receive anti-cancer therapy (chemotherapy and/or radiation therapy).

Neutrophils are made in the bone marrow and they are short-lived cells that travel extensively throughout the body; unlike some of the other white blood cells they can move freely through the walls of veins and into the tissues of the body to immediately attack all antigens. Neutropenia is classified by the neutrophil count and the relative risk of infection. It is defined as absolute neutrophil count (ANC) value lower than about $1.0 \times 10^9$/L. According to neutrophil count it has following classifications; moderate neutropenia (500 to 1000/μL), or severe neutropenia 500/μL). Febrile neutropenia (FN) refers to the occurrence of a fever during a period of significant neutropenia. Moderate and severe neutropenia or febrile neutropenia leads to a reduction in the dose of the drugs used in chemotherapy or to delay the treatment, which resulting in the treatment process being less effective. For patients with severe neutropenia or febrile neutropenia, exhibited by ANC value below about $0.5 \times 10^9$/L, even relatively minor infections can be serious and even life-threatening.

Recently, various forms of leukopenia and neutropenia are treated or regulated with granulocyte colony-stimulating factor (G-CSF) or polyethylene glycol (PEG) modified G-CSF derivative. In high-risk chemotherapy regimen with more than 20% possibility of febrile neutropenia, prophylactic use of G-CSF is suggested. In patients receiving autologous peripheral blood stem cell transplantation, G-CSF is used to mobilize cluster of designation 34+ (CD34+) hematopoietic stem cells to peripheral blood after completion of cancer chemotherapy. G-CSF is also used in hematopoietic stem cell mobilization for allogenic hematopoietic stem cell transplantation in patients undergoing cross blood stem cell transplantation. Additionally, G-CSF agent is used to treat neutropenia to increase the number of neutrophils after hematopoietic stem cell transplantation, myelodysplastic syndromes, aplastic anemia, congenital and idiopathic neutropenia, human immunodeficiency virus (HIV) infection. The principal biological effect of G-CSF in vivo is to stimulate the growth and development of certain white blood cells known as neutrophilic granulocytes or neutrophils (Welte et al., *PNAS-USA* 82:1526-1530, 1985, Souza et al, *Science,* 232:61-65, 1986).

The generated neutrophils in the bone marrow are controlled by G-CSF. It takes effect when G-CSF is combined with granulocyte colony-stimulating receptor on the surface of the cells in the bone marrow; receptor is usually generated from the precursor cell of granulocyte and mature neutrophil, and higher dense is generated in the latter phase of differentiation and maturation process. As a result, G-CSF promotes the entrance of precursor cells, such as myeloblast, promyelocyte, and myelocyte, in the bone marrow into the cell cycle after combining with a receptor; it triggers more frequent cell division resulting in the promotion of cell proliferation and the increase of life span of granulocytes. In addition, G-CSF promotes the transfer to the blood stream in a short time (4-24 hours) from the bone marrow and it contributes to the increase in the number of neutrophil. Moreover, G-CSF contributes to the proliferation and differentiation of the hematopoietic stem cell, such as CFU-G (colony forming unit-granulocyte).

The amino acid sequence of human G-CSF (hG-CSF) was reported by Nagata et al. Nature 319:415-418, 1986. hG-CSF is a monomelic protein that dimerizes the G-CSF receptor by formation of a 2:2 complex of 2 G-CSF molecules and 2 receptors (Horan et al. (1996), *Biochemistry* 35(15): 4886-96). A recombinant, methionyl human G-CSF (r-metHuG-CSF), a 175-residue protein, was produced first in *E. coli* (Hill et al. (1993), *Proc. Natl. Acad. Sci. U.S.A.* 90, 5167-5171). Filgrastim, marketed as Neupogen® at 1991, the first of these G-CSF-containing drugs (non-glycosylated combinant methionyl human granulocyte colony-stimulating factor, rhuG-CSF), should be administered daily during the course of chemotheraphy due to its short half-life (between 3.5 and 3.8 hours). The plasma half-life of filgrastim could be extended to 18-80 hours to be subcutaneous (SC) administered less frequently with the development of pegfilgrastim which contains a single N-terminally linked 20 kDa polyethylene glycol (PEG) group on G-CSF (Frampton, Lee et al. 1994, Molineux 2003, Molineux 2004). This compound was approved by the FDA (U.S. Food and Drug Administration) in 2002 under the tradename Neulasta®. Therefore, the recommended pegfilgrastim dosing is once per chemotherapy cycle.

Recently, fusion proteins manufactured using an immunoglobulin (Ig) has been researched and developed. Ig is a major component of blood. Human Ig (hIg) includes various classes such as IgG, IgM, IgA, IgD, and IgE (Roitt et al., "*Immunology"* 1989, Gower Medical Publishing, London, U. K.; New York, N. Y). As described in U.S. Pat. No. 5,045,312, human growth hormone is conjugated to bovine serum albumin or mouse immunoglobulin by the use of a carbodiimide or glutaraldehyde as cross-linking agent. The conjugates have enhanced activity, when compared with unmodified growth hormone. Modifications on Fc-domain such as altering glycosylation sites have known to improve therapeutic effect (R. J. Sola and K. Griebenow, (2009), *J Pharm Sci.* 98(4): 1223-1245). Additionally, when an active substance is fused to the Fragment crystallizable (Fc) region of an antibody, an extended circulation or clinical activity is also achieved.

However, unlike the fusion with the extracellular domains of cell surface receptors, the fusion of soluble proteins to IgGs leads to reduced biological activities, compared to non-fused cytokine or growth factors. The reason is that the chimeric proteins exist as dimers where two active proteins are in close proximity; this leads to a steric hindrance of fused-IgGs towards their target molecules. Therefore, this problem should be overcome to make an efficient fusion protein (e.g., US 20120276097 A1, the entire content of which is incorporated herein by reference).

The other limitation of the Fc fusion technology is the occurrence of undesired-immune responses. The Fc domain of the immunoglobulin has also effector functions such as antibody dependent cell-mediated cytotoxicity (ADCC) or complement-dependent cytotoxicity (CDC). This effector functions are generally achieved via interaction between the Fc region of the Ig and Fc receptors (FcR) on effector cells or via complement binding.

Therefore, the blocking of effector functions of Fc should be performed to reduce the undesired responses such as cell death, cytokine release, or inflammation (US 20120276097 A1).

Overall, it is known that usage of G-CSF based product such as filgrastim (Neupogen®) without any modification is limited due to its short half-life. Pegfilgrastim (Neulasta®) has comparably an increased half-life, but it is known that PEG could have some adverse effects and pegylation brings an additional production step. Fc-fusion construct is in general a useful and commonly utilized technology platform specifically in clinical applications due to extending short half-life of small proteins (Czajkowsky, Hu, Shao, & Pleass, 2012; Strohl, 2015). However, one of the major limitations of the Fc fusion technology is the presence of undesired immune responses.

The Hybrid Fc (hyFc) platform, which is used in the present embodiment, has been invented both to further improve plasma half-life of the conjugated drugs and to reduce cytotoxicity and immunogenicity (EP20080766022, U.S. Pat. No. 8,586,038B2). The entire content of U.S. Pat. No. 8,586,038B2 is incorporated herein by reference. For this purpose, two different immunoglobulins having no ADCC and CDC response were combined genetically. Hybrid Fc is derived from combinations of human IgG subclasses or combinations of human IgD and IgG. The hybrid Fc is effective, when joined to a biologically active molecule, to increase serum half-life of the biologically active molecule as well as increase expression level of the polypeptide when a nucleotide coding for the Fc-polypeptide fusion protein is expressed. Thus, Hybrid Fc (hyFc)-Fused G-CSF also has a longer plasma half-life, efficient expression level, eliminated cytotoxicity and reduced immunogenicity (U.S. Pat. No. 8,586,048 82). In this respect, hyFc fused G-CSF is a unique and originator molecule, where the Fc part itself is a fusion of two immunoglobulin molecules and this first fusion is further fused to the active molecule.

Accordingly, in this study, a method employing a human hybrid (hy) Fc fused granulocyte colony stimulating factor (a long acting G-CSF) which is a next-generation G-CSF (3rd generation G-CSF) was developed for preventing neutropenia or reducing the duration of neutropenia.

BRIEF DESCRIPTION OF THE INVENTION

In a first embodiment of the present invention is to provide a method of treatment that allows a long-acting hybrid Fc fusion G-CSF to be administered in a therapeutically effective amount to a subject.

In an embodiment of the present invention is to provide a method of preventing neutropenia or reducing the duration of neutropenia in a subject wherein a long-acting hybrid Fc fusion G-CSF to be administered at a dose range between about 200 µg/kg and about 400 µg/kg.

In another embodiment of the present invention is to provide a method of preventing neutropenia or reducing the duration of neutropenia in a human subject receiving anti-cancer therapy (chemotheraphy or radiation therapy) wherein a long-acting hybrid Fc fusion G-CSF to be administered at a dose range between about 200 µg/kg and about 400 µg/kg.

In another embodiment of the present invention is to provide a method of preventing neutropenia or reducing the duration of neutropenia in a human receiving chemotheraphy wherein the therapeutically effective amount of hybrid Fc fusion G-CSF, a long acting G-CSF, is subcutaneously (SC) administered at a dose range between about 200 µg/kg and about 400 µg/kg.

In another embodiment of the present invention is to provide a method of preventing neutropenia or reducing the duration of neutropenia in a human receiving chemotheraphy wherein the therapeutically effective amount of hybrid Fc fusion G-CSF, a long acting G-CSF, is subcutaneously (SC) administered at a dose range between about 200 µg/kg and about 400 µg/kg having an improved pharmacokinetic property, such as an increased serum half-life and/or an increased AUC and $C_{max}$, compared to the PEGylated G-CSF Neulasta®.

In a further embodiment of the present invention is to provide a method of increasing neutrophil levels in a human subject having circulating neutrophils of lower than about $1.0 \times 10^9$/L or lower than about $0.5 \times 10^9$/L wherein a long-acting hybrid Fc fusion G-CSF to be administered at a dose range between about 200 µg/kg and about 400 µg/kg.

List of Definition of Terms

In the description and claims below, the following definitions are applied.

The term 'protein' is also meant 'polypeptide' refers to an amino acid polymer, comprising natural and/or non-natural D- or L-amino acids as are well understood in the art. G-CSF may be referred to as either a protein or polypeptide. Protein may refer to a peptide or fragments thereof, for example a fragment of G-CSF.

The term 'G-CSF' refers to a G-CSF protein, and fragments, homologs and variants thereof. One form of G-CSF variants is G-CSF mutein as disclosed in U.S. Pat. No. 5,214,132, the entire content of which is incorporated herein by reference. A GCSF mutein, which has properties equivalent or superior to native G-CSF and has the same uses as G-CSF, has the same amino acid sequence as native human G-CSF except at positions 1, 3, 4, 5, and 17, where instead of the native G-CSF amino acids, the mutein has instead Ala, Thr, Tyr, Arg, and Ser respectively. G-CSF protein may comprise naturally occurring modification such as glycosylation, but in a preferred form is nonglycosylated and expressed from a bacteria cell. G-CSF may be derived from any species, including human, mouse, rat and others. A preferred form of G-CSF is human G-CSF for use in humans. G-CSF may be recombinant or native and may comprise natural and/or non-natural D- or L-amino acids as are well understood in the art.

The term 'therapeutically effective amount' refers to that amount of an active agent being administered which results in a desired therapeutic effect when administered to a subject in need of a G-CSF treatment. A "desired therapeutic effect" includes one or more of the following: 1) an amelioration of the symptom(s) associated with the disease or condition; 2) a delay in the onset of symptoms associated with the disease or condition; 3) increased longevity compared with the absence of the treatment; and 4) greater quality of life compared with the absence of the treatment.

The term 'cycle' refers to the period between the first days of administration of chemotherapy in consecutive cycles of chemotherapy.

The term 'subject' as used herein includes any human or nonhuman animal. In preferred embodiments, the subject is a mammal, preferably a human. In the present invention, the term 'subject', 'patient' and 'individual' may be used interchangeably.

The term 'anti-cancer therapy' refers treatment to stop or prevent cancer in a subject. In preferred embodiments, chemotherapy or radiation therapy are used as an anti-cancer therapy in order to promote cancer regression to the point of eliminating the cancer.

The term '$C_{max}$' refers to the maximum observed concentration taken directly from the serum concentration-time course profile. Unless otherwise specified, '$C_{max}$' refers to $C_{max}$ obtained based on baseline adjusted concentrations, i.e., concentrations obtained after subtracting the individual baseline from each individual time point ($C_t$-$C_o$).

The term '$t_{max}$' refers to time to maximum serum concentration, obtained directly from the observed concentration versus time data.

The term '$t_{1/2}$' or 'half-life' of a drug is the time it takes for its concentration in blood or serum to decrease by half.

The term 'AUC' or 'Area Under the Curve' is used in its normal meaning, i.e. as the area under the serum concentration versus time curve where the test molecule has been administered to a subject. Once the experimental concentration-time points have been determined, the AUC may conveniently be calculated by a computer program, such pas GraphPad Prism 3.01.

The term '$AUC_{last}$' refers to Area Under the Curve from time zero to time of last measurable concentration, calculated by linear up/log down trapezoidal summation.

The term '$AUEC_{last}$' refers to Area Under the Effect-time Curve from time zero to time of last point of quantifiable effect.

The term '$AUC_{inf}$' refers to Area Under the Curve from time zero extrapolated to infinity, calculated by linear up/log down trapezoidal summation and extrapolated to infinity by addition of the last quantifiable concentration divided by the elimination rate constant.

The term 'mean' represents the arithmetic mean value of the pharmacokinetic value unless otherwise specified.

The term 'AE' or 'adverse event' refers to that any untoward medical occurrence in a patient or clinical investigation patient administered a pharmaceutical product and which does not necessarily have to have a causal relationship with this treatment.

BRIEF DESCRIPTION OF THE FIGURES

In order that the invention may be readily understood and put into practical effect, preferred embodiments will now be described by way of example with reference to the accompanying figures.

FIG. 10 summarizes the non-clinical safety test results (Examples 5-8) of GX-G3.

FIG. 11 summarizes the non-clinical toxicity test results (Examples 9-17) of GX-G3.

In FIG. 12, error bars indicate standard errors (lower left: linear scale, upper right: log-linear scale).

In FIG. 13, error bars indicate standard errors (lower left: linear scale, upper right: log-linear scale).

In FIG. 14, symbols, horizontal lines, box heights, and whiskers indicate individual values, dose group medians, interquartile ranges, and minimums & maximums, respectively.

In FIG. 15, error bars indicate standard deviations.

In FIG. 16, symbols, horizontal lines, box heights, and whiskers indicate individual values, dose group medians, interquartile ranges, and minimums & maximums, respectively.

In FIG. 17, error bars indicate standard deviations.

In FIG. 18, symbols, horizontal lines, box heights, and whiskers indicate individual values, dose group medians, interquartile ranges, and minimums & maximums, respectively.

In FIG. 19, error bars indicate standard deviations.

In FIG. 20, error bars indicate standard deviations.

In FIG. 21, Error bars indicate standard deviations.

In FIG. 22, error bars indicate standard deviations.

In FIG. 23, error bars indicate standard deviations.

In FIG. 24, error bars indicate standard deviations.

DETAILED DESCRIPTION

Figure 1:
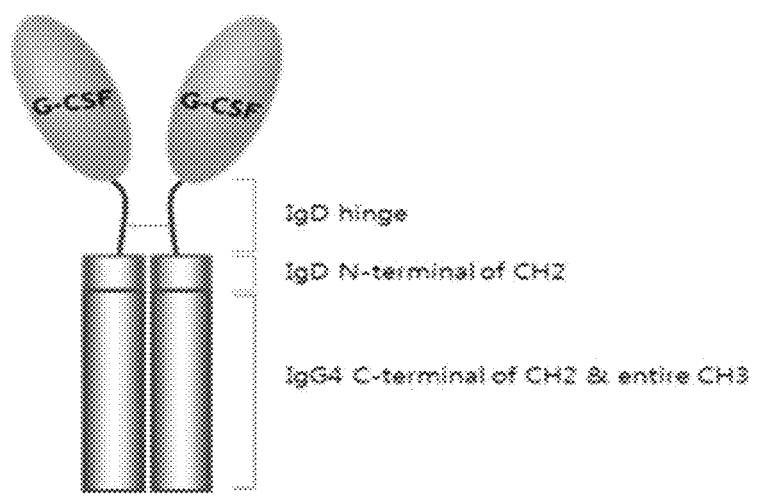
FIG. 1 is a protein structure of GX-G3 which is a fusion human G-CSF protein with homodimer structure in a hybridized form of hinge domain of IgD and Fc domain of IgG4.

One embodiment provides a method of preventing neutropenia or reducing the duration of neutropenia in a patient comprising administering a long-acting hybrid Fc fusion G-CSF in a therapeutically effective amount to a subject in need thereof.

Another embodiment of the present invention is to provide a method of increasing neutrophil levels in a human subject comprising administering a long-acting hybrid Fc fusion G-CSF in a therapeutically effective amount to a subject in need thereof.

According to these embodiments, for example the number of neutrophils is increased in the subject; the decrease in the number of neutrophils is prevented in the subject; the recovery of absolute neutrophil count is increased in the subject and the time to absolute neutrophil count recovery is reduced in the subject.

The long-acting hybrid Fc fusion G-CSF is represented by the following formula (I):

N'-G-Y-Z2-Z3-Z4-C'  Formula (I)

wherein
G is a G-CSF;
N' is the N-terminus of a polypeptide and C' is the C-terminus of a polypeptide;
Y is an amino acid sequence having 5 to 64 consecutive amino acid residues from the amino acid residue at position 162 toward the N-terminus, among the amino acid residues at positions from 99 to 162 of SEQ ID NO: 2;
Z2 is an amino acid sequence having 4 to 37 consecutive amino acid residues from the amino acid residue at position 163 toward the C-terminus, among the amino acid residues at positions from 163 to 199 of SEQ ID NO: 2;
Z3 is an amino acid sequence having 71 to 106 consecutive amino acid residues from the amino acid residue at position 220 toward the N-terminus, among the amino acid residues at positions from 115 to 220 of SEQ ID NO: 3; and
Z4 is an amino acid sequence having 80 to 107 consecutive amino acid residues from the amino acid residue at position 221 toward the C-terminus, among the amino acid residues at positions from 221 to 327 of SEQ ID NO: 3.

In an embodiment, the hyFc comprises the sequence of SEQ ID NO: 4.

One example of hybrid Fc fusion G-CSF comprises the amino acid sequence amino acid residues 31 through 449 of SEQ ID NO: 1. In SEQ ID NO: 1, amino acid residues 1-30 is signal sequence. The embodiment of hybrid Fc fusion G-CSF is also called as G-CSF-hyFc, GCSF-hFc, GX-G3, and HyGrastim. (The code name of GX-G3 is used henceforth.) GX-G3, a fusion protein in which human G-CSF is fused with human hyFc, has been developed with the goal of formulating a long-acting colony stimulating factor agent like pegfilgrastim. In contrast to pegfilgrastim, GX-G3 is prepared by inserting G-CSF-hyFc expressing gene in eukaryotic expression vector of pAD15 into MCS (multi-cloning site) and is obtained without any conjugation step. Unlike previously developed Fc products such as, abatacept, etanercept and Fc-fused G-CSF proteins, human Fc used in GX-G3 is in a hybridized form of human IgD-Fc and IgG4-Fc, named hybrid Fc (hyFc) (Cox et al., 2014). GX-G3 (FIG. 1) is a dimer protein consisting of 838 amino acids with molecular Formula of $C_{2072}H_{3258}N_{558}O_{630}S_{16}$. Among those amino acids, 30 amino acids of IgD hinge domain, 8 N-terminal acids of IgD CH2 domain and 107 amino acids composing C-terminal acid of IgG4 CH2 and CH3. 9 disulfide bonds location was identified in GX-G3 which has two O-glycosylation sites and two N-glycosylation sites. It is a homodimer of two molecular chains each comprising 1 antibody Fc part and 1 human G-CSF molecule. GX-G3 has a molecular size of 98 kDa.

In general, Fc of an antibody binds to FcRn (neonatal Fc receptor) of endothelial cells in the human body, thereby enabling the recycle of hyFc-fused proteins resulting in a product with markedly longer half-life (Strohl et al., 2015). Hinge-CH2 domain of IgD in hyFc construct has significant hinge flexibility but no binding affinity with FcγR inducing antibody-dependent cellular cytotoxicity (ADCC) while CH2-CH3 domain of IgG in hyFc does not exhibit any complement-dependent cellular cytotoxicity (CDC) reaction. Similar to other Fc fusion agents, it is expected that GX-G3 could have a long-acting characteristic in serum because of its FcRn binding affinity and decreasing renal clearance. Inherent human G-CSF amino acid sequence without the introduction of any mutation is used in the hyFc platform and IgD/IgG4 fused junction site of hyFc is buried in an unexposed region, thereby minimizing immunogenicity. Consequently, as might be expected, GX-G3 exhibits long acting characteristic as well as lower immunogenicity without antibody dependent cell-mediated cytotoxicity (ADCC) and complement-dependent cellular cytotoxicity (CDC) reactions (Kim, An, Lim, Yang, & Jeong, 2016).

GX-G3 was prepared by inserting G-CSF-hyFc expressing gene in eukaryotic expression vector of pAD15 into MCS (multi-cloning site). Unlike other G-CSF agents, the host cell used for GX-G3 preparation was Chinese Hamster Ovary (CHO) DG44. As a result of the special production methods, which allow producing fused G-CSF-hyFc in one step instead of producing the G-CSF and antibody Fc part separately and combining them with chemical reactions, GX-G3 has both better structural stability and lower production costs than other G-CSF agents.

In case of Fc-fused protein, such as GX-G3, it shows a long half-life in vivo caused by the recirculation through the combination of the FcRn receptor (neonatal Fc receptor) of endothelial cell in the body and the Fc region.

Besides, unlike existing other G-CSF agents, hyFc region of GX-G3 is a hybrid form; the hinge-CH2 region of IgD without a binding affinity of FcγR with high hinge flexibility causing antibody mediated cellulotoxicity, and the CH2-CH3 region of IgG4 with long half-life in serum because of a binding affinity of FcRn (neonatal Fc receptor) without complement activity reaction are designed in a hydrophobic form. These characteristics increased the activation by decreasing ADCC and CDC, and also decreased the immunogenicity. To reduce GX-G3-induced immunogenicity, only the native human G-CSF gene sequence was used for hyFc and the molecule did not contain any mutations that could cause side effects.

In addition, the stability of structure was increased by applying the manufacture method that is expressed together from CHO DG44 host cell by using pAD15 as an expression vector, instead of combining G-CSF and Fc region manufactured separately.

In the pharmaceutical composition of the present invention, the hyFc platform and G-CSF have amino acid sequence of humanized organisms. No additional fusion reaction is used, as the fusions both between the IgD and IgG and between G-CSF and the immunoglobulin part are provided through single genetic code and single transcription-translation reaction. The peptide bond between G-CSF and hyFc platform is through Proline-Arginine. Amino acid sequence of hy-Fc fused G-CSF monomer is provided below. Signal, G-CSF, N-terminal and hyFc sequences are denoted in the corresponding format. Schematic protein structure of hyFc fused G-CSF is shown below.

(SEQ ID NO: 1)
MAGPATQSPMKLMALQLLLWHSALWTVQEA*TPLGP*ASSLPQSFFLKCLEQ

VRKIQGDGAALQEKLCATYKLCHPEELVLLGHSLGIPWAPLSSCPSQALQ

LAGCLSQLHSGLFLYQGLLQALEGISPELGPTLDTLQLDVADFATTIWQQ

MEELGMAPALQPTQGAMPAFASAFQRRAGGVLVASHLQSFLEVSYRVLRH

LAQP<u>RNTGRGGEEKKKEKEKEEQEERETKTPECPSHT</u>

<u>QPLGVFLFPPKPKDTLMISRTPEVTCVVVDVSQEDPEVQFNWY</u>

<u>VDGVEVHNAKTKPREEQFNSTYRVVSVLTVIHQDWLNGKEY</u>

<u>KCKVSNKGLPSSIEKTISKAKGQPREPQVYTLPPSQEEMTKNQVSL</u>

<u>TCLVKGFYPSDIAVEWESNGQPENNYKTTPPVLDSDGS</u>

<u>FFLYSRLTVDKSRWQEGNVFSCSVMHEALHNHYTQKSLSLSLG</u>

<u>K</u>.

Patients undergoing cancer chemotherapy generally exhibit moderate to severe neutropenia after treatment. G-CSF-hyFc variant is effective at preventing neutropenia or reducing the time to absolute neutrophil count recovery, and the duration of neutropenia such that the duration of exposure to risk of infection is decreased seriously. Accordingly, the extent and duration of neutropenia is significantly prevented or reduced by administration of a therapeutically effective amount of G-CSF-hyFc in accordance with the methods of embodiments of the present invention.

In an embodiment, the patient suffers from moderate to severe neutropenia, e.g., having absolute neutrophil count lower than about $1.0 \times 10^9$/L, or lower than about $0.5 \times 10^9$/L. In an embodiment, the patient has insufficient circulating neutrophils.

In an embodiment, dosage is determined according to the weight of the patient, such that a therapeutically effective amount of hybrid Fc fusion G-CSF is about 200 μg/kg to 400 μg/kg, or about 250 μg/kg to 350 μg/kg.

According to an embodiment, the hybrid Fc fusion G-CSF is administered at a dose of about 200 μg/kg or above, about 210 μg/kg or above, about 220 μg/kg or above, about 230 μg/kg or above, about 240 μg/kg or above, about 250 μg/kg or above, about 260 μg/kg or above, about 270 μg/kg or above, about 280 μg/kg or above, about 290 μg/kg or above, about 300 μg/kg or above, about 310 μg/kg or above, about 320 μg/kg or above, about 330 μg/kg or above, about 340 μg/kg or above, about 350 μg/kg or above, about 360 μg/kg or above, about 370 μg/kg or above, about 380 μg/kg or above, or about 390 μg/kg or above, or at about 400 μg/kg.

In another embodiment, the hybrid Fc fusion G-CSF is administered at a dose of about 250 μg/kg or above, about 260 μg/kg or above, about 270 μg/kg or above, about 280 μg/kg or above, about 290 μg/kg or above, about 300 μg/kg or above, about 310 μg/kg or above, about 320 μg/kg or above, about 330 μg/kg or above, about 340 μg/kg or above, or at about 350 μg/kg.

According to an embodiment, the subject in need of G-CSF treatment may a cancer patient, who has received or is receiving anti-cancer treatment. For example, the subject may have received or be receiving at least one of radiation therapy, chemotherapy, or an operation.

The hybrid Fc fusion G-CSF may be administered at a dose of about 200 μg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

The hybrid Fc fusion G-CSF may be administered at a dose of about 210 μg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

The hybrid Fc fusion G-CSF may be administered at a dose of about 220 μg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

The hybrid Fc fusion G-CSF may be administered at a dose of about 230 μg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

The hybrid Fc fusion G-CSF may be administered at a dose of about 240 μg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

The hybrid Fc fusion G-CSF may be administered at a dose of about 250 μg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

The hybrid Fc fusion G-CSF may be administered at a dose of about 260 μg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

The hybrid Fc fusion G-CSF may be administered at a dose of about 270 µg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

The hybrid Fc fusion G-CSF may be administered at a dose of about 280 µg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

The hybrid Fc fusion G-CSF may be administered at a dose of about 290 µg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

The hybrid Fc fusion G-CSF may be administered at a dose of about 300 µg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

The hybrid Fc fusion G-CSF may be administered at a dose of about 310 µg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

The hybrid Fc fusion G-CSF may be administered at a dose of about 320 µg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

The hybrid Fc fusion G-CSF may be administered at a dose of about 330 µg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

The hybrid Fc fusion G-CSF may be administered at a dose of about 340 µg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

The hybrid Fc fusion G-CSF may be administered at a dose of about 350 µg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

The hybrid Fc fusion G-CSF may be administered at a dose of about 360 µg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

The hybrid Fc fusion G-CSF may be administered at a dose of about 370 µg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

The hybrid Fc fusion G-CSF may be administered at a dose of about 380 µg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

The hybrid Fc fusion G-CSF may be administered at a dose of about 390 µg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

The hybrid Fc fusion G-CSF may be administered at a dose of about 400 µg/kg or above once in a cycle of chemotherapy. The hybrid Fc fusion G-CSF may be administered at least 24 hours after the chemotherapy. In alternative embodiment, the hybrid Fc fusion G-CSF may be administered once for every two, three, four, or more cycles of chemotherapy.

In another embodiment, the hybrid Fc fusion G-CSF may be administered at a dose range between about 200 µg/kg and about 400 µg/kg once in a cycle of chemotherapy at least 24 hours after the chemotherapy. In alternative embodiment, the hybrid Fc fusion G-CSF may be administered once for every two, three, four, or more cycles of chemotherapy.

In another embodiment, the hybrid Fc fusion G-CSF may be administered at a dose range between about 250 µg/kg and about 400 µg/kg, between about 260 µg/kg and about 400 µg/kg, between about 270 µg/kg and about 400 µg/kg, between about 280 µg/kg and about 400 µg/kg, between about 290 µg/kg and about 400 µg/kg, between about 300 µg/kg and about 400 µg/kg, between about 310 µg/kg and about 400 µg/kg, between about 320 µg/kg and about 400 µg/kg, between about 330 µg/kg and about 400 µg/kg, between about 340 µg/kg and about 400 µg/kg, between about 350 µg/kg and about 400 µg/kg, between about 360 µg/kg and about 400 µg/kg, between about 370 µg/kg and about 400 µg/kg, between about 380 µg/kg and about 400 µg/kg, or between about 390 µg/kg and about 400 µg/kg, once in a cycle of chemotherapy at least 24 hours after the chemotherapy.

In another embodiment, the hybrid Fc fusion G-CSF may be administered at a dose range between about 250 µg/kg and about 350 µg/kg, between about 260 µg/kg and about 350 µg/kg, between about 270 µg/kg and about 350 µg/kg, between about 280 µg/kg and about 350 µg/kg, between about 290 µg/kg and about 350 µg/kg, between about 300 µg/kg and about 350 µg/kg, between about 310 µg/kg and about 350 µg/kg, between about 320 µg/kg and about 350 µg/kg, between about 330 µg/kg and about 350 µg/kg, or between about 340 µg/kg and about 350 µg/kg, once in a cycle of chemotherapy at least 24 hours after the chemotherapy.

In an embodiment, the hybrid Fc fusion G-CSF or a pharmaceutical composition comprising GX-G3 may be administered parenterally, intramuscularly, subcutaneously, ophthalmic, intravenously, intraperitoneally, intradermally, intraorbitally, intracerebrally, intracranially, intraspinally, intraventricular, intrathecally, intracisternally, intracapsularly, or intratumorally. In an embodiment, the hybrid Fc fusion G-CSF or a pharmaceutical composition comprising GX-G3 may be administered parenterally or subcutaneously.

The hybrid Fc fusion G-CSF (i.e., G-CSF-hyFc or hyFc-G-CSF) may be formulated with one or more excipients. The active fusion protein may be combined with a pharmaceutically acceptable buffer, and the pH adjusted to provide acceptable stability, and a pH acceptable for administration such as parenteral administration.

According to an embodiment, a formulation for a hybrid Fc fusion G-CSF comprises a buffering agent and/or surfactant and/or stabilizer and/or organic solvent. A liquid formulation according to an embodiment comprises a stable form of hybrid Fc fusion G-CSF comprises (i) a therapeutically effective amount of hybrid Fc fusion G-CSF, (ii) a buffer system, (iii) at least one stabilizer and (iv) at least one surfactant, and (v) optionally propylene glycol as organic solvent, wherein the pH value of the preparation is between 3.8 and 6.5, preferably between 4.0 and 4.6, as described in PCT/TR2018/050208 (WO2019/212429) the entire contents of which are incorporated herein by reference. The invention is further described by the following non-limiting examples.

EXAMPLES

At first, the test product and comparing products used in non-clinical and clinical studies are described.

| | Test Product |
|---|---|
| Name of Active Substance | Recombinant human G-CSF hyFc (Recombinant human Granulocyte colony-stimulating factor hyFc) |
| Code Name | GX-G3 |
| Molecular Weight | 98 kDa |
| Size | Total of 838 amino acids |
| Molecular Formula | $C_{2072}H_{3258}N_{558}O_{630}S_{16}$ |
| Property | Colorless and transparent vial with colorless and transparent liquid |

GX-G3 was prepared by inserting G-CSF-hyFc expressing gene in eukaryotic expression vector of pAD15 into MCS (multi-cloning site). The host cell used for GX-G3 preparation was Chinese Hamster Ovary (CHO) DG44. It is a human G-CSF protein with homodimer structure in a hybridized form of hinge domain of IgD and Fc domain of IgG4. GX-G3 is supplied with stabilized formulation in a disposable injection vial formulation as a sterile, colorless, clear and preservative-free solution.

Comparing Products

A reference product Neutrogin® (Filgrastim) was used as a comparing product. Neutrogin® (JW Pharmaceutical, Co., Ltd) is a glycosylated recombinant human granulocyte colony-stimulating factor. This product is colorless powder in vial (33.6×10⁶ IU (263 mcg) Neutrogin) and solvent in ampoule (1 mL). It was chosen only for non-clinical studies based on the posology of this product which is administered daily during the course of chemotheraphy.

A reference product Neulasta® (Pegfilgrastim) was used as a comparing product. This product is colorless and transparent liquid. Neulasta® (Amgen) was chosen for non-clinical and clinical studies based on the posology of this product which is administered once with 6 mg/0.6 mL dose (a single pre-filled syringe) and recommended for each chemotherapy cycle, given at least 24 hours after cytotoxic chemotherapy. This posology exactly corresponds to the intended posology of the test product.

A. Non-Clinical Studies

Non-clinical studies on efficacy, safety pharmacology and toxicology of GX-G3 are given below;

Example 1

Non-Clinical Study—Efficacy Test: Bioavailability Evaluation in Normal Rats

The objective of this study was to evaluate absorption and bioavailability of GX-G3, when it was intravenously and subcutaneously administered once to normal rats.

In this study, the test article GX-G3 and Neutrogin® were intravenously and subcutaneously injected to rats (240-260 g, approximately 8 weeks age, male) and the blood sample was collected each time. The time interval of blood collection was set as pre-dose (0), 0.08, 0.25, 0.5, 1, 2, 4, 8, 12, 24, 48, 72, 96, 120, 144, 168, and 336 hours for IV and 0.5, 1, 2, 4, 8, 12, 24, 48, 72, 96, 120, 144, 168, and 336 hours dor SC injection. Composition of the study group was represented in Table 1.

TABLE 1

Composition of the study group, dose volume and dose level

| Group | Drug | Route of Administration | Dose (µg/kg) |
|---|---|---|---|
| G1 | Neutrogin ® | IV | 100 |
| G2 | GX-G3 | IV | 100 |
| G3 | GX-G3 | IV | 500 |
| G4 | Neutrogin ® | SC | 100 |
| G5 | GX-G3 | SC | 100 |
| G6 | GX-G3 | SC | 500 |

Figure 2:
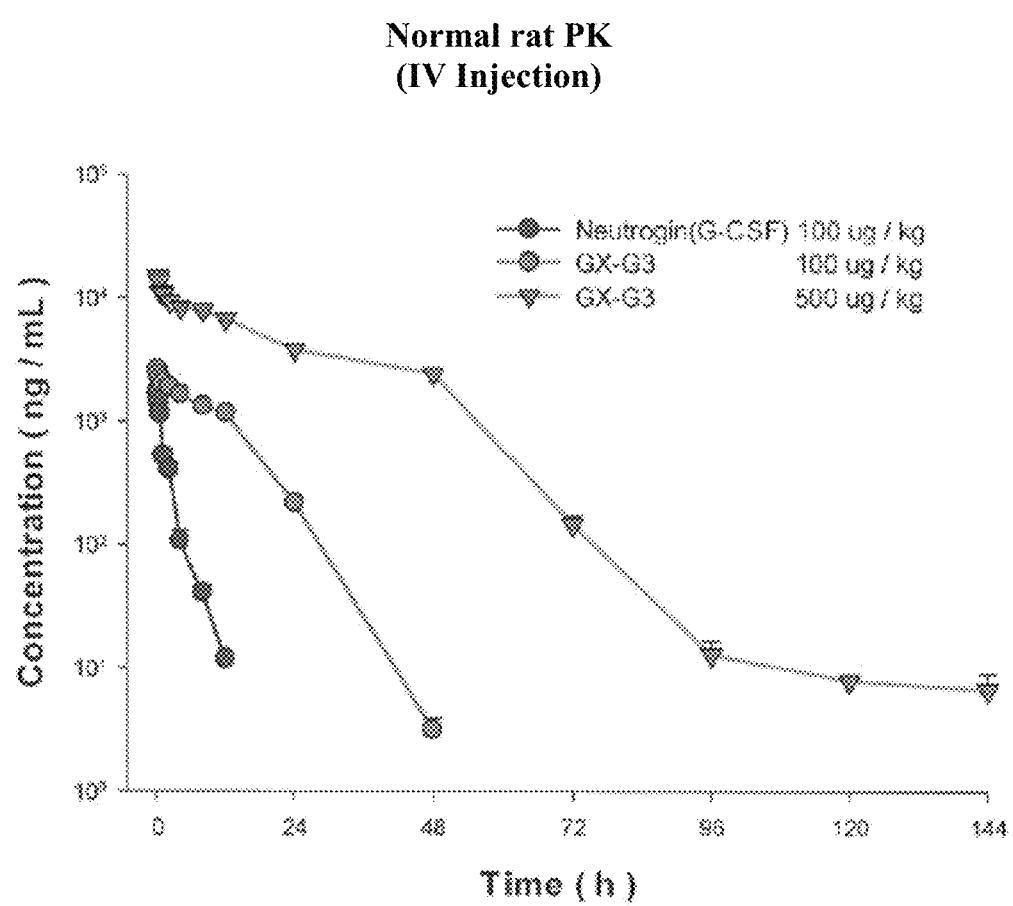
FIG. 2 is a semi-log serum concentration-time profile after IV administration at a dose of 100 μg/kg of Neutrogin®, 100 and 500 μg/kg of GX-G3 to male rats.
Figure 3:
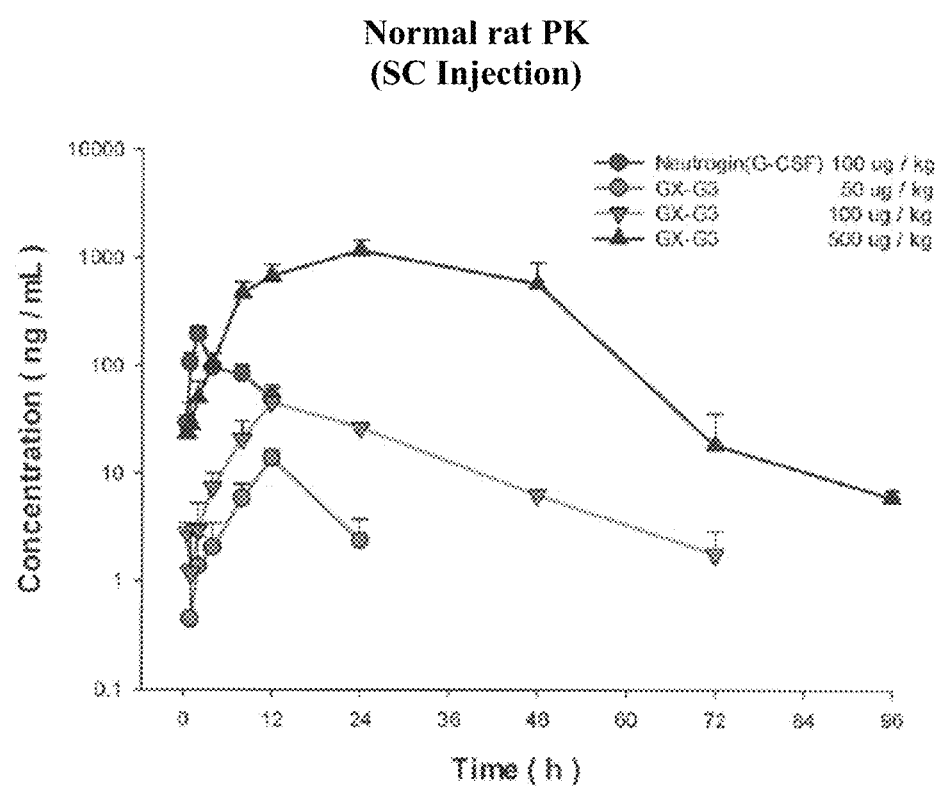
FIG. 3 is a semi-log serum concentration-time profile after SC administration at a dose of 100 μg/kg of Neutrogin®, and 50, 100 and 500 μg/kg of GX-G3 to male rats.

Bioanalysis was conducted with the separated serum and pharmacokinetic parameters were calculated by using Phoenix™ WinNonlin® (ver. 6.0, Pharsight). The pharmacokinetic results of each test group are described in Table 2 and graphs are represented in FIGS. 2 and 3. As a result of the study, it was found that the bioavailability of GX-G3 100 µg/kg was 4% and the bioavailability of GX-G3 500 µg/kg was 16%.

TABLE 2

Pharmacokinetic parameters*

| Group | $AUC_{last}$ (ng*hr/mL) | $C_{max}$ (ng/mL) | $t_{max}$ (hr) | $t_{1/2}$ (hr) |
|---|---|---|---|---|
| G1 | 245.6 ± 11.9 | 169.2 ± 27.5 | 0.08 ± 0.0 | 2.4 ± 0.3 |
| G2 | 2941.4 ± 19.9 | 259.7 ± 159.5 | 0.08 ± 0.0 | 4.2 ± 0.2 |
| G3 | 27155.4 ± 842.9 | 1478.3 ± 24.1 | 0.08 ± 0.0 | 11.8 ± 0.3 |
| G4 | 110.4 ± 8.1 | 19.4 ± 3.2 | 2.0 ± 0 | 6.3 ± 2.5 |
| G5 | 111.5 ± 25.8 | 4.9 ± 1.5 | 14.4 ± 5.4 | 12.5 ± 1.2 |
| G6 | 4287.4 ± 1441.5 | 115.8 ± 28.8 | 24 ± 0.0 | 8.5 ± 0.4 |

*All subjects were represented Mean ± SD

Example 2

Non-Clinical Study—Efficacy Test: Single Dose Subcutaneous Pharmacokinetic Study in Rats The objective of this study was to evaluate pharmacokinetics of GX-G3, when it was subcutaneously administered to neutropenia-induced model rats and normal model rats.

In this study, the test article GX-G3, the comparing articles Neutrogin® and Neulasta® were subcutaneously injected once to neutropenia-induced model rats (240-260 g, approximately 8 weeks age, male) and normal model rats (240-260 g, approximately 8 weeks age, male) and then the blood sample was collected each time. For disease model study group, intraperitoneal administration of cyclophosphamide (CPA) 50 mg/kg/5 mL was conducted at the day before the injection of the drug. The administration dose of the test article was set 100 μg/kg, the same mass as the clinical dose of Neulasta®, the comparing article, 100 μg/kg. To observe additional dose dependency, 25 μg/kg, ¼ dose, was set at the same time. The time interval of blood sampling was set as pre-dose (0), 1, 4, 8, 12, 24, and 36 hours, 2, 3, 4, 5, 6, 7, 11 and 14 days (cross-matching blood samples of 5 animals) for disease model rats; and pre-dose (0), 0.5, 1, 2, 4, 8, 12, 24, and 36 hours, 2, 3, 4, 5, 6, 7, 11 and 14 days for normal model rats. Composition of the study group was represented in Table 3.

TABLE 3

Composition of the study group, dose volume and dose level

| Disease Model | | | Normal Model | |
| --- | --- | --- | --- | --- |
| Group | Drug | Dose (μg/kg) | Group | Drug | Dose (μg/kg) |
| G1 | Neutrogin ® | 100 | G1 | Neutrogin ® | 100 |
| G2 | Neulasta ® | 100 | G2 | Neulasta ® | 100 |
| G3 | GX-G3 | 25 | G3 | GX-G3 | 25 |
| G4 | GX-G3 | 100 | G4 | GX-G3 | 100 |

Figure 4:
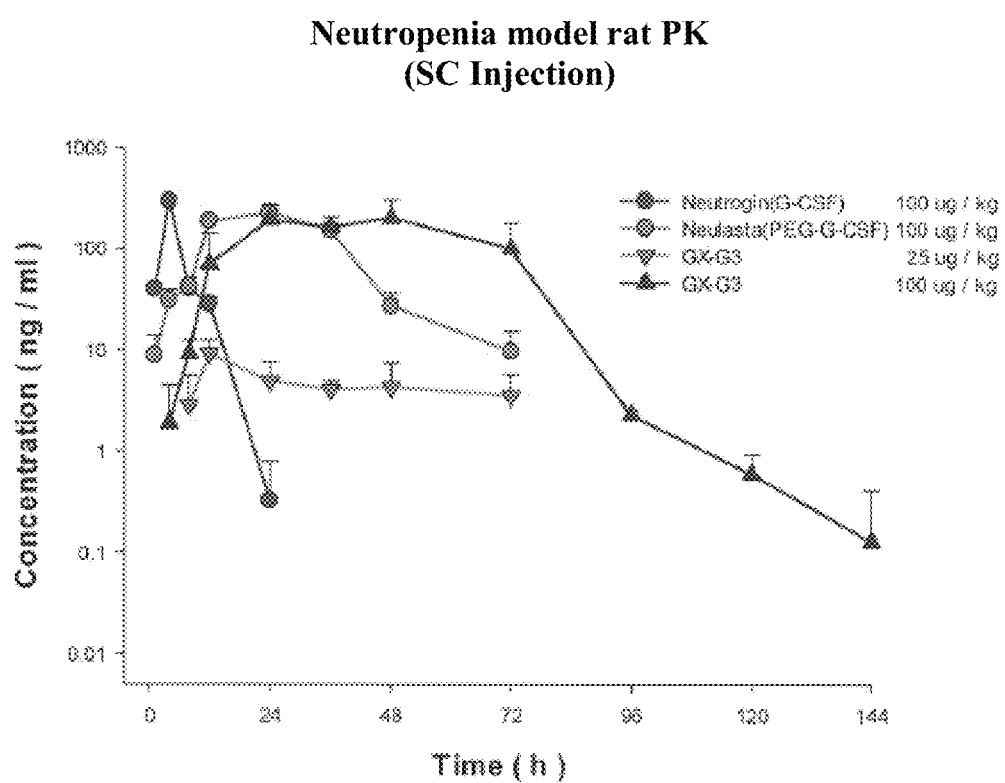
FIG. 4 is a semi-log serum concentration-time profile after SC administration at a dose of 100 μg/kg of Neutrogin® and Neulasta®, 25 and 100 μg/kg of GX-G3 to male neutropenia-induced rats.
Figure 5:
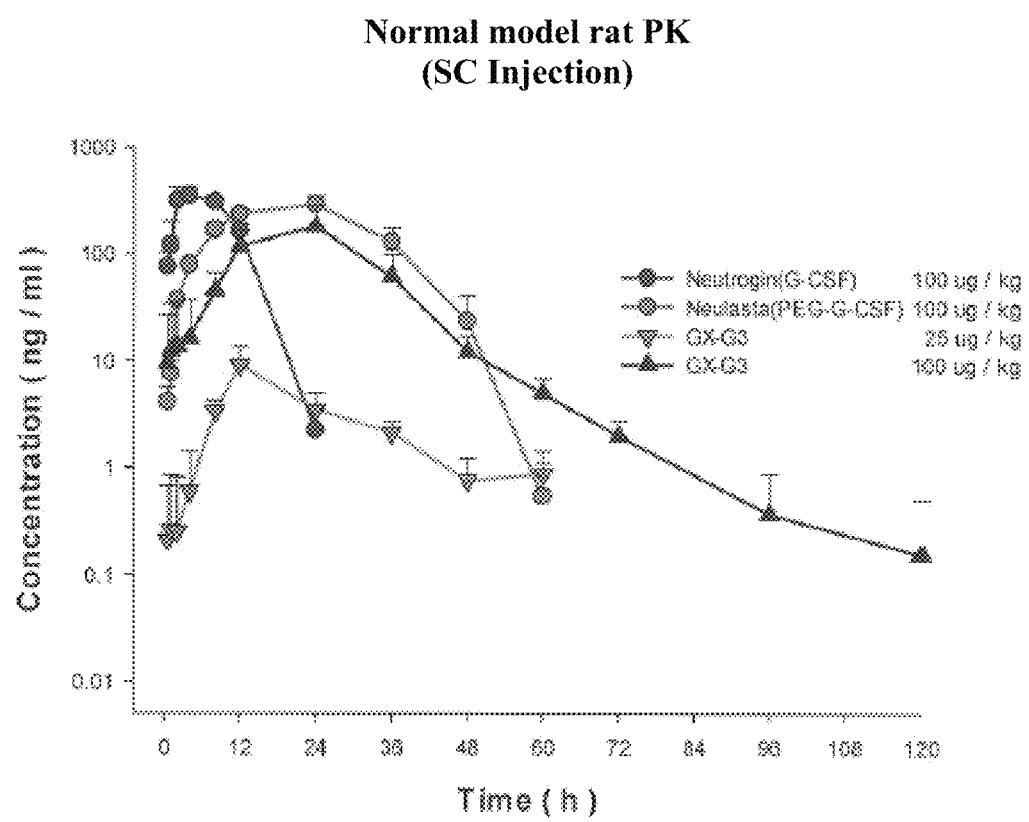
FIG. 5 is a semi-log serum concentration-time profile after SC administration at a dose of 100 μg/kg of Neutrogin® and Neulasta®, 25 and 100 μg/kg of GX-G3 to male normal rats.

Bioanalysis was conducted with the separated serum and pharmacokinetic parameters were calculated by using Phoenix™ WinNonlin® (ver. 6.0, Pharsight). The results of pharmacokinetic values of each test group are described in Table 4 and graphs are represented in FIGS. 4 and 5.

Figure 6:
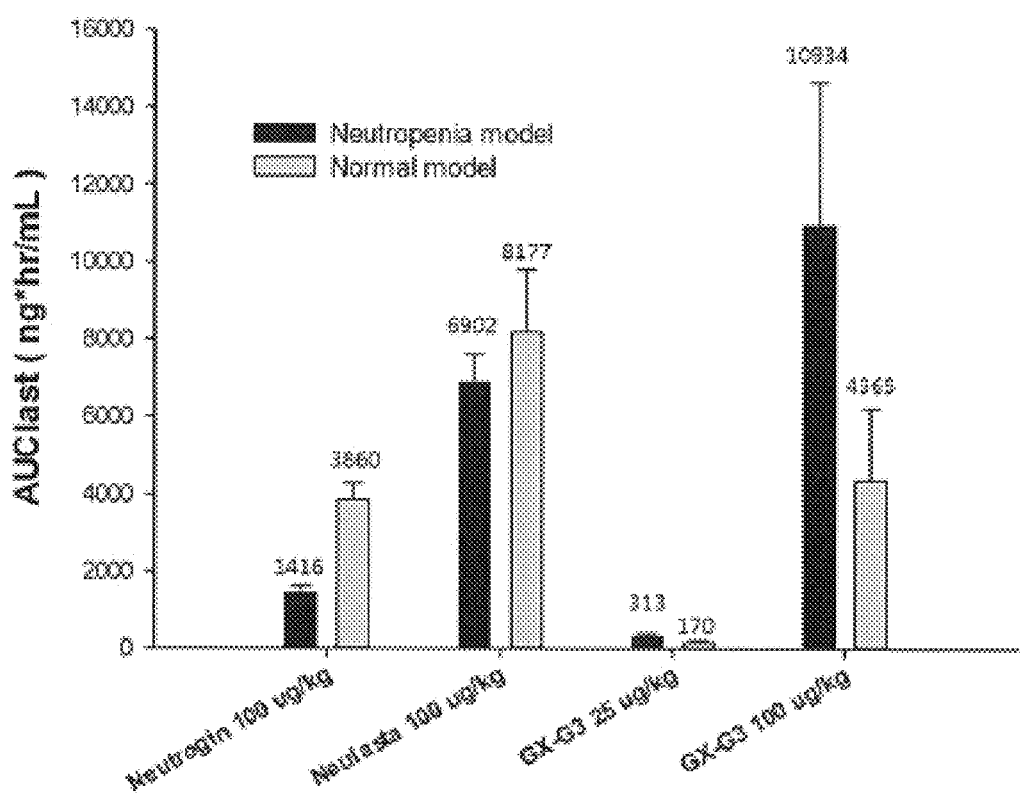
FIG. 6 is $AUC_{last}$ after SC administration at a dose of 100 μg/kg of Neutrogin® and Neulasta®, 25 and 100 μg/kg of GX-G3 to male neutropenia-induced and normal rats.

As a result of the study, $AUC_{last}$ of the test article showed a significant increase in the disease model compared to the normal model as shown in the FIG. 6. The reason for this is inferred that G-CSF receptor mediated clearance action was active in normal rats compared to the disease models. $C_{max}$, $t_{max}$, and $t_{1/2}$ were similar between disease and normal models.

TABLE 4

| | Pharmacokinetic parameters* | | | |
| --- | --- | --- | --- | --- |
| Group | $AUC_{last}$ (ng*hr/mL) | $C_{max}$ (ng/mL) | $t_{max}$ (hr) | $t_{1/2}$ (hr) |
| Disease Model (Neutropenia-induced model) | | | | |
| G1 | 142 ± 20 | 29.6 ± 37.8 | 4.0 ± 0.0 | 2.6 ± 0.2 |
| G2 | 690 ± 72 | 22.5 ± 2.6 | 24.0 ± 0.0 | 9.4 ± 2.6 |
| G3 | 31 ± 9 | 1.0 ± 0.3 | 14.0 ± 7.0 | — |
| G4 | 1093 ± 372 | 21.8 ± 8.0 | 48.0 ± 17.0 | 8.8 ± 3.7 |
| Normal Model | | | | |
| G1 | 386 ± 413 | 37.2 ± 6.1 | 4.0 ± 2.4 | 3.6 ± 1.9 |
| G2 | 818 ± 163 | 29.2 ± 6.0 | 24.0 ± 0.0 | 4.0 ± 1.3 |
| G3 | 17 ± 6 | 0.9 ± 0.5 | 12.0 ± 0.0 | 13.1 ± 3.8 |
| G4 | 436 ± 185 | 18.6 ± 9.8 | 21.6 ± 5.4 | 9.1 ± 3.1 |

*All subjects were represented Mean ± SD

Example 3

Non-Clinical Study—Efficacy Test: Single Dose Subcutaneous and Intravenous Pharmacodynamics Study in Normal Rats The objective of this study was to evaluate pharmacodynamics of GX-G3, when it was subcutaneously and intravenously administered to normal model rats.

In this efficacy study, the test article GX-G3, the comparing articles Neutrogin® and Neulasta® were subcutaneously and intravenously injected once to normal model rats (240-260 g, approximately 8 weeks age, male) and then the hematological levels were used for the evaluation index. In the intravenous injection study, the dose of GX-G3, the test article, was set at the same mass as 100 μg/kg, the clinical dose of Neulasta®. For the subcutaneous injection study, to investigate dose-dependency of GX-G3, it was set up to 12.5, 25, 50, and 100 μg/kg by increasing twice, and the comparing article was set up to 100 μg/kg, the maximum dose. The time interval of blood sampling was set as pre-dose (0), 3, 6, 12, 18, 24, 36, 48, 72, 120, 144, and 168 hours (cross blood sampling by 3 animals) for intravenous injection; and pre-dose (0), 1, 2, 3, 4, 5, 6, 7, 9, 11, and 14 days for subcutaneous injection. Composition of the study group was represented in Table 5.

TABLE 5

Composition of the study group, dose volume and dose level

| Group | Drug | Route of Administration | Dose (μg/kg) |
| --- | --- | --- | --- |
| G1 | GX-G3 buffer | IV | 0 |
| G2 | Neutrogin ® | IV | 100 |
| G3 | Neulasta ® | IV | 100 |
| G4 | GX-G3 | IV | 100 |
| G1 | GX-G3 buffer | SC | 0 |
| G2 | Neutrogin ® | SC | 100 |
| G3 | Neulasta ® | SC | 100 |
| G4 | GX-G3 | SC | 12.5 |
| G5 | GX-G3 | SC | 25 |
| G6 | GX-G3 | SC | 50 |
| G7 | GX-G3 | SC | 100 |

Figure 7:
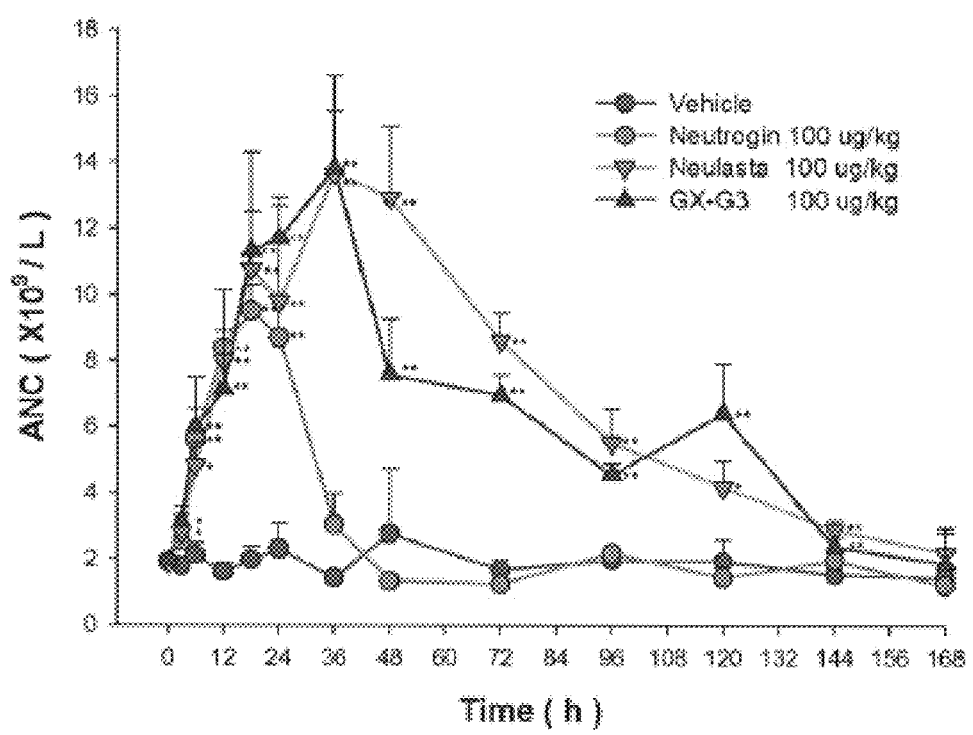
FIG. 7 shows the effects of IV injection of GX-G3, Neutrogin® and Neulasta® on ANC count in normal rats. [Animals were injected intravenously with GX-G3 and Neutrogin®, Neulasta® once a day for 0 day. Each point represents the mean S.D. (n=3). Significantly different from vehicle (*$p<0.05$, **$p<0.01$)]
Figure 8:
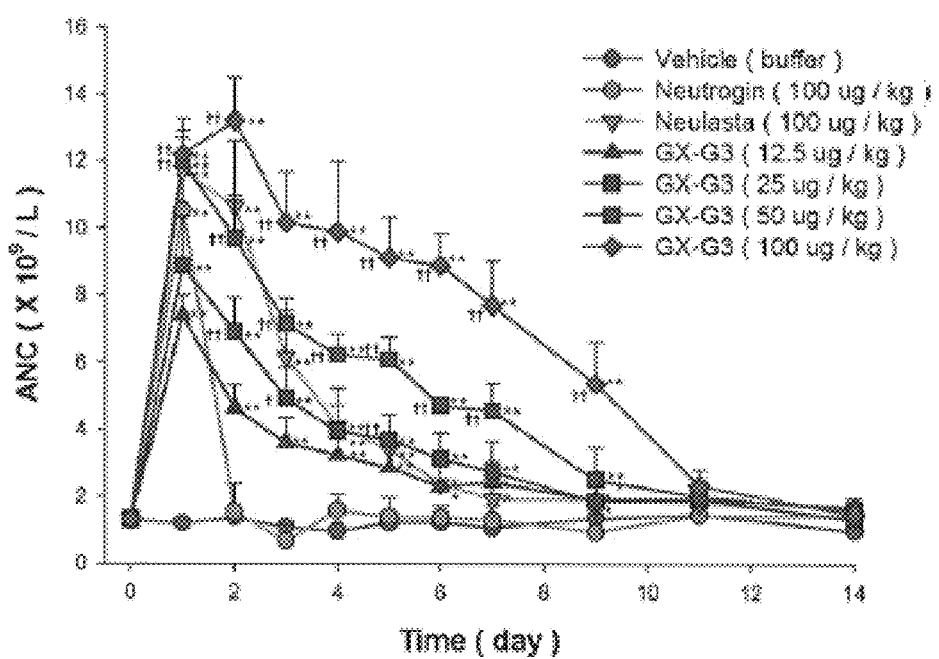
FIG. 8 shows the effects of SC injection of GX-G3, Neutrogin® and Neulasta® on ANC count in normal rats. Animals were injected subcutaneously with GX-G3 and Neutrogin®, Neulasta® once a day for 0 day. Each point represents the mean S.D. (n=5). Significantly different from vehicle (*$p<0.05$, **$p<0.01$).

Bioanalysis was conducted with the separated serum and hematological parameters were calculated by using Phoenix™ WinNonlin® (ver. 6.0, Pharsight). The effects of administration of GX-G3, Neutrogin®, and Neulasta® in rats are described in Table 6 and graphs are represented in FIGS. 7 and 8.

TABLE 6

ANC Curve analysis*

| Group | AUEC$_{last}$ ($10^9$*day/L) | E$_{max}$** ($10^9$/L) | T$_{max}$ (day) |
|---|---|---|---|
| IV Injection | | | |
| G1 | 13.1 ± 2.7 | 3.2 ± 1.6 | 1.1 ± 0.9 |
| G2 | 19.2 ± 1.7 | 9.8 ± 0.5 | 0.8 ± 0.3 |
| G3 | 48.6 ± 2.9 | 14.7 ± 2.6 | 1.7 ± 0.3 |
| G4 | 44.4 ± 1.9*** | 13.9 ± 1.7 | 1.3 ± 0.3 |
| SC Injection | | | |
| G1 | 17.1 ± 1.9 | 1.8 ± 0.4 | 7.0 ± 4.1 |
| G2 | 27.2 ± 3.7 | 10.5 ± 1.0 | 1.0 ± 0.0 |
| G3 | 52.4 ± 5.6 | 11.7 ± 1.2 | 1.0 ± 0.0 |
| G4 | 39.4 ± 4.3 | 7.4 ± 0.6 | 1.0 ± 0.0 |
| G5 | 46.7 ± 6.2 | 8.9 ± 1.5 | 1.0 ± 0.0 |
| G6 | 65.8 ± 4.3 | 12.0 ± 0.7 | 1.0 ± 0.0 |
| G7 | 94.6 ± 7.3**** | 13.2 ± 1.3 | 2.0 ± 0.0 |

*All subjects were represented Mean ± SD.
**E$_{max}$: Maximum effect
Significantly different from G2 (***p < 0.01).
Significantly different from G3 (****p < 0.01)

As a result of the intravenous injections of GX-G3, Neutrogin® and Neulasta® in rats once, the increase of ANC was observed. ANC began to increase from 3 hours after the injection of the test article, showed the maximum value at days 1-2 after the beginning of the injection and then showed a decreasing trend. Also, ANC of all test articles showed significant increases compared to the vehicle group. AUEC$_{last}$ of ANC of GX-G3 showed a significant increase compared to Neutrogin®, and there was no significant difference between GX-G3 and Neulasta®.

As a result of the subcutaneous injections of GX-G3, Neutrogin®, and Neulasta® in rats once, the increase of ANC was observed. From day 1 after the injection of the test article, ANC began to increase, showed the maximum value at days 1-2 after the beginning of the injection and then showed a decreasing trend. Also, ANC of all test articles showed significant increases compared to the vehicle group (G1). ANC of the GX-G3 12.5, 25, 50 and 100 μg/kg showed dose-dependent increase compared to the vehicle group. In the GX-G3, Neutrogin® and Neulasta® 100 μg/kg, which were injected with the same mass, AUEC$_{last}$ of ANC of GX-G3 showed a significant increase compared to Neutrogin® and Neulasta®.

When the results were considered together, the hematological levels of GX-G3 in intravenous and subcutaneous injections showed significant increases in normal model rats, compared to the vehicle group and Neutrogin®, and only subcutaneous injection group showed a significant increase compared to Neulasta®.

As a result of the study, conducting intravenous injection of GX-G3 showed approximately 2.3 times greater effect than Neutrogin®, and showed effect of 0.9 times of equivalent level with Neulasta®. As a result of conducting subcutaneous injection, the dose-dependent reaction of GX-G3 was identified, and it was found that GX-G3 showed approximately 3.5 times greater effect than Neutrogin® and 1.8 times greater effect than Neulasta®, in the same mass.

Example 4

Non-Clinical Study—Efficacy Test: Single Dose Subcutaneous Pharmacodynamics Study in Chemotherapy Induced Neutropenia Rats The objective of this study was to evaluate pharmacodynamics of GX-G3, when it was subcutaneously administered to neutropenia induced model rats.

In this efficacy study, the test article GX-G3, the comparing articles Neutrogin® and Neulasta® were subcutaneously injected once to neutropenia induced rats (240-260 g, approximately 8 weeks age, male) and then the hematological levels were used for the evaluation index. To investigate dose-dependency of GX-G3 in disease model, it was set up to 25, 50, and 100 μg/kg by increasing twice, and the maximum dose was set up equally to the dose of the expected clinical dose of Neulasta®, the comparing drug. For neutropenia induced modelling group, intraperitoneal administration of cyclophosphamide (CPA) 80 mg/kg/5 mL was conducted at the day before the injection of the drug. The time interval of blood sampling was set as pre-dose (0), 1, 2, 3, 4, 5, 6, 7, 9, 11, and 14 days after the administration of CPA. Composition of the study group was represented in Table 7.

TABLE 7

Composition of the study group, dose volume and dose level

| Group | Drug | Dose (μg/kg) |
|---|---|---|
| G1 | Control (Non-treat) | — |
| G2 | GX-G3 buffer | 0 |
| G3 | Neutrogin® | 100 |
| G4 | Neulasta® | 100 |
| G5 | GX-G3 | 25 |
| G6 | GX-G3 | 50 |
| G7 | GX-G3 | 100 |

Figure 9:
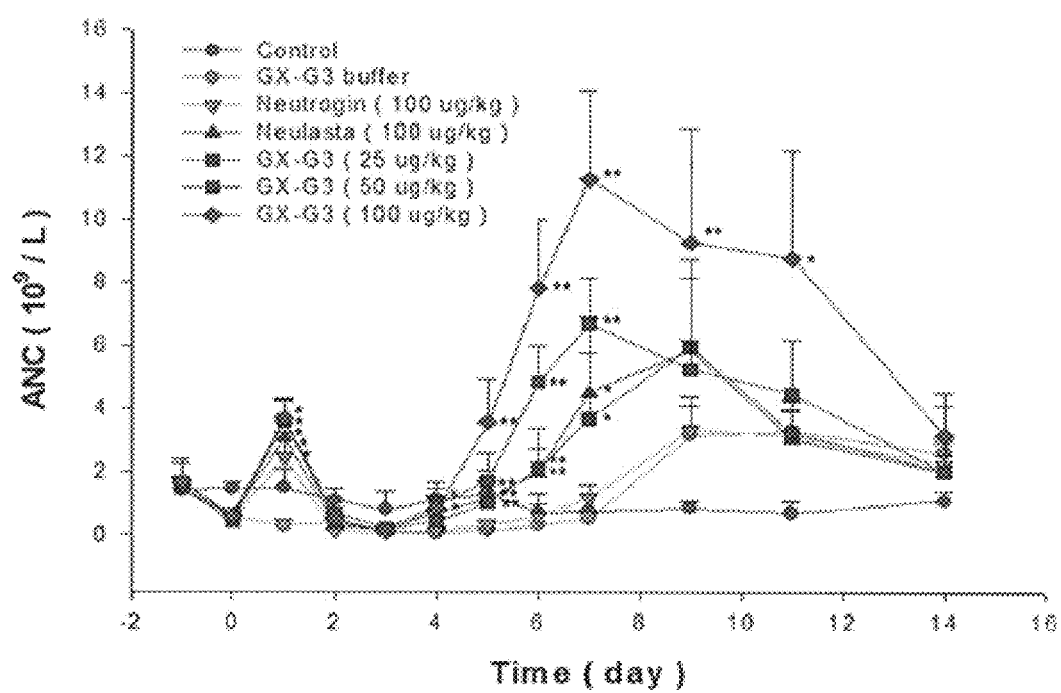
FIG. 9 shows the effects of GX-G3, Neutrogin® and Neulasta® on ANC in Neutropenia rats. Animals were injected subcutaneous with GX-G3 and Neutrogin® Neulasta® once a day for 0 day. Each point represents the mean S.D. (n=5). Significantly different from vehicle (*$p<0.05$, **$p<0.01$).

Analysis of hematological levels was conducted by using Phoenix™ WinNonlin® (ver. 6.0, Pharsight). The effects of administration of GX-G3, Neutrogin®, and Neulasta® in neutropenia rats are described in Table 8 and graph is represented in FIG. 9.

TABLE 8

ANC (Absolute Neutrophil Count) Curve Analysis*

| Group | AUEC$_{last}$ ($10^9$*day/L) | E$_{max}$ ($10^9$/L) | t$_{max}$ (day) | Duration of Neutropenia (DN) (day) |
|---|---|---|---|---|
| G1 | 13.6 ± 3.2 | 2.2 ± 0.8 | 4.2 ± 5.8 | — |
| G2 | 20.9 ± 3.3 | 4.2 ± 1.0 | 10.8 ± 2.0 | 8.7 ± 0.4 |
| G3 | 23.6 ± 3.5 | 3.6 ± 0.8 | 8.2 ± 4.1 | 5.9 ± 0.5 |
| G4 | 36.8 ± 9.8 | 6.0 ± 2.7 | 7.0 ± 3.5 | 3.9 ± 0.8 |
| G5 | 36.5 ± 9.8 | 6.2 ± 2.0 | 7.0 ± 3.5 | 4.1 ± 1.0 |
| G6 | 47.0 ± 7.1 | 6.9 ± 1.1 | 7.8 ± 1.8 | 3.0 ± 0.3 |
| G7 | 78.9 ± 19.7 | 12.0 ± 3.0 | 8.6 ± 2.2 | 2.6 ± 0.4 |

*All subjects were represented Mean ± SD.

As a result of intraperitoneally injecting cyclophosphamide (CPA) 80 mg/kg once, as shown in vehicle group (G2) in FIG. 9, they were identified to be ANC rats. At day 1 after the CPA injection, GX-G3, Neutrogin® and Neulasta® were injected once, and increases of ANC began to show at day 5 after the beginning of the injection (day 5 of the CPA injection). GX-G3, Neutrogin® and Neulasta® showed the maximum value at Days 7-9 after the injection and then showed a decreasing pattern.

The ANC at all doses of GX-G3, Neutrogin® and Neulasta® showed significant increases 2 days after the CPA injection compared to the vehicle group, and the increased ANC were normalized at days 11-14.

$AUEC_{last}$ on ANC curve of the GX-G3 100 µg/kg group showed approximately 3.3 times greater effect than Neutrogin® group with the same mass and approximately 2.1 times greater effect than Neulasta® group. The $AUEC_{last}$ of GX-G3 ANC at GX-G3 25, 50 and 100 µg/kg increased in a dose-dependent manner. The $AUEC_{last}$ and $E_{max}$ of ANC for Neulasta® 100 µg/kg showed equivalent effect at GX-G3 25 µg/kg (about one time), and the recovery period for neutropenia showed a similar period at GX-G3 25 µg/kg.

As a result of observing for 2 weeks after single subcutaneous injection of GX-G3, Neutrogin® and Neulasta®, the hematological levels of GX-G3 (ANC) showed a significant increase in neutropenia rats induced by CPA, compared to the vehicle group, and showed about 3.3 times and 2.1 times greater efficacy ($AUC_{last}$ and ANC curve) compared to the same masses of Neutrogin® and Neulasta® as well as about 1 time equivalent effect compared to ¼ dose (25 µg/kg). In the same mass, duration of neutropenia of GX-G3 showed about 3.3 days of reduction effect compared to that of Neurogin® and 1.3 days of reduction effect compared to Neulasta®.

Example 5

Non-Clinical Study—Safety Pharmacology: Effects on Cloned hERG Channel Current Expressed in CHO Cells The objective of this study was to assess the potential effect of GX-G3 about cardiac repolarization using the hERG current assay on cloned hERG channel expressed in CHO cells using whole-cell patch clamp method. The study was performed in order to evaluate the potential of the test articles for long QT syndrome.

After stabilizing the hERG current, the run-down rate was recorded during the 0.3% GX-G3 formulation buffer (v/v) in normal Tyrode solution (vehicle control) and GX-G3 were perfused for 5 minutes. When vehicle control was perfused, the hERG current was inhibited to approximately 2.7% and when concentrations of GX-G3 at 6 µg/mL, 30 µg/mL and 60 µg/mL was perfused, the hERG current were inhibited to approximately 1.5, 4.6 and 2.4% respectively. Compared with run-down rate of vehicle control, GX-G3 was not statistically significant at all groups. Under identical conditions, the hERG channel current of positive control, E-4031 (100 nM) was inhibited by 79.4% in 4 cells.

Therefore, GX-G3 was no statistically significant differences in the inhibition of hERG channel current up to 60 µg/mL. Effects of vehicle control, GX-G3 and E-4031 (positive control) on cloned hERG channels expressed in Chinese Hamster Ovary (CHO) cells are represented at Table 9.

TABLE 9

Evaluation of the effects of vehicle control, GX-G3 and E-4031 (positive control) on cloned hERG channels expressed in Chinese Hamster Ovary (CHO) cells

| Concentration | Suppression rate (%) Mean | SEM*** | N |
|---|---|---|---|
| Vehicle control* | 2.7 | 1.2 | 3 |
| 6 µg/mL GX-G3 | 1.5 | 1.3 | 3 |
| 30 µg/mL GX-G3 | 4.6 | 3.3 | 3 |
| 60 µg/mL GX-G3 | 2.4 | 1.1 | 3 |
| Positive control** | 79.4**** | 2.6 | 4 |

*Vehicle control: 0.3% GX-G3 formualtion buffer in Normal Tyrode solution.
**Positive control: E-4031 100 nM.
***SEM: Standard error of the mean.
****Significance at $p < 0.01$, vehicle control vs E-4031, student t-test Example 6

Non-Clinical Study—Safety Pharmacology: Neurobehavior (Modified Irwin's Test) and Body Temperature Study in Rats The objective of this study was to evaluate the effects of GX-G3 on neurobehavior (modified Irwin's test) and body temperature in rats after dose of GX-G3.

In this study, GX-G3 was evaluated for the potential to produce alterations in neurobehavioral funstion (locomotion, tail elevation, tremors, convulsion, abdominal tone, catalepsy, traction, righting, reflex, pinna reflex, piloerection, skin coloration, respration rate, eyelid, exophthalmos, lacrimation, salivation, diarrhea, death and startle reflex) and body temperature in rats. Rats (240-260 g, approximately 8 weeks age) were received dose of GX-G3 at dose levels of 0 (vehicle), 1, 3 and 10 mg/kg by subcutaneous administration respectively. Neurobehavioral observations and body temperature measurements were recorded prior to dosing and at 2, 4, 8, 24 and 48 hours after dosing.

Any significant changes on neurobehavioral function on both males and females were observed up to 10 mg/kg single subcutaneous dose of GX-G3.

Body temperature was increased at 1 mg/kg treated group compared to vehicle control group at 2 and 4 hours time points in male rats (2 hours: 38.1±0.3° C. to 38.5±0.2° C., 4 hours: 37.8±0.2° C. to 38.3±0.2° C.). However, this increase was not considered test article related because this change of body temperature is within the range of individual variation of the vehicle control group (37.5-38.8° C.) and it was not dose-dependent. Other treated groups had no changes in body temperature compared to vehicle control group at all time points.

In conclusion, subcutaneous administration of GX-G3 did not produce effects on neurobehavioral function and body temperature up to 10 mg/kg in rats.

Example 7

Non-Clinical Study—Safety Pharmacology: Respiratory Function Study in Rats Following a Single Subcutaneous Administration The objective of this study was to evaluate the effect of GX-G3 on respiration rate, tidal volume and minute volume in rats after a single subcutaneous dose of GX-G3.

Rats (240-260 g, approximately 8 weeks age, male) were received dose of GX-G3 at dose levels of 0 (vehicle), 1, 3 and 10 mg/kg by subcutaneous administration respectively. Respiratory function parameters were recorded prior to dosing and at 2, 4, 8, 24 and 48 hours after dosing.

Single subcutaneous dose of GX-G3 did not produce any significant changes on respiration rate, tidal volume and minute volume at any time points up to 10 mg/kg tested group. In conclusion, single subcutaneous administration of GX-G3 did not produce effects on respiratory function up to 10 mg/kg in rats.

Example 8

Non-Clinical Study—Safety Pharmacology: Effects of Single Subcutaneous Administration on the Cardiovascular System in Male Cynomolgus Monkey using Telemetry The objective of this study was to observe and investigate the effect of subcutaneous dose of GX-G3 on the cardiovascular system (blood pressure, heart rate and electrocardiogram, ECG) in male cynomolgus monkey using telemetry.

GX-G3 was single subcutaneously administered to male cynonolgus monkeys at dose levels of 0 (vehicle), 1 and 3 mg/kg to investigate the safety pharmacological effect on the cardiovascular system. 3 days after of vehicle control (V.C) administration, 1 mg/kg (T1) was administered to the same animal. After confirming the neutrophil normalization in hematological analysis with 21 days of washout interval, 3 mg/kg (T2) was administered to the animal. Then, blood pressure, heart rate and ECG were measured using telemetry at pre-administration and 2, 6, 24, 72 hours (3 days), 168 hours (7 days) and 312 hours (13 days) after administration.

After GX-G3 administration, Neutrophil change was represented in Table 10 and 11. According to results, no significant changes in systolic, diastolic, mean blood pressure and also heart rate were observed at each measuring time in all dosing groups, compared to the vehicle control group. No significant change changes in PR, QRS, RR, QT and QTcF interval were found at each measuring time in any other dosing groups, compared to the vehicle control group. In ECG waveform analysis, there was no abnormal ECG waveform such as arrhythmia in any groups. In clinical sign observation, there was no clinical sign which affect to cardiovascular assessment in administration group including vehicle control group.

As a result of hematological analysis, neutrophil was increased and recovered to same level of pre-administration at 20 days after administration. Considering these results, there was no pharmacological effect on cardiovascular functions including blood pressure, heart rate and ECG waveform due to the single subcutaneous administration of GX-G3 in a volume of below 3 mg/kg in male cynomolgus monkey.

TABLE 10

| | | Neutrophil change after administration of 1 mg/kg GX-G3 | | | |
|---|---|---|---|---|---|
| | V.C. | T1 (1 mg/kg, administration on Day 4) | | | |
| No. | Day 2 (1 day after V.C. dosing) | Day 7 (3 days after T1 dosing) | Day 11 (7 days after T1 dosing) | Day 17 (13 days after T1 dosing) | Day 24 (20 days after T1 dosing) |
| 1 | 7.97 (baseline) | 60.70 (×7.62)* | 41.29 (×5.18) | 21.24 (×2.66) | 3.62 (×0.45) |
| 2 | 6.61 (baseline) | 41.46 (×6.27) | 59.87 (×9.06) | 19.09 (×2.89) | 6.17 (×0.93) |
| 3 | 4.31 (baseline) | 31.33 (×7.27) | 16.32 (×3.79) | 11.30 (×2.62) | 4.02 (×0.93) |
| 4 | 4.82 (baseline) | 68.84 (×14.28) | 48.49 (×10.06) | 20.88 (×4.33) | 7.87 (×1.63) |

*multiple of the baseline

TABLE 11

| | | Neutrophil change after administration of 3 mg/kg GX-G3 | | | |
|---|---|---|---|---|---|
| | V.C. | T2 (3 mg/kg, administration on Day 25) | | | |
| No. | Day 2 (1 day after V.C. dosing) | Day 28 (3 days after T2 dosing) | Day 32 (7 days after T2 dosing) | Day 38 (13 days after T2 dosing) | Day 45 (20 days after T2 dosing) |
| 1 | 7.97 (baseline) | 42.67 (×5.35)* | 6.42 (×0.81) | 2.20 (×0.28) | 3.37 (×0.42) |
| 2 | 6.61 (baseline) | 110.70 (×16.75) | 61.29 (×9.27) | 21.18 (×3.20) | 4.92 (×0.74) |
| 3 | 4.31 (baseline) | 69.72 (×16.18) | 23.14 (×5.37) | 15.92 (×3.69) | 5.77 (×1.34) |
| 4 | 4.82 (baseline) | 132.20 (×27.43) | 70.88 (×14.71) | 33.51 (×6.95) | 9.60 (×1.99) |

*multiple of the baseline

All studies about the safety pharmacological tests indicate that administration of GX-G3 does not have a significant effect on safety-related parameters. Safety pharmacology studies (Example 5-9) were summarized in FIG. 10.

Example 9

Non-Clinical Study—Toxicology Study: Single Dose Subcutaneous Toxicity Study in Rats The objective of this study was to evaluate the acute toxicity after single administration of GX-G3 by subcutaneous to rats. To investigate the acute toxicity of GX-G3 after single subcutaneous administration, Sprague-Dawley rats (240-260 g, approximately 8 weeks age) were single administered at 0 (vehicle), 1, 3 and 10 mg/kg and necropsied after 15 days observation period following end of dosing. During the study, mortality, clinical observations, body weight (BW) measurement and macroscopic observations were conducted.

The results of single subcutaneous administration of GX-G3 showed that no test article-related abnormalities in mortality, clinical observations and body weight changes were observed. At necropsy, test article-related spleen enlargement was observed in 1 male at each 1 and 3 mg/kg, and in all males at 10 mg/kg; but these changes were considered as pharmacokinetic effects. Therefore, the approximate lethal dose (ALD) was considered to be over 10 mg/kg in both sexes in this study.

Example 10

Non-Clinical Study—Toxicology Study: 2-Week Subcutaneous Repeated Dose Range Finding (DRF) Study in Rats The objective of this study was to investigate the potential toxicity of GX-G3, after 2 weeks of subcutaneous administration in rats and suggest an appropriate dose ranges in 4-week toxicology study.

To establish the dose ranges for 4-week repeated dose toxicity study by investigation of the 2-week repeated subcutaneous administration of GX-G3, rats (240-260 g, approximately 8 weeks age) were subcutaneously administered at 0 (vehicle), 1, 3 and 5 mg/kg every two days for 2 weeks (total 7 times). Mortality, clinical observations, body weight measurement, food consumption measurement, ophthalmic examination, urinalysis/urine chemistry, hematology, clinical chemistry, macroscopic observations, organ weight measurement and microscopic observations were conducted.

The results of repeated subcutaneous administration of GX-G3 to rats every two days for 2 weeks at dose levels of 0, 1, 3 and 5 mg/kg (total 7 times) showed that test article-related changes in mortality, body weight, food consumption, ophthalmic examination and urinalysis/urine chemistry were not observed. Increased hematopoietic effect in the spleen and hindlimb were considered pharmacological action by test article. Bone resorption/osteogenesis, subcutaneous edema in the hindlimb and related increased ALP and hindlimb swelling (at necropsy) which were observed in 2 females at 5 mg/kg were test article-related adverse effect.

Therefore the highest dose for over 4-week repeated dose toxicity study was considered to be under 3 mg/kg when administered every two days, and under 10 mg/kg when administered once weekly.

Example 11

Non-Clinical Study—Toxicology Study: 2-Week Subcutaneous Repeated Dose Range Finding (DRF) Study in Cynomolgus Monkeys The objective of this study was to investigate the potential toxicity of GX-G3, after 2 weeks of subcutaneous administration in cynomolgus monkeys and suggest an appropriate dose ranges in 4-week toxicology study. To establish the dose ranges for 4-week repeated dose toxicity study by investigation of the 2-week repeated subcutaneous administration of GX-G3, cynomolgus monkeys (3010-4237 g in males and 2571-3373 g in females, approximately 4 years age) were administered by subcutaneous injection at dose levels of 0 (vehicle), 1, 5 and 10 mg/kg every two days for 2 weeks (total 7 times). Mortalities, clinical observations, body weight measurement, food consumption measurement, ophthalmic examination, urinalysis/urine chemistry, hematology, clinical chemistry, macroscopic observation and organ weight measurement were conducted.

The results of repeated subcutaneous administration of GX-G3 to cynomolgus monkeys showed that test article-related changes in mortality, body weight changes, ophthalmic examination and urinalysis/urine chemistry were not observed. Test article-related swollen, skin discoloration or skin discharge was observed, and decreased food consumption was observed in females at 10 mg/kg. White blood cell count, especially neutrophil was prominently increased, and red blood cell count, hemoglobin, hematocrit and platelet count were prominently decreased at 5 mg/kg. Also alkaline phosphatase (ALP) and gamma glutamyl transpeptidase (GGT) were increased and glucose (GLU) (except in females at 10 mg/kg) was decreased in both sexes at all treatment groups. In organ weight measurement, spleen weight at 5 mg/kg was prominently increased corresponding with enlarged spleen in macroscopic observation. These changes were considered as test article-related pharmacological effects. Therefore, the highest dose for over 4-week repeat dose toxicity study was considered as under 5 mg/kg when administered every two days, and under 10 mg/kg when administered once weekly.

Example 12

Non-Clinical Study—Toxicology Study: 4-Week Subcutaneous Repeated Dose Toxicity and Toxicokinetic Study of GX-G3 in Rats with a 4-Week Recovery Period The objective of this study was to investigate the toxicity and toxicokinetics profiles of GX-G3 following 4 weeks of repeated subcutaneous injection to rats. The reversibility of treatment with GX-G3 was evaluated in rats for 4 weeks of recovery.

To investigate the toxicity and toxicokinetics profiles which were observed after repeat subcutaneous dosing of GX-G3 for 4 weeks and to evaluate the reversibility during 4 weeks of recovery period, GX-G3 was administered to Sprague-Dawley rats (184.5-226.1 g in males and 99.0-120.1 g in females, approximately 5 weeks age) at 0, 1, 3 and 10 mg/kg (10 or 15 males and females in each group) once weekly for 4 weeks (total 4 doses) and rats were assigned to 4 weeks of recovery after completion of treatment. Throughout the study, mortality, clinical signs and detailed clinical signs, body weight measurement, food consumption, ophthalmology, urinalysis/urine chemistry, hematology, coagulation, clinical chemistry, organ weight measurement, macro- and microscopic examinations, and toxicokinetics and immunogenicity analyses were performed.

According to the results of repeated subcutaneous administration of GX-G3, no test article-related abnormal changes were observed in mortality, ophthalmology and urinalysis/urine chemistry after 4 weeks of GX-G3 treatment which was subcutaneously injected (total 4 doses) and 4 weeks of recovery period. During the treatment period, abnormal gait and swollen of hindlimb were observed in both sexes at mg/kg, and decreased weight gain which was continued to recovery period was observed in females at high dose group. In the hematology and microscopic examination, pharmacologic effects were related to hematopoiesis was observed. In the clinical chemistry, increased alkaline phosphatase (ALP) was correlated with the result of microscopic examinations including synovial proliferation, edema of subcutaneous/synovium, cellular infiltration of synovium/muscle and moderate osteogenesis/bone resorption, and this was considered test article-related adverse effect. Since these changes were observed in both sexes at mg/kg and some changes did not recovered after completion of recovery period, the No Observed Adverse Effect Level (NOAEL) in both sexes is considered as 1 mg/kg.

Example 13

Non-Clinical Study—Toxicology Study: 4-Week Subcutaneous Repeated Dose Toxicity and Toxicokinetic Study in Cynomolgus Monkeys with a 4-Week Recovery Period The objective of this study was to investigate the toxicity and toxicokinetics profiles of GX-G3 following 4 weeks of repeated subcutaneous injection to monkeys. The reversibility of treatment with GX-G3 was evaluated in monkeys for 4 weeks of recovery.

To investigate the toxicity and toxicokinetics profiles which were observed after repeat subcutaneous dosing of GX-G3 for 4 weeks and to evaluate the reversibility during 4 weeks of recovery period, GX-G3 was administered to cynomolgus monkeys (2310-3009 g in males and 2199-2704 g in females, approximately 3 years age) at 0 (vehicle control), 1, 3 and 10 mg/kg once weekly for 4 weeks (total 4 doses). The reversibility of any effects of treatment with GX-G3 was evaluated in a subset of monkeys assigned to 4 weeks of recovery after completion of treatment. Throughout the study, mortality, clinical signs, body weight measurement, food consumption, ophthalmology, electrocardiography, urinalysis/urine chemistry, hematology, coagulation, clinical chemistry, organ weight, macro- and microscopic examinations, and toxicokinetics and immunogenicity analysis were performed.

Based on the mortality (moribund sacrificed and found dead animals) in both sexes at 10 mg/kg and microscopic findings in the brain (neuronal necrosis, neurogliosis and pigmented histiocyte), femur/marrow (hyperostosis) and bone marrow (fibrosis) which were observed in both sexes of main and recovery groups, the No Observed Adverse Effect Level (NOAEL) in both sexes is considered as 3 mg/kg.

Example 14

Non-Clinical Study—Toxicology Study: Subcutaneous (SC) Embryofetal Developmental Toxicity Study in the Rat The objective of this study was to investigate the potential maternal and developmental toxicity of GX-G3 when administered subcutaneously (SC) to presumed pregnant Sprague Dawley rats, during the organogenetic period of the species i.e. Gestation Day (GD) 6 through 17. The pregnant rats (220-291 g, approximately 10 weeks age) for each dose-group were treated subcutaneously (SC) at 0 (vehicle), 1, 3 and 5 mg/kg of GX-G3 (volume of administration 1 mL/kg), four times during organogenesis, once every 3 days, on GDs 6, 9, 12 and 15. All females were observed daily for general status, course of pregnancy, clinical signs, and mortality. Rats were cesarean sectioned on GD 20 and the following parameters were recorded: intact uterus weight, number of corpora lutea and implantations, number of live fetuses and embryofetal deaths, fetal sex, fetal and placental weights.

According to GX-G3 administered subcutaneously to pregnant rats, once every 3 days during the organogenetic period, on GDs 6, 9, 12 and 15 at 0 (vehicle), 1, 3 and 5 mg/kg was well tolerated by pregnant animals at all doses tested. Swollen hind-limbs and enlarged spleen were expected findings, as they had already been observed in previous toxicology studies with GX-G3.

No interference with the course of pregnancy was observed. No adverse effects on embryofetal development were noted and no sign of teratogenicity was evidenced at all doses. With the present treatment schedule and duration, 5 mg/kg can be considered the NOAEL for the mother as only pharmacologically related spleen enlargement and swollen hindlimbs, not impacting on normal animal behavior, were seen.

The dose of 5 mg/kg ($AUC_{0-72}$ h after single and repeated administrations of 1990 and 1530 μg·h/mL, respectively) was considered the NOAEL for embryofetal development, based on the presence of the pharmacologically related spleen enlargement.

Example 15

Non-Clinical Study—Toxicology Study: Subcutaneous (SC) Embryofetal Developmental Toxicity Study in the Rabbit The objective of this study was to investigate the potential maternal and developmental toxicity of GX-G3 when administered subcutaneously (SC) to presumed pregnant New Zealand White rabbits, during the organogenetic period of the species i.e. Gestation Day (GD) 6 through 19. The pregnant rabbits (2.75-4.09 kg, approximately 4-5 months age) for each dose-group were treated subcutaneously (SC) at 0 (vehicle, 1 mL/kg), 0.035 mg/kg (0.35 mL/kg), 0.1, 0.3 and 1 mg/kg of GX-G3 (1 mL/kg), five times during organogenesis, once every 3 days, on Gestation Days (GDs) 6, 9, 12, 15 and 18. All females were observed daily for general status, course of pregnancy, clinical signs, and mortality. Rabbits were cesarean sectioned on GD 29 and the following parameters were recorded: intact uterus weight, number of corpora lutea and implantations, number of live fetuses and embryofetal deaths, fetal sex, fetal and placental weights.

According to GX-G3 administered subcutaneously to pregnant rabbits, once every 3 days during organogenesis, on GDs 6, 9, 12, 15 and 18 at 0 (vehicle), 0.035, 0.1, 0.3 and 1 mg/kg, induced minimal reduction of food consumption and minimally lower body weight gain up to 0.1 mg/kg compared with controls, while these effects were moderate at 0.3 and 1 mg/kg. At 0.3 and 1 mg/kg GX-G3 interfered with maintenance of pregnancy inducing abortions and increase in resorptions.

With the present treatment schedule and duration, the dose of 0.035 mg/kg ($AUC_{last}$ after single administrations of 2.13 μg·h/mL, $C_{max}$ 0.0612 μg/mL; on gestation days 9 and 12, serum C24 values accounted for, respectively, 28 and 24% of C24 values on GD 6; on GD 15 and 18 serum C24 was below the limit of quantification) is considered the NOAEL for the mother, based on minimal effects on body weight and food consumption. Considering the only minimal reduction of fetal body weight, 0.035 mg/kg is also considered the NOAEL for embryofetal development.

Example 16

Non-Clinical Study—Toxicology Study: 26-Week Subcutaneous (SC) Toxicity Study in the Sprague Dawley Rat Followed by an 8-Week Recovery Period The objective of this study was to investigate the potential toxicity of GX-G3 for the treatment of chemotherapy-induced neutropenia, when subcutaneously (SC) administered once a week for twenty-six consecutive weeks to Sprague Dawley rats, and to investigate the reversibility of changes after an eight-week recovery period.

To investigate the toxicity profiles which were observed after repeat subcutaneous dosing of GX-G3 and to evaluate the reversibility of recovery period, GX-G3 was administered to Sprague Dawley rats (205-261 g in males and 173-220 g in females, approximately 6-7 weeks age) as a once-a-week, 26-week repeated subcutaneous administration (twenty-six overall treatments) at doses of 0 (vehicle), 1, 3 and 5 mg/kg. Additional animals of both genders were added to the control and high dose groups, treated with the same schedule and allowed an eight-week recovery period. Animals were observed daily for mortality and clinical signs.

The treatment caused at all doses swelling at the hind-limbs and difficulties in the locomotion, with more severe effects in males. Animals affected by limb changes showed also, as a secondary effect, body weight loss, reduced food consumption and sometimes ruffled fur, decreased activity, seldom dyspnea and chromodacryorrhea. As a consequence, one low-dosed male was sacrificed due to the severity of the clinical picture.

Histological examination showed several findings consistent with morphological indicators and consequences of an exaggerated increase of myelopoiesis and the related embolism, correlating with the increases in neutrophils and lymphocytes noted at hematological determinations. Under the applied experimental conditions, based on the necrotic lesions noted in the mid and high dose groups, the NOAEL (No Observed Adverse Effect Level) for the test item can be identified at 1 mg/kg.

Example 17

Non-Clinical Study—Toxicology Study: 26-Week Subcutaneous (SC) Toxicity Study in the Cynomolgus Monkey Followed by an 8-Week Recovery Period The objective of this study was to investigate the potential toxicity of GX-G3 for the treatment of chemotherapy-induced neutropenia, when subcutaneously (SC) administered once a week for twenty-six weeks to cynomolgus monkeys, and to investigate the reversibility of changes, if any, after eight-week recovery period. Due to the findings observed at the mid and top dose after the second dosing and the mortality at the top dose, the dosing schedule (Days for new dosing: 1, 8, 22, 36, 50, 64, 78, 92, 106, 120, 134, 148, 162, 176) was changed to once every second week.

Groups of cynomolgus monkeys (2-4 kg weight, approximately 2.5-3 years age) were given the control vehicle (0), 1, 3 or 5 mg/kg of GX-G3, additional animals in the control and high dose group were included in the study to investigate the reversibility of changes, if any, after eight-week recovery period. Clinical signs were checked daily.

Mortality occurred at the highest dose within Day 17 (after dosing on Day 1 and 8) due to an exaggerated increased myelopoiesis with a severe increase in circulating blood cells with the formation of emboli composed of granulocytes in several organs. At lower dosages only effects related to the pharmacological activity of the test item were found and the dose of 3 mg/kg every second week for 26 weeks is considered the NOAEL.

According to results of toxicology and toxicokinetic studies (Example 9-17), NOAEL of GX-G3 was evaluated as 1 mg/kg for rodents (rats) and 3 mg/kg for non-rodents (cynomolgus monkeys). This determined dose of NOAEL is lower than that of Pegfilgrastim NOAEL, the second generation G-CSF. The dose of Pegfilgrastim NOAEL in monkeys is 750 µg/kg (*FDA-Non-Clinical-Review (s)* 2018). The toxicology and toxicokinetic studies (Example 9-17) studies were summarized in FIG. 11.

The data obtained from the in vitro assays or animal studies can be used in formulating a range of dosages for use in humans. Therapeutically effective dosages achieved in one animal model can be converted for use in another animal, including humans, using conversion factors known in the art (Freireich et al., *Cancer Chemother. Reports,* 1966, 50(4):219-244 and Table 12).

TABLE 12

Equivalent Surface Area Dosage Factors

| | To: | | | | |
|---|---|---|---|---|---|
| From: | Mouse (20 kg) | Rat (150 g) | Monkey (3.5 kg) | Dog (8 kg) | Human (60 kg) |
| Mouse | 1 | ½ | ¼ | ⅙ | 1/12 |
| Rat | 2 | 1 | ½ | ¼ | 1/7 |
| Monkey | 4 | 2 | 1 | ⅗ | ⅓ |
| Dog | 6 | 4 | ⅗ | 1 | ½ |
| Human | 12 | 7 | 3 | 2 | 1 |

After non-clinical studies, the first-in-human clinical trial of GX-G3 Phase I study fully considering the safety and tolerance based on the premise was planned within the range determined 12.5 µg/kg, 25 µg/kg, 50 µg/kg, 100 µg/kg, 200 µg/kg and 400 µg/kg doses of GX-G3 with healthy volunteers.

B. Clinical Studies

Clinical trials of GX-G3 human studies for the present invention are given below;

Example 18

Clinical Study: Phase I

The Phase I Study was performed to investigate the safety, tolerability, and pharmacokinetics/pharmacodynamics of GX-G3 after single subcutaneous administration in healthy male subjects.

i. Objective

For Phase I, the primary objective was to evaluate the tolerance after a single subcutaneous administration of GX-G3 in healthy male subjects.

Secondary objectives were to assess the safety (adverse events, vital signs, physical examination, electrocardiogram, clinical laboratory test, and radiologic test), pharmacokinetics (PK), pharmacodynamics (PD) and PK-PD relationship after a single subcutaneous administration of GX-G3 in healthy adult male subjects and to compare them with the single subcutaneous administration of Neulasta®. Also, another objective was to evaluate immunogenicity after a single subcutaneous administration of GX-G3 in healthy adult male subjects.

ii. Study Design and Plan

This is a dose-block randomized, double-blinded, placebo-controlled, active-controlled, dose-escalation Phase I clinical trial to investigate the safety, tolerability, and pharmacokinetics/pharmacodynamics of GX-G3 after single subcutaneous administration in healthy male subjects. Although it is an exploratory Phase I clinical trial observing the dose-limiting toxicities (DLT), a double-blinded and randomized design is applied to the GX-G3 treatment group and placebo treatment group in order to reduce the bias from the investigators or subjects during the report on adverse effect.

Treatment and observation period for subject is about 6-10 weeks (including immunogenicity test). Subject is screened for history, physical examination, and clinical laboratory test within the past 28 days before the date of administration of the test drug (Day 1). Subject deemed fit for this clinical trial according to the screening is admitted to the clinical trial center and fasted a day before the administration of test drug (Day −1). Each subject is discharged after the completion of all tests on the 5th day (Day 4) and visits the center for 7 times for follow-up.

Tolerance and safety will be observed for 3 weeks after the completion of a single administration in each dose group. The dose will be increased to the next dose when the tolerance and safety evaluation in each dose group is completed from the GX-G3 treatment group. Neulasta®, the same continuous G-CSF formulation, will be selected as an active control group and it will be recruited in parallel with GX-G3 maximum dose group.

Administration and observation period determined in this clinical trial are considered to be appropriate for the evaluation of tolerance, safety, and pharmacokinetic and pharmacodynamic variables.

Therefore, it will be the first-in-human clinical trial fully considering the safety and tolerance based on the premise that GX-G3, which is a granulocyte colony-stimulating factor, of a dose within the range determined in this clinical trial is administered once.

iii. Study Population 8 subjects in each dose group with total of 6 GX-G3 dose groups (6 with test drug+2 with placebo) and 6 subjects in active control group (6 with Neulasta® 6 mg)—total of 54 healthy male subjects were analysed.

For Phase I, subjects were screened based on the following characteristics or parameters:

Inclusion Criteria:
1. A volunteer who decided the participation voluntarily and signed the written consent form after understanding the detailed explanation on this clinical trial.
2. A healthy male older than 20 years old and younger than 45 years old at the time of screening.
3. A subject whose weight is between 60 kg and 94.0 kg, and whose body mass index (BMI) is between 19 kg/m$^2$ and 27 kg/m$^2$.
4. A subject proper for this clinical trial as a result of the screening.

Exclusion Criteria:
1. A person who has a clinically significant disease in hepatobiliary tract system, renal system, nervous system (central or peripheral), respiratory system, endocrine system (diabetes, hyperlipidemia, etc.), cardiovascular system (congestive heart failure, coronary artery disease, myocardial infarction, etc.), hemato-oncology, urinary system, mental, musculoskeletal system, immune system (rheumatoid arthritis, systemic lupus erythematosus, etc.), or otorhinolaryngologic system, or who has a history of above diseases.
2. A person who has white blood cell (WBC) or neutrophil % value exceeding the reference range during the screening period.
3. A person who has platelet level lower than 100,000/mm$^3$ during the screening period.
4. A person who has the maximum length of spleen shown on the upper abdominal ultrasound exceeding 16 cm during the screening.
5. A person who has systolic blood pressure ≥140 mmHg or ≤90 mmHg, or diastolic blood pressure ≥95 mmHg or ≤50 mmHg when the vital sign is measured after sitting and resting for more than 3 minutes.
6. A person who has clinically significant arrhythmia on the electrocardiogram.
7. A person with an active infection or a fever of 38° C. and higher within a week before the administration of the investigational medicinal product.
8. A person who has an evidence of chronic hepatitis B, C or HIV infection
9. A person who has a history of drug and other hypersensitivity reactions.
10. A person who had a hemorrhage more than 400 mL within 8 weeks before the administration of the investigational medicinal product, or who donated blood.
11. A person who smokes more than 10 cigarettes per day on average for the recent 3 months.
12. A person who drinks continuously (more than 21 units/week, 1 unit=10 g of pure alcohol) or who cannot stop drinking from 24 hours before the admission until the discharge.
13. A person who has a history of alcohol and drug abuse within 6 months before the screening.
14. A person who dependently administered psychotropic medication or narcotic analgesic within 6 months before the screening.
15. A person who has psychosis or other central nervous system diseases and is deemed unfit to go through the clinical trial evaluation by the investigator.
16. A person who is deemed unfit to communicate.
17. A subject who does not understand the contents of the clinical trial and is not cooperative (a person who is not willing to visit the investigator as scheduled or to postpone the elective surgery scheduled in advance), and who is deemed unfit to complete the trial by the investigator.
18. A person who is currently participating in a clinical trial or who completed a clinical trial but the 8-week period has not passed yet.
19. When an investigator determines and clearly states that a person is deemed unfit to participate in the clinical trial because of a medical status that can be endangered by the administration of test drug, etc.
20. A person is considered to be inadequate for the participation in the clinical trial by investigator according to other clinical laboratory test results.
21. A person who has a history of G-CSF administration.
22. A person who had an administration of a prescription medicine or an oriental medicine 2 weeks before the administration of the investigational medicinal product, or who had an administration of over-the-counter medicine or a vitamin supplement a week before the administration of the investigational medicinal product Drop-out of subject from the clinical trial, discontinuance of administration of the clinical trial test drug, and premature termination of the clinical trial or closure of the trial center might occur because of personal reasons and/or medical or administrative reasons of subject and such causes are as follows.

Participation in the clinical trial can be stopped at any time when a subject wants and the reason for ending participation does not have to be explained.

Subject should be dropped out from the clinical trial in case of the following situations:

1. When a subject or his legal representative withdraws the consent.
2. When an investigator determines that the continued participation in the clinical trial is harmful to the subject.
3. When an adverse effect is too severe to continue the clinical trial occurs.
4. When the sponsor or investigator determines that it is a serious protocol violation.
5. When a subject wants to stop participating because of other reasons.
6. Serious protocol violations in which the subject must be dropped out from this clinical trial are as follows.
7. When an investigator or sponsor determines that withdrawal from participation in the clinical trial is necessary because of the violation of selection/exclusion criteria, which can distort effectiveness or safety evaluation on test drug seriously or affect the safety of subject.
8. When a subject has been using other medications or surgical treatment on the disease targeted in the clinical trial but an investigator determines that the subject is not willing to stop those treatment methods.
9. Medication, only except the test drug, should not be administered during the clinical trial. However, it can be administered in accordance with the decision of the investigator, if necessary. If a subject takes a drug without the decision of the investigator and the drug is considered to be influential to the safety evaluation in this clinical trial, the subject is dropped out.

iv. Administered Treatment

The results of repeated-dose toxicity study were used to calculate the initial usage and dosage of the GX-G3 in the first-in-human trial. As a result of the preclinical study with repeated subcutaneous administration of GX-G3 for 4 weeks in cynomolgus monkeys, NOAEL observed was 3 mg/kg in both male and female monkeys. In addition, NOAEL observed during the toxicity test with repeated subcutaneous administration for 4 weeks in rats was 1 mg/kg. A dose, which is 2.5-80 times less than the human equivalent dose (HED) that no observable adverse effect level (NOAEL) is changed into weight, is administered in this study. This dose is 4 times less than when the maximum human clinical trial dose of similar drug, Neulasta®, is changed into NOAEL. Therefore, irreversible adverse effects (moribundity, weight loss) observed during the 4 weeks of the repeat-dose toxicity study are less likely to be observed during the process of single administration in the healthy adult male subject.

A dose of GX-G3 for each subject is calculated based on the weight. The single doses per kg (weight) to be administered are 12.5 µg, 25 µg, 50 µg, 100 µg, 200 µg, and 400 µg. For example, a dose for single administration to the 60-kg subject assigned in 25 µg dose group is 1.5 mg (1500 µg; 25 µg/kg/dose×60 kg=1500 µg/dose). Included in a vial is 1 mg or 10 mg of GX-G3 because the concentration of GX-G3, an investigational medicinal product of this clinical trial, is 1 mg/mL or 10 mg/mL per vial and the vial contains 1 mL of drug. Therefore, 0.15 mL of test drug is administered to a subject if 10 mg/mL formulation of test drug should be administered.

Doses for each dose group of the placebo control group are calculated with the same method as in GX-G3 before the administration. Neulasta® 6 mg, which is the common dose, is administered to the active control group. Each dose group is administered with 1-3 doses of test drug or control drug subcutaneously.

v. Methodology

Phase I study is performed gradually from low dose to high dose within 6 dose groups and 8 subjects will be assigned in the first 5 dose groups with the ratio that 6 subjects are assigned with a test drug and 2 subjects are assigned with a placebo. Last dose group of GX-G3 is assigned with the active control drug and 14 subjects are assigned with the ratio of 6 subjects for the test drug, 2 for placebo, and 6 for Neulasta®. Administration of Phase I clinical study is summarized in Table 13.

TABLE 13

| | \multicolumn{6}{c}{Phase I Study - Number of subjects (administered dose)} |
|---|---|---|---|---|---|---|
| | Coh. 1 | Coh. 2 | Coh. 3 | Coh. 4 | Coh. 5 | Coh. 6 |
| Placebo | 2 | 2 | 2 | 2 | 2 | 2 |
| GX-G3 | 6 (12.5 µg/kg) | 6 (25 µg/kg) | 6 (50 µg/kg) | 6 (100 µg/kg) | 6 (200 µg/kg) | 6 (400 µg/kg) |
| Neulasta | — | — | — | — | — | 6 (6 mg) |

*Coh.: Cohort vi. Efficacy and Safety Variables

Primary evaluation purpose of this clinical trial is to evaluate the tolerance after a single subcutaneous administration of an investigational medicinal product, GX-G3, in healthy male volunteers.

Maximum Tolerable Dose (MTD) will be determined through the evaluation of tolerance through the evaluation of occurrence of dose-limiting toxicities (DLT) and frequency, and degree and characteristics of adverse events, vital signs, physical examination, electrocardiogram, clinical laboratory test, and radiologic test will be conducted concurrently for the safety evaluation.

Safety and pharmacokinetics and pharmacodynamics of GX-G3 will be evaluated for the purpose of secondary evaluation, and immunogenicity will be evaluated in order to determine the existence of antibody. In addition, difference in pharmacokinetic and pharmacodynamic characteristics safety and immunogenicity between GX-G3 and Neulasta® will be compared.

vii. Statistical Methods

All randomized subjects who had at least one dose of investigational product and had visited after the dose was used for statistical analysis. Intention-to-treat (ITT) analysis group was primarily considered for efficacy evaluation and results from peprotocol (PP) analysis group were also provided. Safety analysis group was used for safety evaluation.

Inclusion of serious protocol deviations considered to affect study result interpretation in statistical analysis was accounted after classifying by case. The extent and cause of deviation should be accurately recorded for those protocol deviations and investigator, sponsor, monitor and statistician examined the affectedness before including in statistical analysis when writing the clinical study report.

Primary error was adjusted with significance level of 2.5% for each multiple test in assessment of the primary efficacy outcome, changes in HbA1c at week 24. For other variables, all hypotheses were assessed with 5% of significance level on both sides. SAS (Version 9.2) was used for statistical analysis.

Last observation carried forward (LOCF) was applied for the missing data included in ITT analysis of efficacy. Available data sets were used for efficacy evaluation at each visit and safety analysis.

Descriptive statistics were provided for demographics and medical history of subjects in ITT population by each group and assessments for difference in average or ratio were performed. Averages, standard deviation, median, minimum, and maximum were provided and ANOVA or Kruskal-Wallis test were applied to assess significance of between group differences. For non-successive data, incidence and ratio were provided and Chi-square test or Fisher's exact test were applied for assessment.

Covariate analysis calibrated by baseline WBC, ANC and CD34+ was applied to changes of those parameters and between group differences were assessed by multiple comparisons. Paired t-test was used to evaluate the difference between before and after dosing.

Descriptive statistics were provided for secondary/tertiary efficacy outcomes and average or ratio were assessed if differences existed or not for each dosing groups. For successive data, covariate analysis calibrated by baseline or Kruskal-Wallis test were used to assess statistical significance between groups and intra-group difference between before and after dosing was assess by paired t-test or Wilcoxon's signed rank test. For non-successive data, Chi-square test was applied for analysis.

viii. Phase I Clinical Study Results

Pharmacokinetic Results

The data related to safety, pharmacokinetic (PK), pharmacodynamic (PD) and immunogenicity parameters were analyzed using descriptive statistical methods. Compliance was further confirmed by bioanalytical assessment of GX-G3 in serum samples. The lower limit of quantification of the test drug in the present study was 1.25 ng/mL. The following PK parameters were obtained: $C_{max}$, maximum concentration; $AUC_{last}$, area under the concentration-time curve from 0 to last sampling point; $AUC_{inf}$, area under the concentration-time curve from 0 to infinite; $t_{max}$, time to reach the maximum plasma concentration; $t_{1/2}$, terminal half-life. Pharmacokinetic parameters of GX-G3 and Neulasta® are presented in Table 14.

TABLE 14

Pharmacokinetic parameters of GX-G3 and Neulasta ®
Arithmetic mean (CV %)

| | Dose of GX-G3 (μg/kg) | | | | | | Neulasta |
|---|---|---|---|---|---|---|---|
| | 12.5 | 25 | 50 | 100 | 200 | 400 | 6 mg |
| $C_{max}$ (ng/mL) | 4.2 (60.6%) | 13.6 (97.5%) | 42.5 (87.9%) | 77.5 (78.4%) | 374.8 (48.5%) | 1044.3 (64.6%) | 155.7 (42%) |
| $AUC_{last}$ (ng · h/mL) | 100.0 (64.8%) | 333.1 (82.9%) | 1198.8 (68.4%) | 2548.8 (91.2%) | 13073.4 (56.1%) | 50108.5 (59.3%) | 5546.7 (5%3) |
| $AUC_{inf}$ (ng · h/mL) | NC | 565.8 (74.5%) | 2544.1 (—) | 2903.2 (—) | 13474.1 (53.8%) | 50493.3 (58.9%) | 5615.4 (52.7%) |
| $t_{max}$ (Median) (h) | 5.0 | 10.0 | 10.0 | 10.0 | 12.0 | 16.2 | 16.2 |
| $t_{1/2}$ (h) | NC | 78.1 (91.1%) | 169.0 (—) | 151.6 (152.7%) | 128.8 (94.9%) | 99.1 (40.7%) | 23.7 (49.5%) |

NC: Not calculated

According to results, dosing with Neulasta® 6 mg showed pharmacokinetic profiles in AUC and $C_{max}$ which ranged between 100 μg/kg and 200 μg/kg of GX-G3. Also, the inter-individual variability for the parameters regarding drug exposure (AUC and $C_{max}$), represented by CV, did not seem different across the dose levels and from that of comparator.

The pharmacokinetic parameters showed proportional rank order of doses, Neulasta® 6 mg/mL showed a range between 100 μg/kg and 200μ/kg of GX-G3. To evaluate long-acting GX-G3 of HyFC technology, the half-life is an important parameter. All doses of GX-G3 showed considerably long half-life of 78.1 hrs for 25 μg/kg, 169.0 hrs for 50 μg/kg, 151.6 hrs for 100 μg/kg, 128.8 hrs for 200 μg/kg and 99.1 hrs for 400 μg/mL and thus considerably longer as compared to that Neulasta® 6 mg/mL (23.7 hrs). The median time to reach the maximum plasma concentration were 5.0 hrs, 10.0 hrs, 10.0 hrs, 10.0 hrs, 12.0 hrs and 16.2 hrs respectively in GX-G3 12.5, 25, 50, 100, 200 and 400 μg/kg dose groups.

Figure 12:
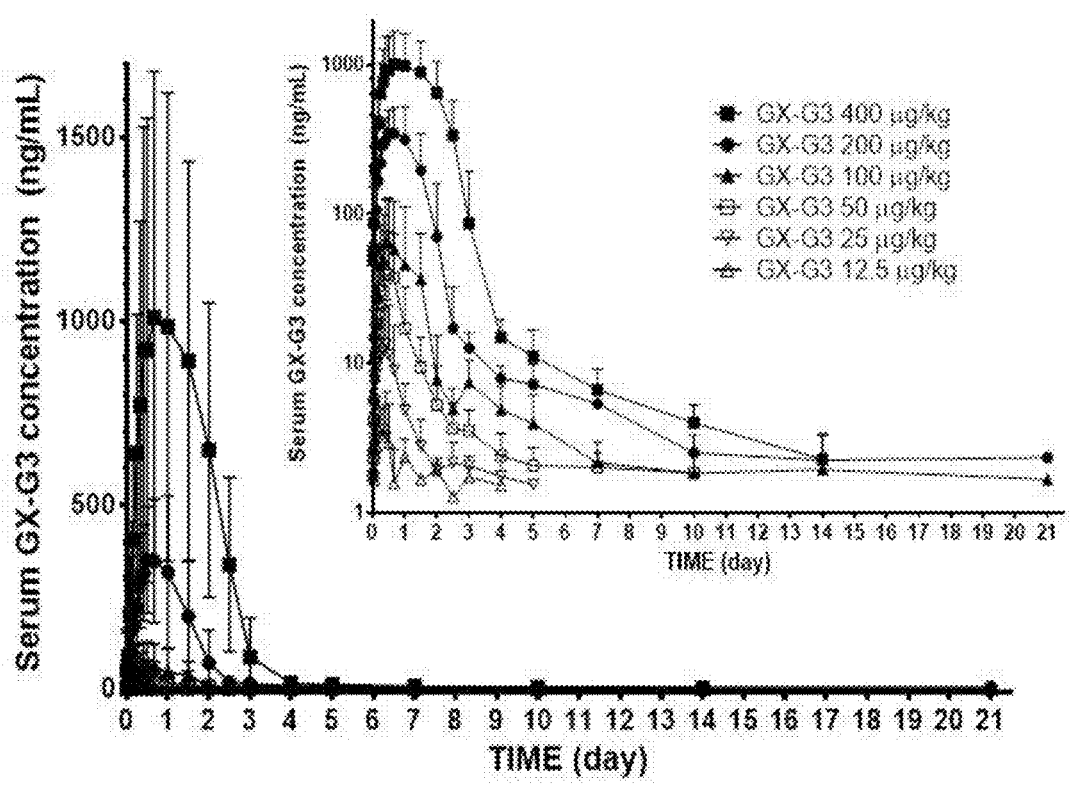
FIG. 12 shows mean serum GX-G3 concentration versus time plots after single subcutaneous administration of GX-G3.
Figure 13:
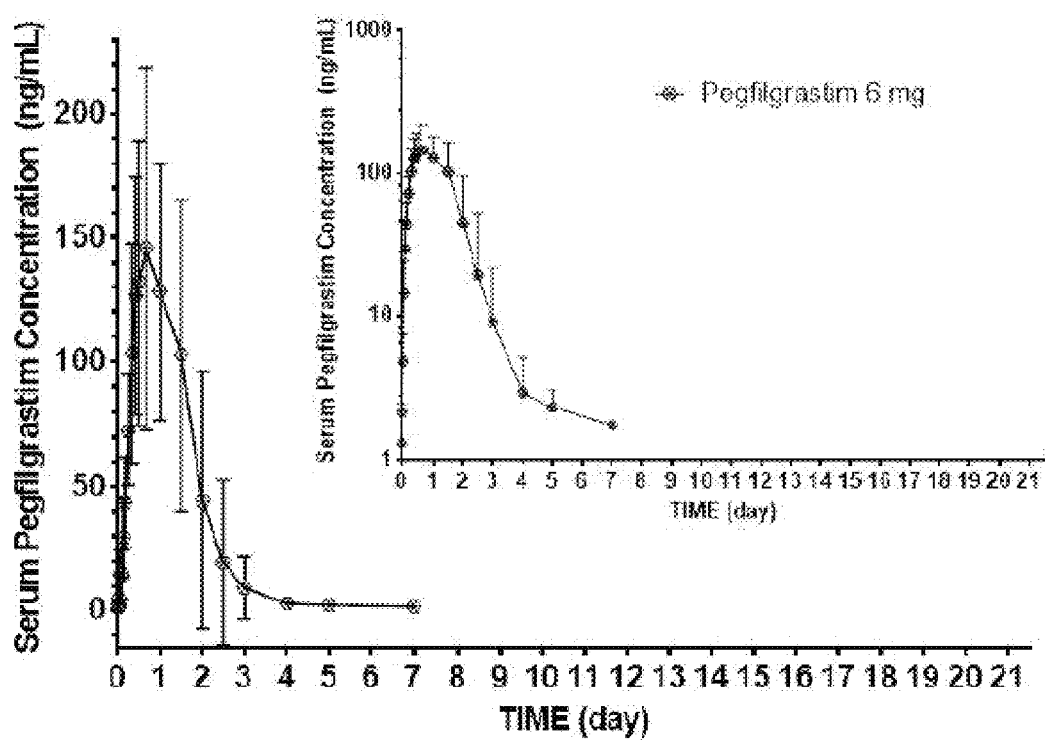
FIG. 13 shows mean serum Pegfilgrastim concentration versus time plots after single subcutaneous administration of pegfilgrastim 6 mg.

The plasma concentration versus time profiles after single subcutaneous administration of GX-G3 and Neulasta® (Pegfilgrastim) are presented in the FIGS. 12 and 13, respectively.

Figure 14:
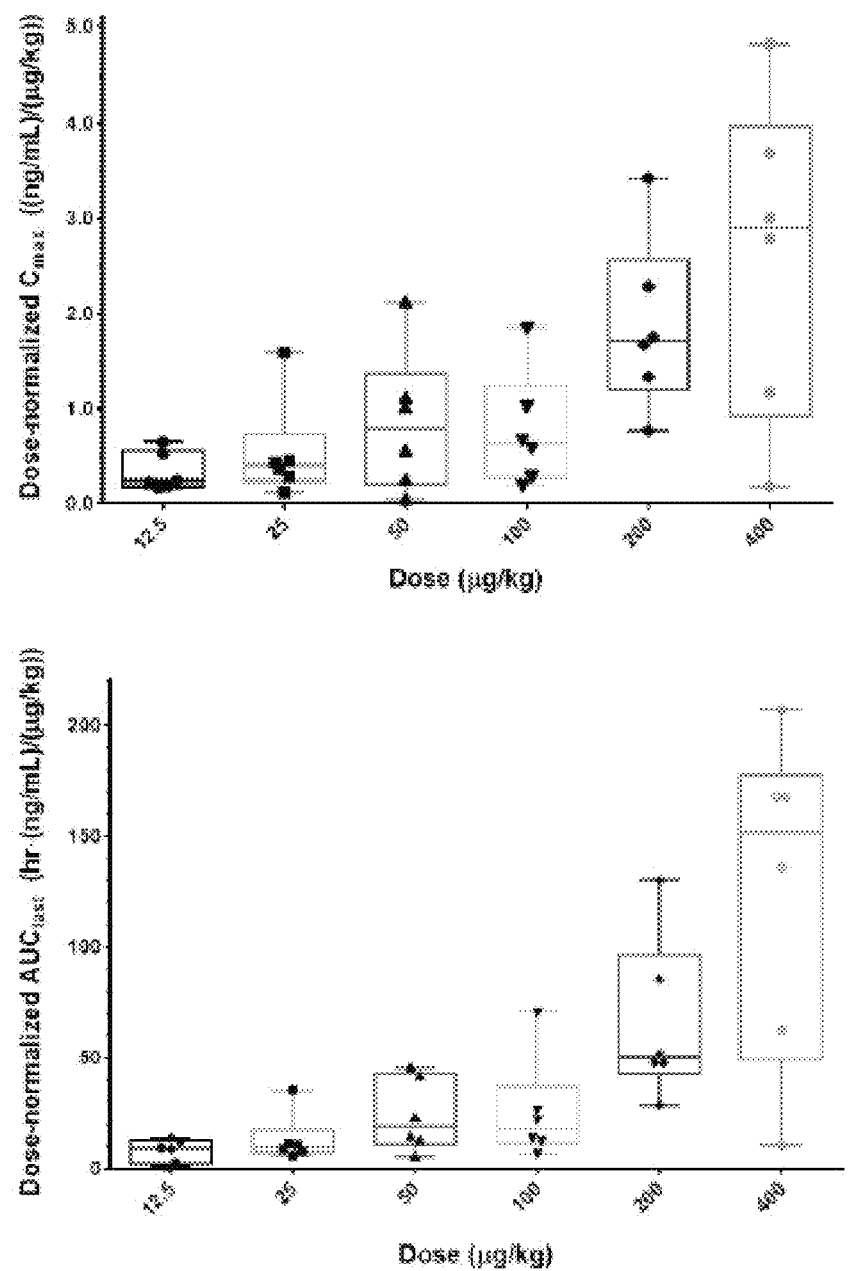
FIG. 14 shows box and whisker plots of dose-normalized $C_{max}$ (upper) and $AUC_{last}$ (lower) of GX-G3.

The pharmacokinetic profiles showed a supra-proportional increase in AUC and $C_{max}$ with increasing dose as shown in FIG. 14. The dose-adjusted $AUC_{last}$ were 5.7±5.2, 10.9±11.1, 19.0±16.4, 19.2±23.3, 58.0±36.7 and 89.3±74.3 (hr·ng/mL)/(μg/kg) respectively for GX-G3 12.5, 25, 50, 100, 200 and 400 μg/kg dose groups. The dose-adjusted $C_{max}$ were 0.29±0.20, 0.40±0.53, 0.50±0.75, 0.59±0.61, 1.69±0.91 and 1.78±1.69 (ng/mL)/(μg/kg) respectively for each dose group. These results showed the non-linear pharmacokinetics of GX-G3

Efficacy Results

Figure 15:
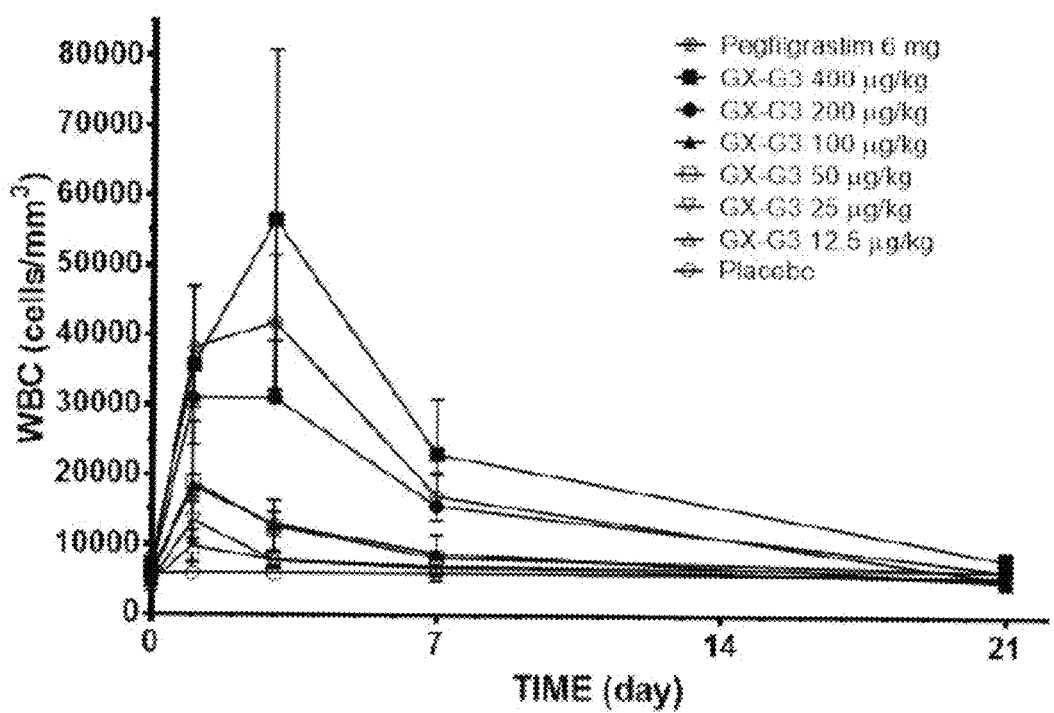
FIG. 15 shows mean WBC (white blood cell)-time curves after single subcutaneous injection of GX-G3, Pegfilgrastim and placebo.

The assessment of AUEC (area under the effect curve) of WBC (white blood cell) counts after administration of GX-G3 demonstrated that AUEC increased with the increase in GX-G3 dose in non-linear manner as shown in Table 15 and FIG. 15.

TABLE 15

Descriptive WBC change parameters after single subcutaneous injection Mean (CV %)

| | Placebo | Dose of GX-G3 (μg/kg) | | | | | | Neulasta |
| | | 12.5 | 25 | 50 | 100 | 200 | 400 | 6 mg |
|---|---|---|---|---|---|---|---|---|
| Maximal change (cells/mm$^3$) | 1082 (82.6%) | 5035 (52.0%) | 8687 (27.4%) | 13112 (54.6%) | 12970 (12.9%) | 27930 (21.3%) | 49367 (47.8%) | 36783 (23.8%) |
| Baseline-corrected AUEC (day · cells/mm$^3$) | 2352 (497.1%) | 39231 (31.8%) | 55365 (16.2%) | 68239 (54.9%) | 71908 (39.7%) | 206256 (30.7%) | 330622 (39.0%) | 248892 (21.7%) |
| $t_{max}$ (Median) (day) | 7.0 | 1.0 | 1.0 | 1.0 | 1.0 | 2.0 | 3.0 | 3.0 |

*CV %: coefficient of variation

In comparison of baseline-corrected AUEC of WBC between GX-G3 and Neulasta®, the mean baseline-corrected AUEC in subjects receiving GX-G3 200 μg/kg (206,256±63,366 day·cells/mm$^3$) was similar to that in subjects receiving Neulasta® 6 mg fixed dose (248,892±54,096 day·cells/mm$^3$).

Figure 16:
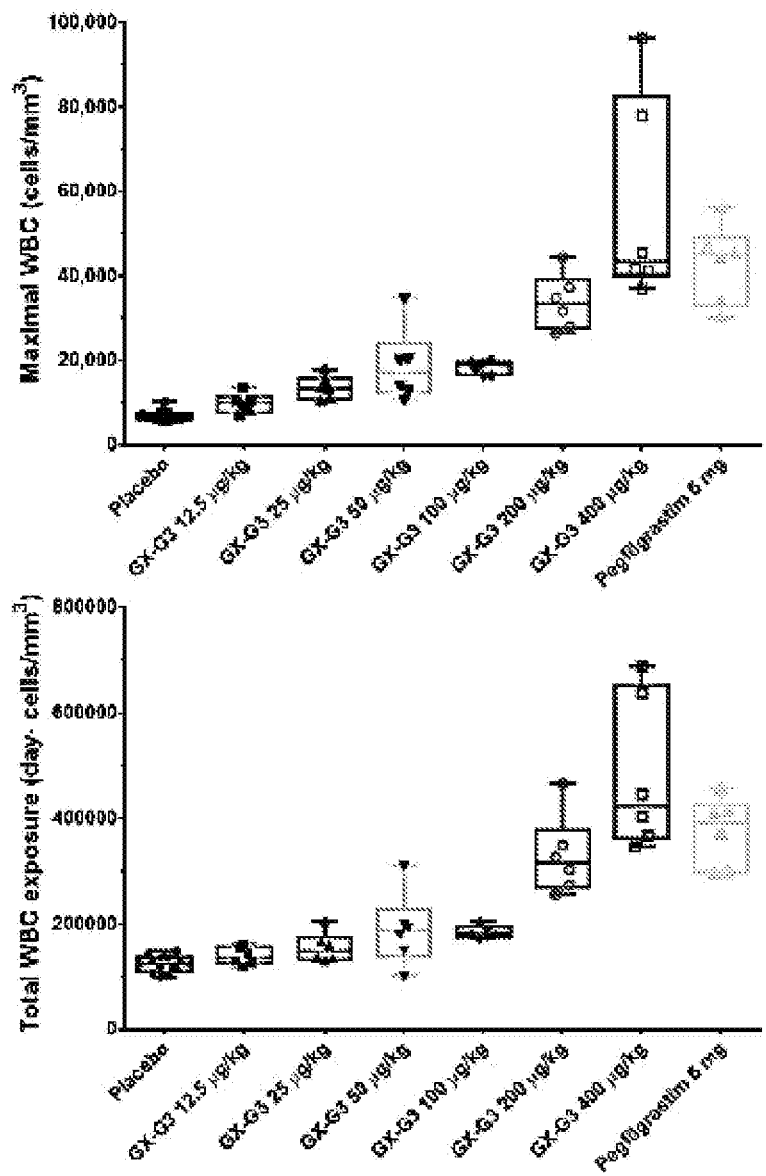
FIG. 16 shows maximum WBC (upper) and total WBC exposure (lower) to the body after a single subcutaneous injection of GX-G3, Pegfilgrastim and placebo.

Regarding the maximal change of WBC counts (FIG. 16), mean maximum change in subjects receiving Neulasta® 6 mg fixed dose (36,783±65,993 cells/mm$^3$) seemed greater than that in subjects receiving GX-G3 200 μg/kg (27,930±5,939 cells/mm$^3$), but smaller than that in subjects receiving GX-G3 400 μg/kg (49,367±23,582 cells/mm$^3$).

The time to reach the maximum WBC count ($t_{max}$) seemed delayed with the increasing dose. The median values of $t_{max}$ were 1 day for the dose levels from 12.5 to 100 μg/kg, 2 days for the dose level of 200 μg/kg and 3 days for the dose level of 400 μg/kg.

Figure 17:
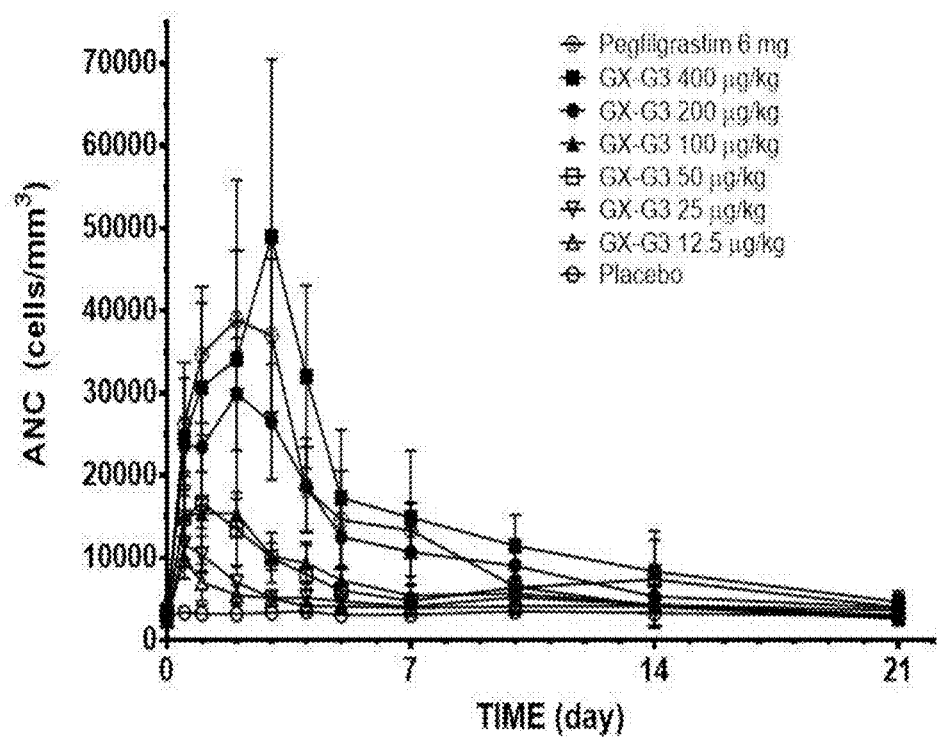
FIG. 17 shows mean ANC (absolute neutrophil count)-time curves after single subcutaneous injection of GX-G3, Pegfilgrastim and placebo.

The plasma ANC count-time profile is presented in FIG. 17 and the data of ANC parameters are summarized in Table 16.

Figure 18:
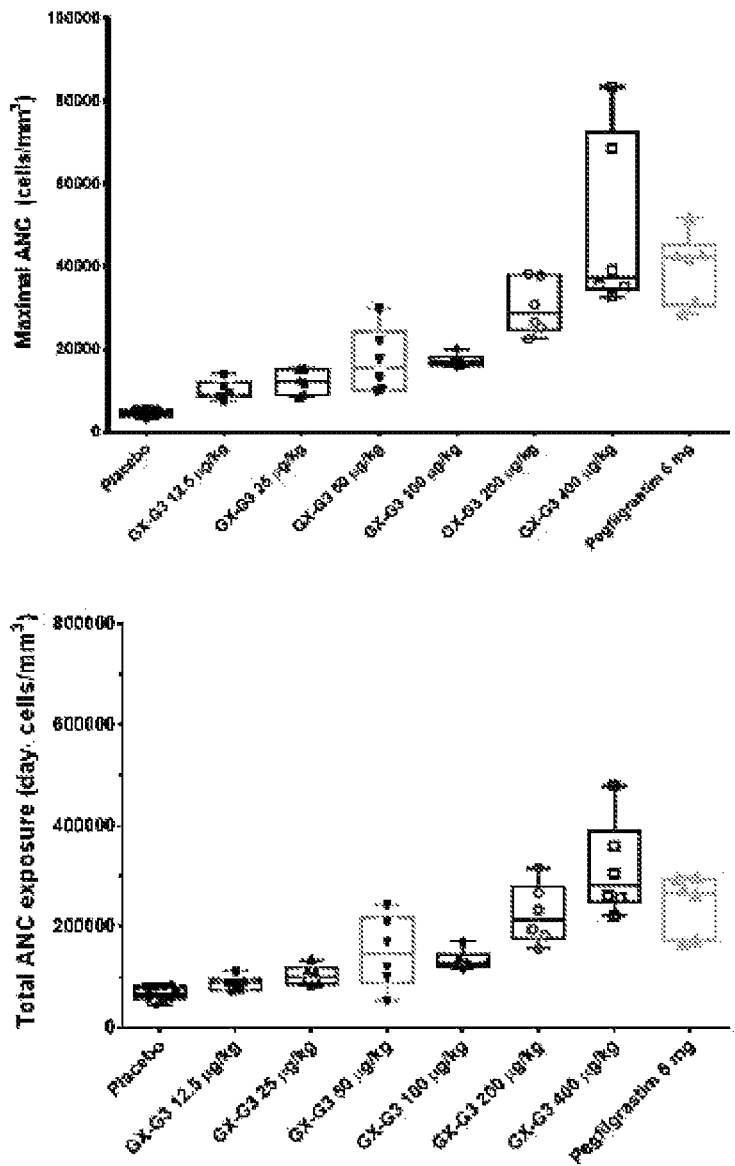
FIG. 18 shows maximum ANC (upper) and total ANC exposure (lower) to the body after a single subcutaneous injection of GX-G3, Pegfilgrastim and placebo.
Figure 19:
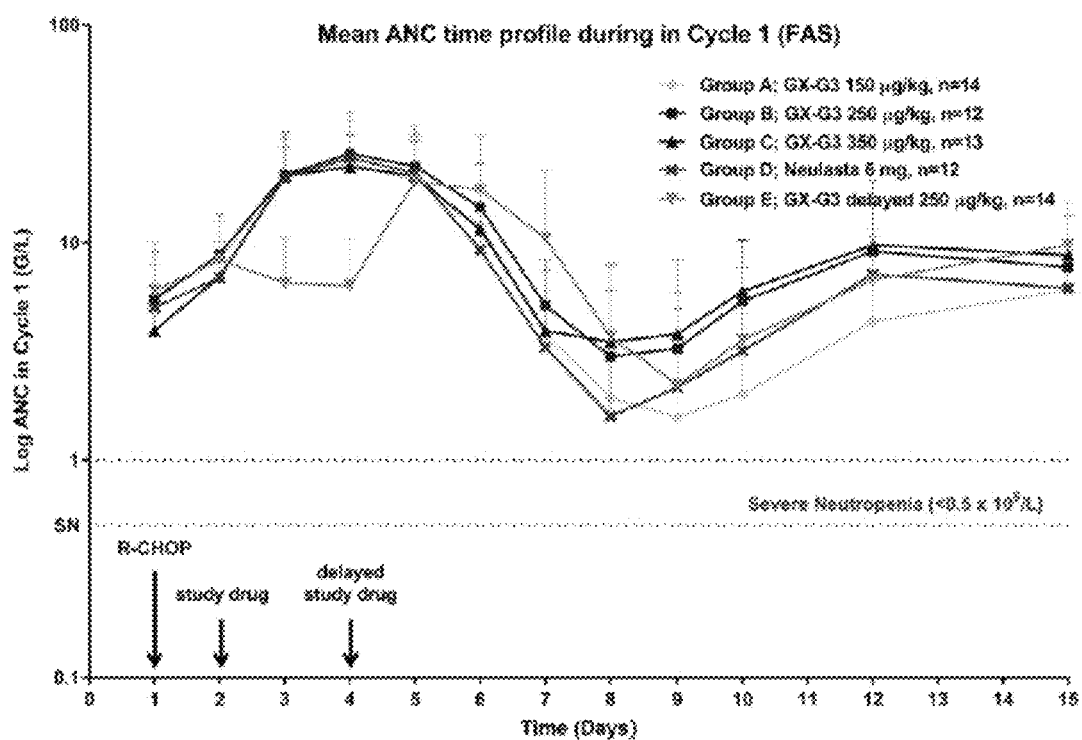
FIG. 19 shows mean ANC time profile for cycle 1 (FAS).
Figure 20:
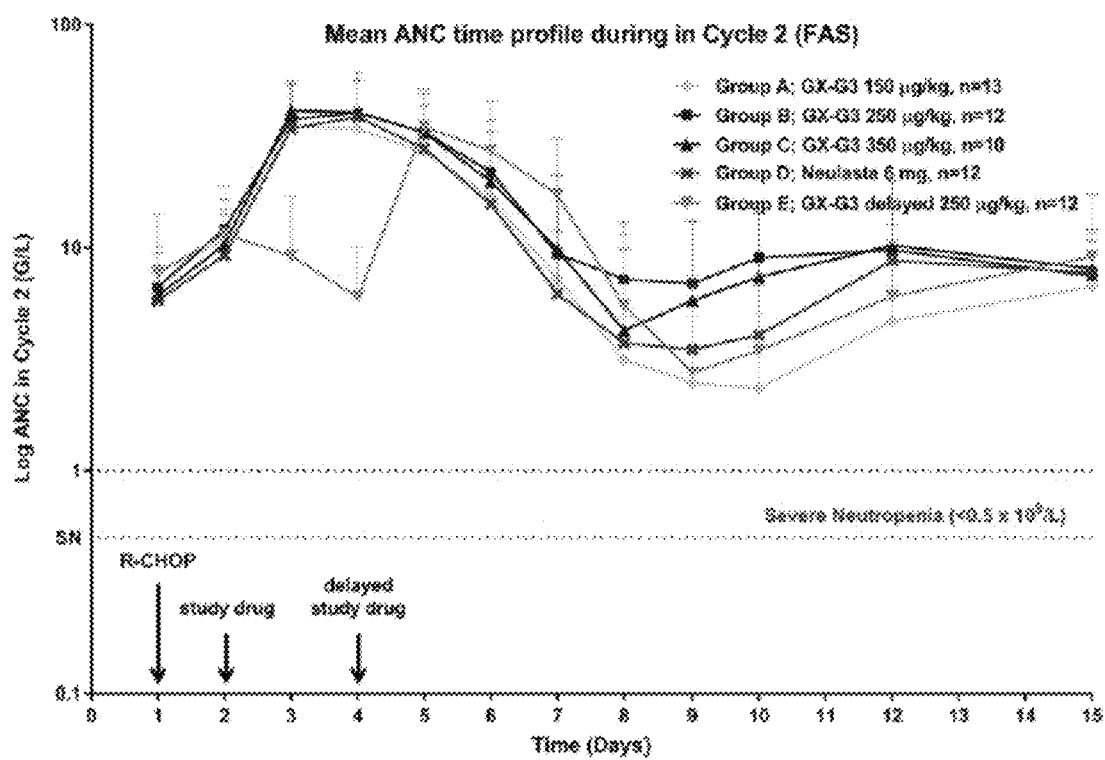
FIG. 20 shows mean ANC time profile for cycle 2 (FAS).
Figure 21:
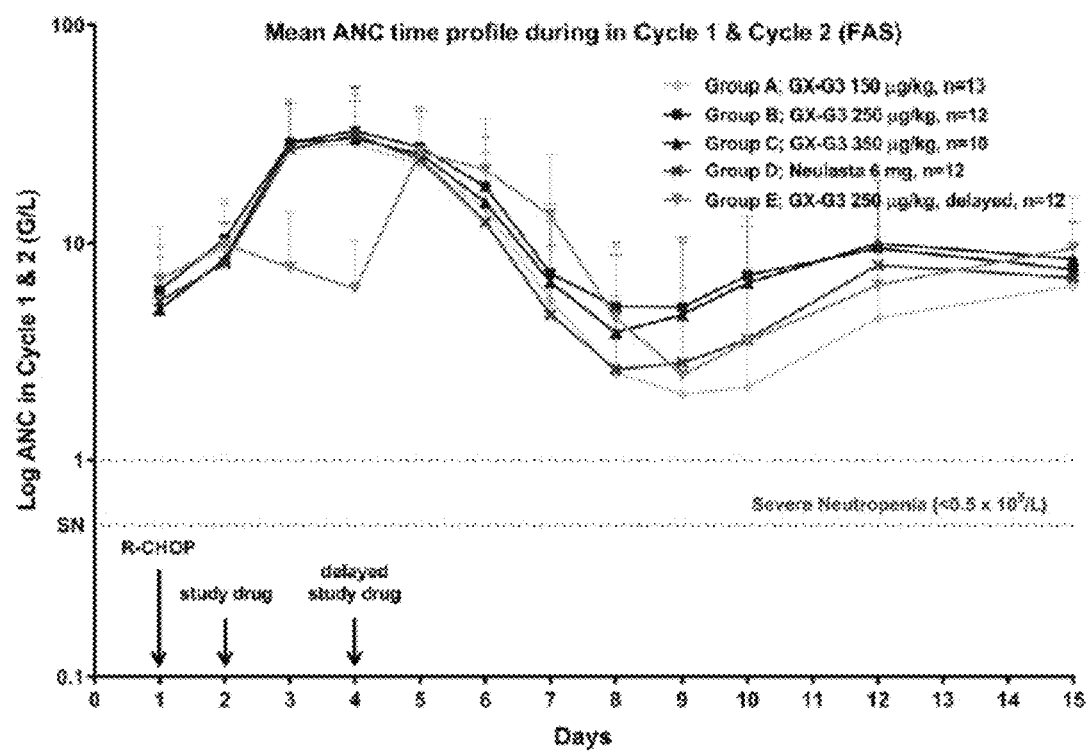
FIG. 21 shows mean ANC time profile for both cycles (FAS).
Figure 22:
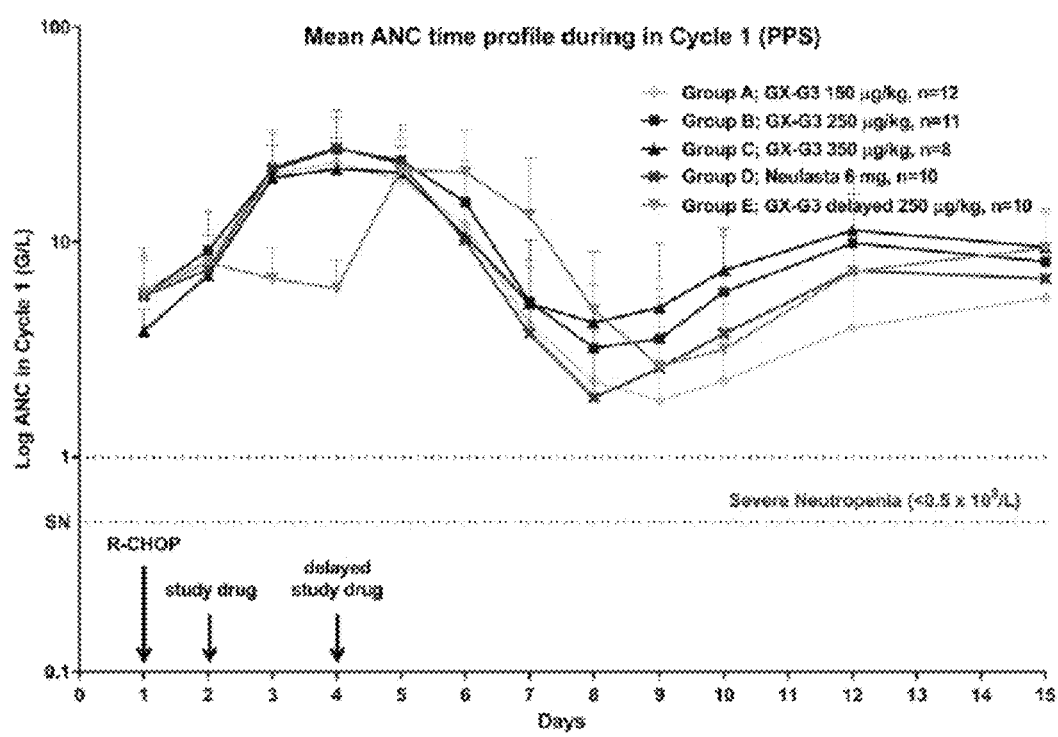
FIG. 22 shows mean ANC time profile for cycle 1 (PPS).
Figure 23:
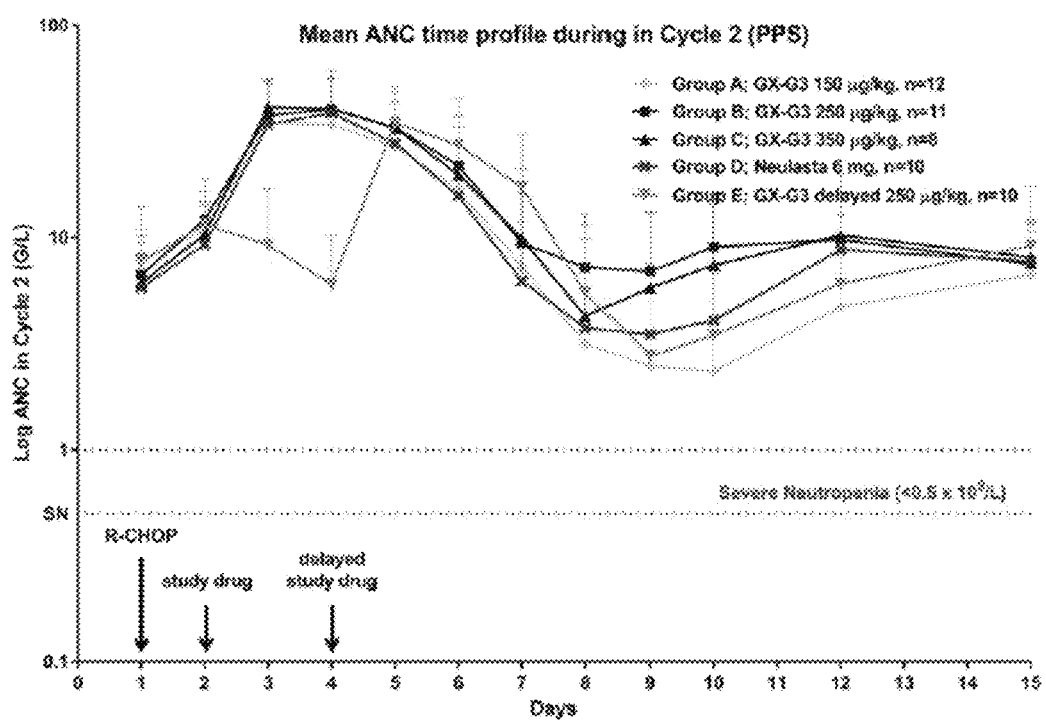
FIG. 23 shows mean ANC time profile for cycle 2 (PPS).

The assessment of AUEC of ANC counts after administration of GX-G3 demonstrated that AUEC increased with the increase in GX-G3 dose in non-linear manner (FIG. 18). In comparison of baseline-corrected AUEC of ANC counts between GX-G3 and Neulasta®, the mean baseline-corrected AUEC in subjects receiving GX-G3 200 μg/kg (161,856±45,304 day·cells/mm$^3$) was similar to that in subjects receiving Neulasta® 6 mg fixed dose (175,818±44,374 day·cells/mm$^3$).

The time to reach the maximum ANC count ($t_{max}$) seemed delayed with the increasing dose. The median values of $t_{max}$ were 1 day for the dose levels of 12.5 and 25 μg/kg, 2 days for the dose level from 50 to 200 μg/kg and 3 days for the dose level of 400 μg/kg.

The inter-individual variability for the pharmacodynamics parameters such as AUEC of ANC counts and maximal change of ANC counts did not seem related to the dose level of GX-G3 (CV % of maximum ANC change: 11.7-50.9; CV % of AUEC of ANC: 14.5-47.4) and the variability of the dose level of 200 μg/kg (CV % of maximum ANC change: 21.6; AUEC of ANC: 26.1) was similar to those of Neulasta® 6 mg fixed dose (CV % of maximum ANC change: 21.4; AUEC of ANC: 24.2).

In conclusion, absolute neutrophil count (ANC), WBC count, and CD34+ cell count were measured in subjects after a single-dose administration of GX-G3 12.5, 25, 50, 100, 200 and 400 μg/kg, Neulasta® 6 mg, or placebo.

TABLE 16

Descriptive ANC change parameters after single subcutaneous injection - Mean (CV %)

| | Placebo | Dose of GX-G3 (μg/kg) | | | | | | Neulasta |
| | | 12.5 | 25 | 50 | 100 | 200 | 400 | 6 mg |
|---|---|---|---|---|---|---|---|---|
| Maximal change (cells/mm$^3$) | 1399 (42.7%) | 7307 (38.8%) | 9442 (25.6%) | 13920 (50.9%) | 13950 (11.7%) | 27090 (21.6%) | 45488 (47.0%) | 36517 (21.4%) |
| Baseline-corrected AUEC (day · cells/mm$^3$) | 3397 (330.5%) | 34867 (30.0%) | 51943 (14.8%) | 81878 (69.1%) | 66556 (41.9%) | 161856 (28.0.%) | 240886 (36.0%) | 175818 (25.2%) |
| $t_{max}$ (Median) (day) | 0.5 | 1.0 | 1.0 | 2.0 | 2.0 | 2.0 | 3.0 | 2.5 |

WBC and ANC increased at all dose ranges of GX-G3 compared with the placebo. The maximum changes in ANC and AUEC was greater in subjects receiving a higher dose. Especially, GX-G3 dose range of 200-400 μg/kg showed the potential superiority to the active control in the pharmacodynamics responses.

Safety Results

No serious adverse event and other significant adverse event were reported from this study. A total of 54 subjects were in the safety population and there were 133 recordable adverse events (AE), and consisting of 115 grade 1 (86.47%) and 18 grade 2 (13.53%). These events were evenly distributed for each treatment group including placebo and Neulasta® group, as negative and positive controls, respectively.

Recorded adverse drug reactions were reported by 16 (12.03%, only mild) for placebo, 23 (17.29%, 19 mild and 4 moderate) for Neulasta®, 4 (3.01%, 4 mild) for 12.5 μg/kg group, 11 (8.27%, 11 mild) for 25 μg/kg group, 11 (8.27%, 8 mild and 3 moderate) for 50 μg/kg group, 19 (14.29%, 18 mild and 1 moderate) for 100 μg/kg group, 29 (21.80%, 24 mild and 5 moderate) for 200 μg/kg group and 20 (15.04%, 15 mild and 5 moderate) for 400 μg/kg group. No strong relationship between dose and AE was observed.

Immunogenicity Results

No immunogenic issues were raised.

Overall Conclusion of Phase I Study

This study was the first-in-human study with GX-G3 and was performed to investigate the safety and tolerability of single doses of GX-G3 in healthy male subjects. In addition, it was performed to characterize the PK and PD profile of single doses of GX-G3 in healthy male subjects. Overall results of this study were as follows:

- Single subcutaneous doses GX-G3 in the dose range of 12.5, 25, 50, 100, 200, 400 μg/kg were safe and well tolerated by a group of 54 healthy male subjects.
- Among 133 recordable AEs consisting of 115 (86.47%) grade 1 (mild) and 18 (13.53%) grade 2 (moderate) AEs, no considerable and reportable AEs were observed for all treatment groups before and after administration.
- No significant difference of AEs observed between high dose GX-G3 treatment group and that of Neulasta®.
- There were no indications that any of the subjects developed antibodies against GX-G3 following single dose treatment.
- $C_{max}$ and AUC of GX-G3 increased with dose in a non-linear fashion at the dose range of 12.5 to 400 μg/kg.
- In overall, GX-G3 showed half-life range of 78.1 hr to 151.6 hr and is 3.3 of 7.13-fold longer than Neulasta® with a half-life of 23.7 hr
- Following a single subcutaneous injection GX-G3, WBC and ANC increased at all dose ranges of GX-G3 compared to the placebo group in a dose-dependent manner.
- The maximum changes in ANC and AUEC was greater in subjects receiving a higher dose of GX-G3.
- Pharmacodynamics responses at dose of 200 μg/kg of GX-G3 are comparable to those of Neulasta® and 400 μg/kg of GX-G3 showed the potential superiority to Neulasta®.
- There was a clear relationship between GX-G3 concentrations and ANC increases
- An appropriate dose of GX-G3 may be located between 200 μg/kg to 400 μg/kg without considering significant toxicity
- Due to long-acting nature of product property and comparable efficacy of GX-G3 compared to Neulasta®, it may provide better patient compliance to those who suffer from chemotherapy-induced neutropenia.

Example 19

Clinical Study: Phase II

The Phase II Study was performed to determine the efficacy, safety and tolerability of three different doses of GX-G3 and to compare the Neulasta® (Pegfilgrastim) to select the ideal dose range and optimal point in time for dosing for Phase III.

i. Objective

For Phase II, the primary objective was to assess the efficacy, safety, and tolerability of three doses of GX-G3 with the aim of selecting the optimal dose range by comparing each of the doses with the reference product (Neulasta®). Another aim for including one group with delayed administration (250 μg/kg of GX-G3 on day 3 after chemotherapy dosing) was to evaluate the optimal point in time for dosing of the test product.

The secondary objectives were to investigate the pharmacokinetics of GX-G3 and the safety of the immunogenicity of GX-G3.

ii. Study Design and Plan

This is a randozimed, parallel group, multi-centre Phase II study of GX-G3 compared in patients with Non-Hodgkin's Lymphoma receiving R-CHOP therapy. The indication for administration of G-CSF as defined in the summary of product information (SmPC) of the comparator in the present trial (Neulasta®) is as follows: "Reduction in the duration of neutropenia and the incidence of febrile neutropenia in adult patients treated with cytotoxic chemotherapy for malignancy (with the exception of chronic myeloid leukaemia and myelodysplastic syndromes)." (Summary of Product Characteristics Neulasta®).

Numerous schemes of cytotoxic chemotherapy are being used for different types of cancer. In order to reduce the heterogeneity caused both by the different types of cancer and the different types of cytotoxic chemotherapy, it was decided to only include patients with non-Hodgkin lymphoma treated with R-CHOP chemotherapy in the present trial. By reducing the heterogeneity it is possible to better differentiate between different doses of the test product. One standard R-CHOP cycle comprises the following:

Rituximab 375 mg/m² i.v. on day 1
Cyclophosphamide 750 mg/m² i.v. on day 1
Doxorubicin 50 mg/m² i.v. on day 1
Vincristine 1.4 mg/m² (max 2 mg) i.v. on day 1
Prednisone 100 mg p.o. q.d. on days 1-5

The study was conducted as an open, multicentre, randomized, trial in five parallel groups of patients. Each of the patients were randomly assigned to one of 5 possible treatments:

Test (150 μg/kg BW/24 hrs after R-CHOP)
Test (250 μg/kg BW/24 hrs after R-CHOP)
Test (350 μg/kg BW/24 hrs after R-CHOP)
Test (250 μg/kg BW/72 hrs after R-CHOP)
Reference (Neulasta® 6 mg/0.6 mL/24 hrs after R-CHOP).

Patients underwent a screening/baseline phase with a maximum duration of 4 weeks prior Day 1, the first day of the first treatment cycle and were treated only after check and confirmation of the inclusion criteria and exclusion criteria.

The efficacy parameters of absolute neutrophil count (ANC), white blood cell count (WBC) and differential blood count were determined. The safety parameters of treatment-emergent adverse events, clinical examination, safety laboratory results and antibodies against GX-G3 were determined.

The duration of treatment in this trial was comprised two sequential treatment cycles with R-CHOP. By evaluating the effect of the test product during two cycles of chemotherapy instead of one single cycle, more data were generated per patient.

At the end of the treatment phase, patients underwent a final examination. The maximum duration of the study is about 11 weeks for an individual patient.

iii. Study Population

The number of 65 patients who fulfilled the inclusion criteria and did not present any of the exclusion criteria were planned to be randomised to achieve the aim of the present trial.

For Phase II, subjects were screened based on the following characteristics or parameters:

Inclusion Criteria:
1. Male or female patients years of age.
2. Patients with Non-Hodgkin's Lymphoma confirmed by immunohistochemistry or flow cytometry: stage III-IV follicular lymphoma (Ann Arbor staging) or CD20 positive diffuse large B cell non-Hodgkin lymphoma.
3. Patients who fulfill the criteria for receiving R-CHOP (rituximab, cyclophosphamide, doxorubicin, vincristine, prednisolone) therapy for at least 2 cycles of 21 days each.
4. Patients who are about to receive the first two cycles of R-CHOP therapy within a series of several cycles (previous exposure to R-CHOP is allowed but in another series of cycles more than 3 months before randomization in the present trial).
5. ECOG performance status 0, 1, or 2.
6. Life expectancy with treatment of at least 6 months.
7. Patients willing and able (e.g. mental and physical condition) to participate in all aspects of the study, attending scheduled visits, and compliance with protocol requirements as evidenced by providing signed written informed consent.

Exclusion/Withdrawal Criteria:

Subjects presenting any of the following criteria were not included in the trial:
1. History of hypersensitivity or intolerance to the active substance or any of the excipients of the study medication (e.g. sorbitol, fructose, or to latex) or to any of the components of R-CHOP therapy.
2. Known hypersensitivity to *E. coli*-derived products (e.g., Filgrastim, Humulin® Insulin, L-Asparaginase, Humatrope® Growth Hormone, Intron A®)
3. Burkitt's or B-lymphoblastic lymphoma.
4. Non-Hodgkin's Lymphoma with CNS involvement.
5. Active infection requiring treatment with systemic (intravenous or oral) anti-infectives (antibiotic, antifungal, antiviral) at baseline.
6. Exposure to R-CHOP therapy or pegfilgrastim within the last 3 months before randomization.
7. Known lack of neutropenia in patients previously exposed to R-CHOP therapy.
8. Positive serologic findings for human immunodeficiency virus (HIV) antibodies, hepatitis B surface antigen (HBsAg), and/or hepatitis C virus (HCV) antibodies.
9. Any premalignant myeloid condition or any malignancy with myeloid characteristics (e.g., myelodysplastic syndromes, acute or chronic myelogenous leukaemia).
10. Prior malignancy within the last 5 years, with the exception of surgically cured basal cell carcinoma, squamous skin cell carcinoma, or in situ carcinoma of the cervix.
11. Prior bone marrow or stem cell transplantation.
12. Severe hepatic impairment: serum bilirubin above 51.3 μmol/L (3 mg/dL) or serum albumin below 28 g/L (2.8 g/dL).
13. Baseline neutrophil count $<1.5 \times 10^9$/L or platelet count $<100 \times 10^9$/L.
14. Demyelinating form of Charcot-Marie-Tooth syndrome.
15. Any of the following during the last month before randomization: pneumonia, pulmonary oedema, interstitial lung disease, lung infiltrations.
16. Sickle cell trait or sickle cell disease.
17. Major surgery within 2 weeks prior to randomization.
18. Patient is currently enrolled in, or has completed less than 30 days before the screening examination of the present trial another clinical trial with an investigational drug.
19. Previous enrolment in this study.
20. Women of childbearing potential unable or unwilling to undergo pregnancy tests and practice adequate contraceptive measures. Reliable methods for women are hormonal contraceptives, surgical intervention (e.g. tubal ligation), intrauterine device (IUD) and sexual abstinence.
21. Legal incapacity and/or other circumstances rendering the patient unable to understand the nature, scope and possible consequences of the study.
22. Alcohol/drug dependence or abuse (excluding tobacco abuse).
23. Unreliability or lack of cooperation.
24. Urinary outflow obstruction.
25. Impaired cardiac function: myocardial insufficiency, recent (last 6 months) myocardial infarction, severe arrhythmias.
26. Any other condition of the patient (e.g., serious or unstable medical or psychological condition, acute psychosis, severe and long-lasting febrile neutropenia) that in the opinion of the investigator may compromise evaluation of the study treatment or may jeopardize patient's safety, compliance or adherence to protocol requirements
27. Pregnant or breast-feeding women.
28. Any change in the dosage of R-CHOP treatment after the first cycle of the trial. If any of the exclusion criteria with numbers 22-28 are registered after randomization, this will be regarded as a withdrawal criterion.

iv. Administered Treatment

The present study is a dose range finding study. The selected doses based from results of pre-clinical studies and a clinical study performed in healthy volunteers. Since the data from Phase I demonstrated that single subcutaneous doses GX-G3 in the dose range of 12.5, 25, 50, 100, 200, 400 μg/kg were safe and well tolerated; in order to determine the optimal dose range of GX-G3, Phase II clinical study was conducted at 150 μg/kg, 250 μg/kg and 350 μg/kg doses. An administered vial (1 mL) contains 20 mg active ingredients of the drug product.

The Test Product is GX-G3 20 mg/mL Solution for injection (subcutaneous injection) with described treatments below:

Treatment A, B, C:

The Test Product of GX-G3 20 mg/mL Solution for injection (subcutaneous injection) is administered with described treatments below:

1 subcutaneous injection as a 20 mg/mL subcutaneous injection 24 hours following R-CHOP administration during the first 2 consecutive R-CHOP cycles of 21 days each (in total of two single doses).

Treatment D:

The Reference Product of Neulasta® (Pegfilgrastim) 6 mg/0.6 mL prefilled syringe (subcutaneous injection) is administered with described treatment below:

1 subcutaneous injection as a 6 mg/0.6 mL subcutaneous injection 24 hours following R-CHOP administration during the first 2 consecutive R-CHOP cycles of 21 days each (in total of two single doses).

Figure 25:
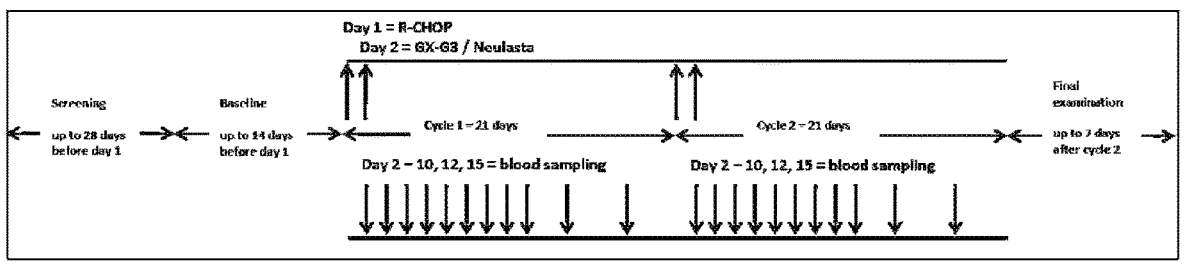
FIG. 25 illustrates a schedule for Treatment A, B, C, D (Study medication 24 h after R-CHOP).

A schedule for Treatment A, B, C, D (Study medication 24 h after R-CHOP) are illustrated in FIG. 25.

Treatment E:

The Test Product of GX-G3 20 mg/mL Solution for injection (subcutaneous injection) is administered with described treatment below:

1 subcutaneous injection as a 20 mg/mL subcutaneous injection 72 hours following R-CHOP administration during the first 2 consecutive R-CHOP cycles of 21 days each (in total of two single doses)

Figure 26:
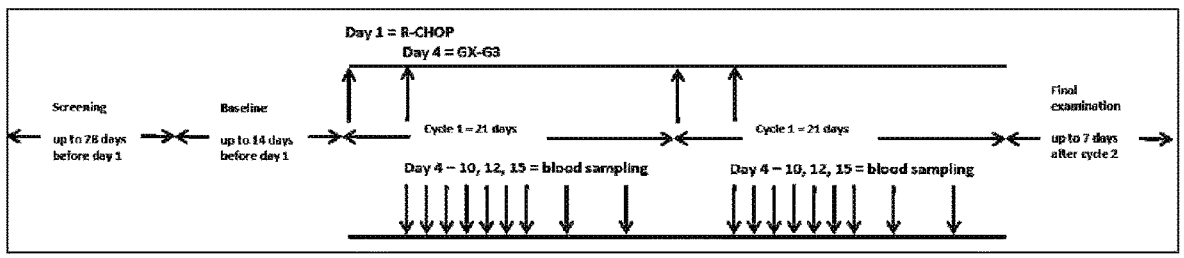
FIG. 26 illustrates a schedule for Treatment E (Study medication 72 h after R-CHOP).

A schedule for Treatment E (Study medication 72 h after R-CHOP) is illustrated in FIG. 26 v. Methodology

The indication of the study was prevention of neutropenia or reduction the duration of neutropenia and the incidence of febrile neutropenia in adult patients with Non-Hodgkin's Lymphoma receiving R-CHOP therapy.

All patients received two R-CHOP therapy cycles within the present trial with duration of 21 days of each cycles.

vi. Efficacy and Safety Variables

The parameters of absolute neutrophil count (ANC), white blood cell count (WBC) and differential blood count were determined and recorded in the case report form to assess the efficacy of the test and reference product.

The parameters of evaluation of treatment-emergent adverse events, evaluation of results of clinical examination, evaluation of safety laboratory results, and evaluation of antibodies against GX-G3 were determined for safety of the test and reference products.

The primary endpoint in the present trial was the time to recover from severe neutropenia (defined as ANC <$0.5 \times 10^9$/L) to a target $0.5 \times 10^9$/L after each administration of R-CHOP chemotherapy in cycles 1 and 2.

The secondary endpoints in the present trial were total duration of severe neutropenia in chemotherapy induction cycles 1 and 2, time to recover from severe neutropenia (defined as ANC <$0.5 \times 10^9$/L) to a target $1 \times 10^9$/L and $2 \times 10^9$/L after each administration of R-CHOP chemotherapy in cycles 1 and 2, incidence of febrile neutropenia, incidence of very severe neutropenia (defined as <$0.1 \times 10^9$/L), and incidence of infections.

vii. Statistical Methods

Statistical analysis was performed on three different patient populations: the safety set, the full-analysis set (FAS) and the per-protocol set (PPS).

The safety set consisted of all randomised patients who received at least one dose of the study medication. The full analysis set consisted of all randomised patients who received at least one dose of the study medication and who have at least one post-baseline assessment of the primary endpoint. The per protocol set consisted of all patients of the full analysis set who complete the entire duration of treatment without major protocol violations that could affect the efficacy evaluation Statistical analysis on the primary endpoint is performed using the SAS® software (version 9.4 or higher). The populations for this analysis are the full analysis set and the per protocol set. All statistical tests and comparisons are evaluated at the 5% significance level ($\alpha=5\%$) if not stated otherwise.

The primary endpoint (time to recover from severe neutropenia (defined as ANC <$0.5 \times 10^9$/L) to a target $\geq 0.5 \times 10^9$/L after each administration of R-CHOP chemotherapy in cycles 1 and 2) was compared between each of the doses of the test product and the reference product.

The resulting comparisons of the primary endpoint are:
GX-G3 150 µg/kg BW vs. Reference
GX-G3 250 µg/kg BW vs. Reference
GX-G3 250 µg/kg BW delayed administration vs. Reference
GX-G3 350 µg/kg BW vs. Reference The comparative statistical evaluation of the primary target, i.e. the time to recover from severe neutropenia ($t_{rec}$), is carried out by means of an analysis of covariances (ANCOVA) using treatment, cycle and centre as factors and baseline ANC as a covariate. The comparisons described above were performed both in the PPS and the FAS.

The secondary endpoints undergo descriptive statistical evaluation. The populations for this analysis are the full analysis and the per protocol set. The pharmacokinetic analysis is performed for all patients for whom concentration time data are available and evaluable. The statistical analysis is performed on the per-protocol population. This population is defined as all FAS-evaluable patients who complete the entire duration of treatment without major protocol violations that could affect the efficacy evaluation. Because different analytes are contained in the respective test and reference products (GX-G3 and pegfilgrastim) no comparative analysis is performed.

The safety set was used for the analysis of the safety data. All safety data obtained in this trial were tabulated descriptively with descriptive group statistics (mean, standard deviation, minimum, maximum, number of valid cases) where appropriate. All adverse events were listed.

viii. Clinical Study—Phase II Results

General Characteristics

A total number of 65 patients (35 female and 30 male patients) (safety population; full analysis set) started treatment: 53 patients (29 females, 24 males) were allocated to the test medication (GX-G3 20 mg/mL), 12 patients (6 females, 6 males) were allocated to the reference drug (Neulasta®). The number of patients regarded as per protocol set was 51 (41 patients treated with test, 10 patients treated with reference).

Efficacy Results

Primary Endpoints

The primary objective of the present trial was to assess the efficacy, safety, and tolerability of three doses of GX-G3 with the aim of selecting the optimal dose range by comparing each of the doses with the reference product (Neulasta®). Furthermore, the optimal point in time for dosing of the test product by delayed administration of 250 µg/kg body weight (BW) of GX-G3 72 hours after R-CHOP administration was evaluated.

The primary endpoint was the time to recover from severe neutropenia (defined as ANC <$0.5 \times 10^9$/L) to a target $\geq 0.5 \times 10^9$/L after each administration of R-CHOP chemotherapy in cycles 1 and 2. The mean time to recover from severe neutropenia profiles, which was the primary endpoint of the study, for each treatment cycle and for both cycles together are presented in FIG. 19-23 for PPS and FAS. The mean time to recover from severe neutropenia is presented in Table 17 and Table 18 for the PPS and FAS, respectively.

TABLE 17

The mean and standard deviation for the time (in days) to recover from severe neutropenia for PPS (including patients without neutropenia)

| Treatment group | Mean* | SD | p-Value** |
|---|---|---|---|
| A (GX-G3, 150 µg/kg) (n = 24) | 1.292 | 1.853 | 0.2066 |
| B (GX-G3, 250 µg/kg) (n = 22) | 0.182 | 0.664 | 0.8011 |
| C (GX-G3, 350 µg/kg) (n = 16) | 0.500 | 0.966 | 0.3210 |
| D (Neulasta ®, 6 mg) (n = 20) | 0.250 | 0.550 | — |
| E (GX-G3, +3 days 250 µg/kg) (n = 20) | 0.650 | 1.089 | 0.9826 |

*If ANC did not drop to ANC <0.5 × $10^9$/L, the time to recover from severe neutropenia was defined to be zero.
**The p-values refer to a comparison vs. Neulasta ®

TABLE 18

The mean and standard deviation for the time (in days) to recover from severe neutropenia for FAS (including patients without neutropenia)

| Treatment group | Mean* | SD | p-Value** |
|---|---|---|---|
| A (GX-G3, 150 µg/kg) (n = 27) | 1.704 | 2.233 | 0.4504 |
| B (GX-G3, 250 µg/kg) (n = 24) | 0.417 | 1.018 | 0.5202 |
| C (GX-G3, 350 µg/kg) (n = 23) | 1.174 | 2.167 | 0.4800 |
| D (Neulasta ®, 6 mg) (n = 24) | 1.042 | 2.236 | — |
| E (GX-G3, +3 days 250 µg/kg) (n = 26) | 1.115 | 1.774 | 0.6033 |

*If ANC did not drop to ANC <0.5 × $10^9$/L, the time to recover from severe neutropenia was defined to be zero.
**The p-values refer to a comparison vs. Neulasta ®

As can be seen from Table 17 and Table 18, the time for recovering from severe neutropenia was longest in the group treated with 150 µg/kg GX-G3. The values in the remaining 4 groups were comparable with a tendency for shorter values in the group treated with 250 µg/kg GX-G3.

Secondary Endpoints

The secondary endpoints were total duration of severe neutropenia in chemotherapy induction cycles 1 and 2; time to recover from severe neutropenia (defined as ANC <0.5× $10^9$/L) to a target $1 \times 10^9$/L and $2 \times 10^9$/L after each administration of R-CHOP chemotherapy in cycles 1 and 2; incidence of febrile neutropenia; incidence of very severe neutropenia (defined as <0.1× $10^9$/L); and incidence of infections. Further efficacy parameters in this trial were absolute neutrophil count (ANC); white blood cell count (WBC) and differential blood count.

The total duration of severe neutropenia was calculated as a sum of all individual durations of severe neutropenia registered per treatment group. The results are presented in Table 19 and Table 20 for the PPS and the FAS, respectively. In both analysis populations the longest total duration of severe neutropenia was registered in the group of patients treated with GX-G3 150 µg/kg and the shortest total duration of severe neutropenia was registered in the group of patients treated with GX-G3 250 µg/kg.

TABLE 19

The total duration (day) of severe neutropenia - Sum of individual times to recover from severe neutropenia per treatment group, PPS

| Treatment group | Cyc1 | Cyc2 | Cyc1 + Cyc2 |
|---|---|---|---|
| A (GX-G3, 150 µg/kg) (n = 12) | 17 | 14 | 31 |
| B (GX-G3, 250 µg/kg) (n = 11) | 4 | 0 | 4 |
| C (GX-G3, 350 µg/kg) (n = 8) | 6 | 2 | 8 |
| D (Neulasta ®, 6 mg) (n = 10) | 4 | 1 | 5 |
| E (GX-G3, +3 days 250 µg/kg) (n = 10) | 8 | 5 | 13 |

TABLE 20

The total duration (day) of severe neutropenia - Sum of individual times to recover from severe neutropenia per treatment group, FAS

| Treatment group | Cyc1 | Cyc2 | Cyc1 + Cyc2 |
|---|---|---|---|
| A (GX-G3, 150 µg/kg) (n = 14) | 26 | 20 | 46 |
| B (GX-G3, 250 µg/kg) (n = 12) | 7 | 3 | 10 |
| C (GX-G3, 350 µg/kg) (n = 13) | 21 | 6 | 27 |
| D (Neulasta ®, 6 mg) (n = 14) | 17 | 8 | 25 |
| E (GX-G3, +3 days 250 µg/kg) (n = 12) | 21 | 8 | 29 |

Tables 21 and Table 22 show the time to recover from severe neutropenia to a target ANC $\geq 1 \times 10^9$/L and to a target ANC $\geq 2 \times 10^9$/L in both data sets, per protocol set and full analysis set.

TABLE 21

The mean and standard deviation for the time (in days) to recover from severe neutropenia to targets 1 and 2 G/L, PPS (including patients without neutropenia)

| | Target 1 G/L | | Target 1 G/L | |
|---|---|---|---|---|
| Treatment group | Mean* | SD | Mean* | SD |
| A (GX-G3, 150 µg/kg) (n = 24) | 1.625 | 2.300 | 1.625 | 2.300 |
| B (GX-G3, 250 µg/kg) (n = 22) | 0.182 | 0.664 | 0.182 | 0.664 |
| C (GX-G3, 350 µg/kg) (n = 16) | 0.625 | 1.147 | 0.625 | 1.147 |
| D (Neulasta ®, 6 mg) (n = 20) | 0.350 | 0.745 | 0.500 | 1.100 |
| E (GX-G3, +3 days 250 µg/kg) (n = 20) | 0.900 | 1.683 | 1.150 | 2.084 |

*If ANC did not drop to ANC <0.5 × $10^9$/L, the time to recover from severe neutropenia was defined to be zero.

TABLE 22

The mean and standard deviation for the time (in days) to recover from severe neutropenia to targets 1 and 2 G/L, FAS (including patients without neutropenia:

| | Target 1 G/L | | Target 1 G/L | |
|---|---|---|---|---|
| Treatment group | Mean | SD | Mean | SD |
| A (GX-G3, 150 µg/kg) (n = 27) | 2.074 | 2.556 | 2.074 | 2.556 |
| B (GX-G3, 250 µg/kg) (n = 24) | 0.542 | 1.444 | 0.667 | 1.761 |
| C (GX-G3, 350 µg/kg) (n = 23) | 1.304 | 2.204 | 1.435 | 2.446 |
| D (Neulasta ®, 6 mg) (n = 24) | 1.250 | 2.592 | 1.375 | 2.651 |
| E (GX-G3, +3 days 250 µg/kg) (n = 26) | 1.462 | 2.177 | 1.846 | 2.618 |

*If ANC did not drop to ANC <0.5 × $10^9$/L, the time to recover from severe neutropenia was defined to be zero.

As can be seen from Table 21 and Table 22, the time for recovering from severe neutropenia was longest in the group treated with 150 µg/kg GX-G3. The values in the remaining 4 groups were comparable with shortest values in the group treated with 250 µg/kg GX-G3.

The information about incidences of severe neutropenia, very severe neutropenia and febrile neutropenia in the PPS and FAS are presented in Table 23 and Table 24, respectively. Severe neutropenia was registered in total number of 25 occurrences in the PPS. The percentage of occurrences developing severe neutropenia was highest in the group of patients treated with GX-G3 150 µg/kg and lowest in the group of patients treated with GX-G3 250 µg/kg. In total in a number of 6 patients very severe neutropenia was registered in the PPS and in a total of 18 patients very severe neutropenia was registered in the FAS. The highest number of patients with very severe neutropenia was registered in the group of patients treated with GX-G3 150 µg/kg (n=6) and in those treated with GX-G3 250 µg/kg, delayed (n=5). No febrile neutropenia was registered in the PPS. One patient had febrile neutropenia in the FAS. This patient was treated with GX-G3 350 µg/kg.

TABLE 23

Percent incidences of severe neutropenia in
Cycle 1 and Cycle 2 by treatment group, PPS

| Treatment group | Severe neutropenia | Very severe neutropenia* | Febrile neutropenia |
|---|---|---|---|
| A (GX-G3, 150 µg/kg) (n = 24) | 37.5 | 12.5 | N.O. |
| B (GX-G3, 250 µg/kg) (n = 22) | 9.1 | N.O. | N.O. |
| C (GX-G3, 350 µg/kg) (n = 16) | 25.0 | 6.3 | N.O. |
| D (Neulasta ®, 6 mg) (n = 20) | 20.0 | N.O. | N.O. |
| E (GX-G3, +3 days 250 µg/kg) (n = 20) | 30.0 | 10.0 | N.O. |

N.O.: Not observed.
*Very severe neutropenia (defined as <0.1 × $10^9$/L)

TABLE 24

Percent incidences of severe neutropenia in
Cycle 1 and Cycle 2 by treatment group, FAS

| Treatment group | Severe neutropenia | Very severe neutropenia* | Febrile neutropenia |
|---|---|---|---|
| A (GX-G3, 150 µg/kg) (n = 27) | 44.4 | 22.2 | N.O. |
| B (GX-G3, 250 µg/kg) (n = 24) | 16.7 | 4.2 | N.O. |
| C (GX-G3, 350 µg/kg) (n = 23) | 34.8 | 17.4 | 4.3 |
| D (Neulasta ®, 6 mg) (n = 24) | 29.2 | 8.3 | N.O. |
| E (GX-G3, +3 days 250 µg/kg) (n = 26) | 42.3 | 19.2 | N.O. |

N.O.: Not observed.
*Very severe neutropenia (defined as <0.1 × $10^9$/L)

The incidence of infections is presented in the Table 25 given as incidences by system organ class (SOC) and preferred term (PT) derived from MedDRA. No infections were registered in the groups of patients treated with GX-G3 250 µg/kg and GX-G3 350 µg/kg. The highest number of patients with infection was registered in the group of patients treated with GX-G3 250 µg/kg, delayed (Group E). When the incidence of infection with other endpoints was examined, this rate was 25% in patients using the reference drug Neulasta®, while no infection was seen in patients using GX-G3 at doses 250 µg/kg (Group B) and 350 µg/kg (Group C).

TABLE 25

Frequency of adverse events by PT in SOC 'Infections and
infestations' and by treatment group, safety set

| Incidence of infections | % of subjects |
|---|---|
| A (GX-G3, 150 µg/kg) (n = 14) | 7.1% |
| B (GX-G3, 250 µg/kg) (n = 12) | N.O. |

TABLE 25-continued

Frequency of adverse events by PT in SOC 'Infections and
infestations' and by treatment group, safety set

| Incidence of infections | % of subjects |
|---|---|
| C (GX-G3, 350 µg/kg) (n = 13) | N.O. |
| D (Neulasta ®, 6 mg) (n = 12) | 25% |
| E (GX-G3, +3 days 250 µg/kg) (n = 14) | 35.7% |

N.O.: Not observed

Figure 24:
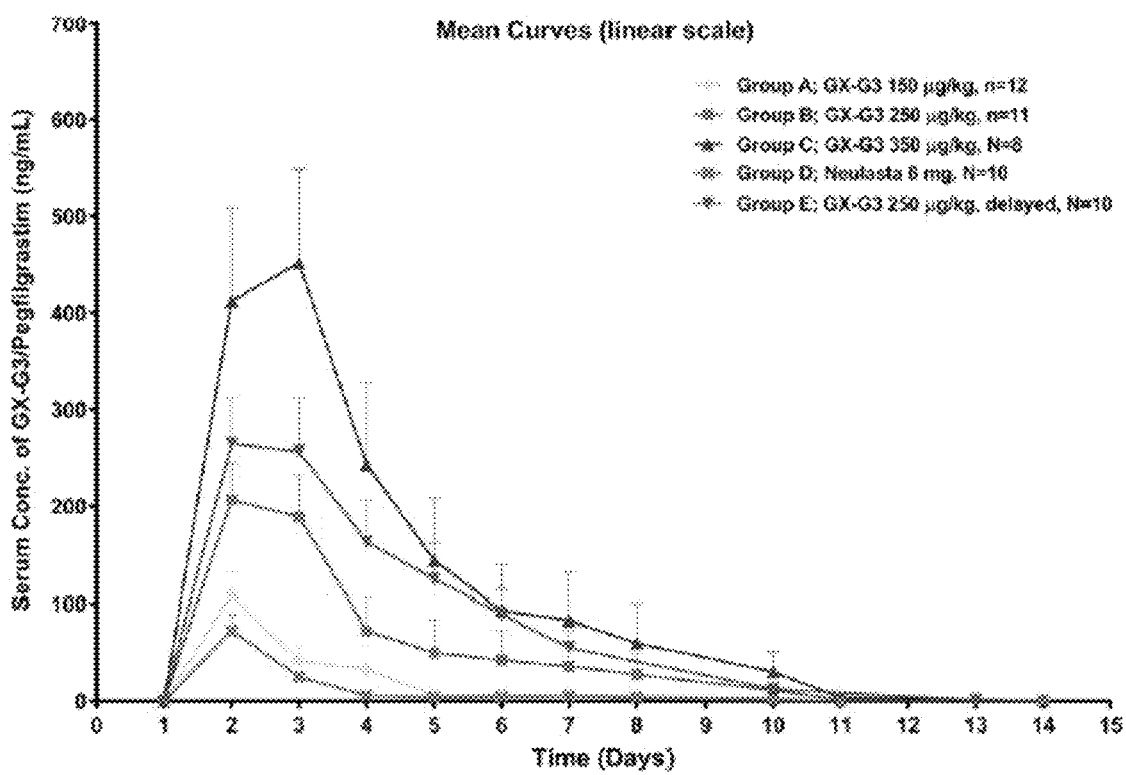
FIG. 24 shows mean concentration vs. time curves for GX-G3 and Pegfilgrastim (PPS).

Concentrations of GX-G3 and pegfilgrastim were measured and the mean concentrations vs. time curves are represented in FIG. 24.

A summary of the calculated pharmacokinetic parameters is represented in Table 26. Pharmacokinetic analysis carried out in Phase II study showed that the parameters AUC and $C_{max}$ of GX-G3 increased in a non-linear, which was not proportional to the dose increase. When the dose increased by a factor of 1.4 (from 150 to 350 µg/kg), $AUC_{last}$ increased by a factor of approximately 7.2 and $C_{max}$ increased by a factor of approximately 4.9.

TABLE 26

Pharmacokinetic parameters determined in Phase II study

| Treatment group | $AUC_{last}$ (ng*h/mL) | $C_{max}$ (ng/mL) | $t_{max}$ (h) | $t_{1/2}$ (h) |
|---|---|---|---|---|
| A (GX-G3, 150 µg/kg) | 5507.0 ± 7119.7 | 108.7 ± 120.85 | 47.91 ± 47.76 | 72.85 ± 68.89 |
| B (GX-G3, 250 µg/kg) | 14190 ± 21095 | 236.52 ± 224.23 | 40.62 ± 33.27 | 54.22 ± 43.01 |
| C (GX-G3, 350 µg/kg) | 34130 ± 33991 | 494.73 ± 400.86 | 55.80 ± 48.34 | 57.98 ± 78.50 |
| D (Neulasta ®, 6 mg) | 3254.2 ± 2179.3 | 75.22 ± 66.20 | 35.75 ± 24.79 | 63.15 ± 65.78 |
| E (GX-G3, +3 days 250 µg/kg) | 36026 ± 36890 | 408.09 ± 368.37 | 54.87 ± 40.05 | 37.19 ± 35.09 |

Evaluation of Efficacy Results

The administration of all doses of GX-G3 and that of Neulasta® led to a pronounced increase of ANC values and effectively counteracted the neutropenic effect of R-CHOP treatment. The delayed administration of GX-G3 was associated with a correspondingly delayed ANC response.

The overall results of the trial can be summarized as follows:

- The doses of 250 μg/kg and 350 μg/kg were comparable with Neulasta® regarding their efficacy and safety.
- The lowest dose of 150 μg/kg as well the 3 days delayed administration of 250 μg/kg are both less effective as compared to Neulasta® but did not differ from Neulasta® regarding their safety.
- The pharmacokinetic parameters AUC and $C_{max}$ of GX-G3 increased in a non-linear, more than proportional way within the dose range between 150 μg/kg and 350 μg/kg.
- The results obtained for the secondary endpoints confirmed the findings obtained for the primary endpoint. No relevant differences were observed between the FAS and the PPS.

Safety Results

Following safety endpoints were defined and analyzed for this Phase II clinical trial for the safety population (n=65):
- Evaluation of treatment-emergent adverse events
- Evaluation of results of clinical examination
- Evaluation of safety laboratory results
- Evaluation of antibodies against GX-G3

Adverse events could be divided into two groups; first group is non-treatment emergent adverse events (all adverse events which occurred before study drug administration) and the second one is treatment emergent adverse events.

In total 252 treatment emergent adverse events were registered in 48 patients (10 patients in each of the groups A-C and 9 patients in each of the groups D and E). The total number of serious adverse events (SAE) was 9 in 5 patients (one patient for each treatment group). A summary displaying the distribution per treatment group is given in Table 27 and Table 28.

TABLE 27

Frequency of adverse events (AEs)

| Treatment group | Frequency of AEs | % of subjects |
| --- | --- | --- |
| A (GX-G3, 150 μg/kg) (n = 14) | 64 | 71.4 |
| B (GX-G3, 250 μg/kg) (n = 12) | 34 | 83.3 |
| C (GX-G3, 350 μg/kg) (n = 13) | 39 | 76.9 |
| D (Neulasta ®, 6 mg) (n = 12) | 52 | 75.0 |
| E (GX-G3, +3 days 250 μg/kg) (n = 14) | 63 | 64.3 |

TABLE 28

Frequency of serious adverse events (SAEs)

| Treatment group | Frequency of AEs | % of subjects |
| --- | --- | --- |
| A (GX-G3, 150 μg/kg) (n = 14) | 2 | 7.1 |
| B (GX-G3, 250 μg/kg) (n = 12) | 1 | 8.3 |
| C (GX-G3, 350 μg/kg) (n = 13) | 2 | 7.7 |
| D (Neulasta ®, 6 mg) (n = 12) | 3 | 8.3 |
| E (GX-G3, +3 days 250 μg/kg) (n = 14) | 1 | 7.1 |

According to results, four different doses of GX-G3 and Neulasta® were generally well tolerated. When adverse events, serious adverse events and laboratory results were examined, no safety concerns were observed for the test drug.

In order to evaluate the immunogenicity of GX-G3 samples for determination of antibodies against GX-G3 were taken at different time points (before the administration of GX-G3 in each treatment cycle and at final examination). In a total number of 5 patients anti-GX-G3 antibodies could be detected. All of these patients were positive for anti-GX-G3 antibodies at baseline. Three of the patients became negative at the final visit, one patient remained positive until the final visit and no further information was available for one patient. No case of newly developed anti-GX-G3 antibodies during the treatment period was registered.

Evaluation of Safety Results

The four different doses and/or dosage regimen of GX-G3 and the reference product were generally well tolerated with no significant difference between GX-G3 and reference product in terms of safety and tolerability.

The analysis of further parameters relevant for safety like AEs, SAEs, vital signs, and results of laboratory examinations did not reveal specific safety concerns related to the test product. No cases of newly developed anti-GX-G3 antibodies were observed.

Overall Conclusion of Phase II Study

The primary objective of the present trial was to assess the efficacy, safety, and tolerability of three doses of GX-G3 with the aim of selecting the optimal dose range by comparing each of the doses with the reference product (Neulasta®). The aim for including one group with delayed administration (250 μg/kg of GX-G3 on day 3 after chemotherapy dosing) was to evaluate the optimal point in time for dosing of the test product.

The administration of all doses of GX-G3 and that of Neulasta® led to a pronounced increase of ANC values and effectively counteracted the neutropenic effect of R-CHOP treatment. The delayed administration of GX-G3 was associated with a correspondingly delayed ANC response.

The overall results of the trial can be summarized as follows:

- The dose of 250 μg/kg and 350 μg/kg were comparable with Neulasta® regarding their efficacy and safety.
- Incidence of infection was found %25 in Group D (Neulasta®) and no infection was observed in Group B and C (250 and 350 μg/kg doses).
- The pharmacokinetic parameters AUC and $C_{max}$ of GX-G3 increased in a non-linear, more than proportional way within the dose range between 150 μg/kg and 350 μg/kg. The results obtained for the secondary endpoints support the findings obtained for the primary endpoint.
- No relevant differences in efficacy results were observed between the FAS and the PPS.
- The analysis of the adverse events did not reveal any differences in safety and tolerability between the test and the reference product.
- The analysis of further parameters relevant for safety like AEs, SAEs, vital signs, and results of laboratory examinations did not reveal specific safety concerns related to the test product.
- No cases of newly developed anti-GX-G3 antibodies were observed.

In summary, among all conducted studies (non-clinical and clinical) it is concluded that 200 μg/kg to 400 μg/kg, preferably 250 μg/kg to 350 μg/kg of GX-G3 administered 24 hours post chemotherapy appears to be the optimal regimen for further clinical studies and getting the target product profile.

The present invention is not to be limited in scope by the specific embodiments described herein. It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

The invention claimed is:

1. A method of preventing neutropenia or reducing the duration of neutropenia of a subject in need thereof, wherein the subject has received or is received an anti-cancer chemotherapy, and wherein the method comprises administering a hybrid Fc fusion G-CSF of the following Formula (I) to the subject at a dose range between about 200 μg/kg and about 400 μg/kg administered 24 hours after the anti-cancer chemotherapy:

$$N'\text{-}G\text{-}Y\text{-}Z2\text{-}Z3\text{-}Z4\text{-}C' \quad \text{Formula (I)}$$

wherein
G is a G-CSF;
N' is the N-terminal of a polypeptide and C' is the C-terminal of a polypeptide;
Y is an amino acid sequence having 5 to 64 consecutive amino acid residues from the amino acid residue at position 162 toward the N-terminal, among the amino acid residues at positions from 99 to 162 of SEQ ID NO: 2;
Z2 is an amino acid sequence having 4 to 37 consecutive amino acid residues from the amino acid residue at position 163 toward the C-terminus, among the amino acid residues at positions from 163 to 199 of SEQ ID NO: 2;
Z3 is an amino acid sequence having 71 to 106 consecutive amino acid residues from the amino acid residue at position 220 toward the N-terminus, among the amino acid residues at positions from 115 to 220 of SEQ ID NO: 3; and
Z4 is an amino acid sequence having 80 to 107 consecutive amino acid residues from the amino acid residue at position 221 toward the C-terminus, among the amino acid residues at positions from 221 to 327 of SEQ ID NO: 3.

2. The method of claim 1, wherein the hybrid Fc fusion G-CSF is administered at a dose range between about 250 μg/kg and about 350 μg/kg.

3. The method of claim 1, wherein the hybrid Fc fusion G-CSF comprises the amino acid sequence of amino acid residues 31 through 449 of SEQ ID NO: 1.

4. The method of claim 1, wherein the hybrid Fc fusion G-CSF is administered parenterally.

5. The method of claim 4, wherein the hybrid Fc fusion G-CSF is administered subcutaneously.

6. The method of claim 1, wherein the hybrid Fc fusion G-CSF is administered to the human subject once in a cycle of chemotherapy.

7. The method of claim 6, wherein the hybrid Fc fusion G-CSF is administered once for every two, three, four or more cycles of chemotherapy.

8. The method of claim 1, wherein the neutrapenia can be moderate or severe.

9. The method of claim 1, wherein the hybrid Fc fusion G-CSF is administered in a pharmaceutical composition comprising the hybrid Fc fusion G-CSF and a pharmaceutically acceptable carrier.

10. A method for increasing neutrophil levels in a subject comprising administering a therapeutically effective amount of a hybrid Fc fusion G-CSF of the following Formula (I) to the subject at a dose range between about 200 μg/kg and about 400 μg/kg:
wherein the subject has received or is receiving an anti-cancer chemotherapy, and wherein the therapeutically effective amount of the hybrid Fc fusion G-CSF is administered 24 hours after the anti-cancer chemotherapy:

$$N'\text{-}G\text{-}Y\text{-}Z2\text{-}Z3\text{-}Z4\text{-}C' \quad \text{Formula (I)}$$

wherein
G is a G-CSF;
N' is the N-terminal of a polypeptide and C' is the C-terminal of a polypeptide;
Y is an amino acid sequence having 5 to 64 consecutive amino acid residues from the amino acid residue at position 162 toward the N-terminal, among the amino acid residues at positions from 99 to 162 of SEQ ID NO: 2;
Z2 is an amino acid sequence having 4 to 37 consecutive amino acid residues from the amino acid residue at position 163 toward the C-terminus, among the amino acid residues at positions from 163 to 199 of SEQ ID NO: 2;
Z3 is an amino acid sequence having 71 to 106 consecutive amino acid residues from the amino acid residue at position 220 toward the N-terminus, among the amino acid residues at positions from 115 to 220 of SEQ ID NO: 3; and
Z4 is an amino acid sequence having 80 to 107 consecutive amino acid residues from the amino acid residue at position 221 toward the C-terminus, among the amino acid residues at positions from 221 to 327 of SEQ ID NO: 3.

11. The method of claim 10, wherein the hybrid Fc fusion G-CSF is administered at a dose range between about 250 μg/kg and about 350 μg/kg.

12. The method of claim 10, wherein the hybrid Fc fusion G-CSF comprises the amino acid sequence of amino acid residues 31 through 449 of SEQ ID NO: 1.

13. The method of claim 10, wherein the hybrid Fc fusion G-CSF is administered parenterally.

14. The method of claim 10, wherein the hybrid Fc fusion G-CSF is administered subcutaneously.

15. The method of claim 10, wherein said subject is a human having circulating neutrophils of lower than about $1.0 \times 10^9$/L blood.

16. The method of claim 10, wherein said subject is a human having circulating neutrophils of lower than about $0.5 \times 10^9$/L blood.

* * * * *

SEQUENCE LISTING

```
<160> NUMBER OF SEQ ID NOS: 4

<210> SEQ ID NO 1
<211> LENGTH: 449
<212> TYPE: PRT
<213> ORGANISM: Artificial Sequence
<220> FEATURE:
<223> OTHER INFORMATION: Amino acid sequence of GX-G3 with signal
      sequence

<400> SEQUENCE: 1

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
        115                 120                 125

Leu Gly Pro Thr Leu Asp Thr Leu Gln Leu Asp Val Ala Asp Phe Ala
    130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro Arg Asn Thr Gly
        195                 200                 205

Arg Gly Gly Glu Glu Lys Lys Glu Lys Glu Lys Glu Glu Gln Glu
    210                 215                 220

Glu Arg Glu Thr Lys Thr Pro Glu Cys Pro Ser His Thr Gln Pro Leu
225                 230                 235                 240

Gly Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
```

```
              305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

Lys

<210> SEQ ID NO 2
<211> LENGTH: 384
<212> TYPE: PRT
<213> ORGANISM: Homo sapiens
<220> FEATURE:
<223> OTHER INFORMATION: amino acid sequence of human IgD constant
      region

<400> SEQUENCE: 2

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
                20                  25                  30

Tyr His Pro Thr Ser Val Thr Val Thr Trp Tyr Met Gly Thr Gln Ser
                35                  40                  45

Gln Pro Gln Arg Thr Phe Pro Glu Ile Gln Arg Arg Asp Ser Tyr Tyr
        50                  55                  60

Met Thr Ser Ser Gln Leu Ser Thr Pro Leu Gln Gln Trp Arg Gln Gly
65              70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
                100                 105                 110

Thr Ala Gln Pro Gln Ala Glu Gly Ser Leu Ala Lys Ala Thr Thr Ala
                115                 120                 125

Pro Ala Thr Thr Arg Asn Thr Gly Arg Gly Gly Glu Glu Lys Lys Lys
        130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
                180                 185                 190

Val Gly Ser Asp Leu Lys Asp Ala His Leu Thr Trp Glu Val Ala Gly
                195                 200                 205

Lys Val Pro Thr Gly Gly Val Glu Glu Gly Leu Leu Glu Arg His Ser
```

```
            210                 215                 220
Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
                245                 250                 255

Pro Pro Gln Arg Leu Met Ala Leu Arg Glu Pro Ala Ala Gln Ala Pro
                260                 265                 270

Val Lys Leu Ser Leu Asn Leu Leu Ala Ser Ser Asp Pro Glu Ala
            275                 280                 285

Ala Ser Trp Leu Leu Cys Glu Val Ser Gly Phe Ser Pro Pro Asn Ile
290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Gly Ser Thr Thr Phe Trp Ala
                325                 330                 335

Trp Ser Val Leu Arg Val Pro Ala Pro Pro Ser Pro Gln Pro Ala Thr
                340                 345                 350

Tyr Thr Cys Val Val Ser His Glu Asp Ser Arg Thr Leu Leu Asn Ala
                355                 360                 365

Ser Arg Ser Leu Glu Val Ser Tyr Val Thr Asp His Gly Pro Met Lys
370                 375                 380

<210> SEQ ID NO 3
<211> LENGTH: 327
<212> TYPE: PRT
<213> ORGANISM: Homo sapiens
<220> FEATURE:
<223> OTHER INFORMATION: amino acid sequence of Partial human IgG4
      constant region

<400> SEQUENCE: 3

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190
```

```
Trp Leu Asn Gly Lys Glu Tyr Lys Cys Lys Val Ser Asn Lys Gly Leu
            195                 200                 205
Pro Ser Ser Ile Glu Lys Thr Ile Ser Lys Ala Lys Gly Gln Pro Arg
        210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 4
<211> LENGTH: 245
<212> TYPE: PRT
<213> ORGANISM: Artificial Sequence
<220> FEATURE:
<223> OTHER INFORMATION: amino acid sequence of hyFc

<400> SEQUENCE: 4

Arg Asn Thr Gly Arg Gly Gly Glu Glu Lys Lys Lys Glu Lys Glu Lys
1               5                   10                  15
Glu Glu Gln Glu Glu Arg Glu Thr Lys Thr Pro Glu Cys Pro Ser His
            20                  25                  30
Thr Gln Pro Leu Gly Val Phe Leu Phe Pro Pro Lys Pro Lys Asp Thr
        35                  40                  45
Leu Met Ile Ser Arg Thr Pro Glu Val Thr Cys Val Val Val Asp Val
    50                  55                  60
Ser Gln Glu Asp Pro Glu Val Gln Phe Asn Trp Tyr Val Asp Gly Val
65                  70                  75                  80
Glu Val His Asn Ala Lys Thr Lys Pro Arg Glu Glu Gln Phe Asn Ser
                85                  90                  95
Thr Tyr Arg Val Val Ser Val Leu Thr Val Leu His Gln Asp Trp Leu
            100                 105                 110
Asn Gly Lys Glu Tyr Lys Cys Lys Val Ser Asn Lys Gly Leu Pro Ser
        115                 120                 125
Ser Ile Glu Lys Thr Ile Ser Lys Ala Lys Gly Gln Pro Arg Glu Pro
    130                 135                 140
Gln Val Tyr Thr Leu Pro Pro Ser Gln Glu Glu Met Thr Lys Asn Gln
145                 150                 155                 160
Val Ser Leu Thr Cys Leu Val Lys Gly Phe Tyr Pro Ser Asp Ile Ala
                165                 170                 175
Val Glu Trp Glu Ser Asn Gly Gln Pro Glu Asn Asn Tyr Lys Thr Thr
            180                 185                 190
Pro Pro Val Leu Asp Ser Asp Gly Ser Phe Phe Leu Tyr Ser Arg Leu
        195                 200                 205
Thr Val Asp Lys Ser Arg Trp Gln Glu Gly Asn Val Phe Ser Cys Ser
    210                 215                 220
```

```
Val Met His Glu Ala Leu His Asn His Tyr Thr Gln Lys Ser Leu Ser
225                 230                 235                 240

Leu Ser Leu Gly Lys
            245
```